United States Patent
Shalev et al.

(10) Patent No.: US 10,888,413 B2
(45) Date of Patent: Jan. 12, 2021

(54) MULTI-COMPONENT STENT-GRAFT SYSTEM FOR IMPLANTATION IN A BLOOD VESSEL WITH MULTIPLE BRANCHES

(71) Applicant: ENDOSPAN LTD., Herzilyia Pituach (IL)

(72) Inventors: Alon Shalev, Ra'anana (IL); Sagi Raz, Tel Aviv (IL); Rafi Benary, Tel Aviv (IL)

(73) Assignee: ENDOSPAN LTD., Herzilyia Pituach (IL)

( * ) Notice: Subject to any disclaimer, the term of this patent is extended or adjusted under 35 U.S.C. 154(b) by 0 days.

(21) Appl. No.: 16/228,986

(22) Filed: Dec. 21, 2018

(65) Prior Publication Data

US 2019/0183630 A1    Jun. 20, 2019

Related U.S. Application Data

(63) Continuation of application No. 14/572,156, filed on Dec. 16, 2014, now Pat. No. 10,201,413, which is a continuation of application No. 13/512,778, filed as application No. PCT/IL2010/000999 on Nov. 30, 2010, now Pat. No. 8,945,203.

(60) Provisional application No. 61/264,861, filed on Nov. 30, 2009.

(51) Int. Cl.
*A61F 2/07*     (2013.01)
*A61F 2/90*     (2013.01)
*A61F 2/06*     (2013.01)

(52) U.S. Cl.
CPC .................. *A61F 2/07* (2013.01); *A61F 2/90* (2013.01); *A61F 2002/061* (2013.01); *A61F 2250/006* (2013.01); *A61F 2250/0039* (2013.01); *A61F 2250/0065* (2013.01)

(58) Field of Classification Search
CPC ..................................... A61F 2/07; A61F 2/90
See application file for complete search history.

(56) References Cited

U.S. PATENT DOCUMENTS

| | | |
|---|---|---|
| 4,180,613 A | 12/1979 | Vassiliou |
| 4,355,426 A | 10/1982 | MacGregor |
| 4,505,767 A | 3/1985 | Quin |
| 4,562,596 A | 1/1986 | Kornberg |

(Continued)

FOREIGN PATENT DOCUMENTS

| | | |
|---|---|---|
| CA | 2 497 704 | 3/2004 |
| CN | 1194577 | 9/1998 |

(Continued)

OTHER PUBLICATIONS

"E-vita® open plus" product brochure (JOTEC GmbH, Hechingen, Germany), 2010.

(Continued)

*Primary Examiner* — Matthew W Schall
(74) *Attorney, Agent, or Firm* — Sughrue Mion, PLLC

(57) ABSTRACT

A multi-component stent-graft system is provided, which includes a first stent-graft, which is configured to assume radially-expanded and radially-compressed states; and a second stent-graft, which is configured to assume radially-expanded and radially-compressed states. A delivery tool includes an outer tube, in which the first and the second stent-grafts are initially positioned at respective axial sites within the outer tube, in their radially-compressed states without being fixed to each other. Other embodiments are also described.

12 Claims, 32 Drawing Sheets

(56) References Cited

U.S. PATENT DOCUMENTS

| | | |
|---|---|---|
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,816,339 A | 3/1989 | Tu et al. |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,129,910 A | 7/1992 | Phan et al. |
| 5,133,732 A | 7/1992 | Wiktor |
| 5,192,286 A | 3/1993 | Phan et al. |
| 5,234,448 A | 8/1993 | Wholey et al. |
| 5,425,765 A | 6/1995 | Tiefenbrun et al. |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,662,675 A | 9/1997 | Polanskyj Stockert et al. |
| 5,676,696 A | 10/1997 | Marcade |
| 5,676,697 A | 10/1997 | McDonald |
| 5,728,134 A | 3/1998 | Barak |
| 5,749,825 A | 5/1998 | Fischell et al. |
| 5,749,879 A | 5/1998 | Middleman et al. |
| 5,755,770 A | 5/1998 | Ravenscroft |
| 5,755,771 A | 5/1998 | Penn et al. |
| 5,755,774 A | 5/1998 | Pinchuk |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,824,040 A | 10/1998 | Cox et al. |
| 5,827,321 A | 10/1998 | Roubin |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,976,178 A | 11/1999 | Goldsteen et al. |
| 5,980,552 A | 11/1999 | Pinchasik |
| 6,015,431 A | 1/2000 | Thornton et al. |
| 6,016,810 A | 1/2000 | Ravenscroft |
| 6,030,414 A | 2/2000 | Taheri |
| 6,033,435 A | 3/2000 | Penn et al. |
| 6,036,725 A | 3/2000 | Avellanet |
| 6,049,824 A | 4/2000 | Taheri |
| 6,077,298 A | 6/2000 | Tu et al. |
| 6,099,497 A | 8/2000 | Adams et al. |
| 6,117,145 A | 9/2000 | Wood et al. |
| 6,152,956 A | 11/2000 | Pierce |
| 6,156,064 A | 12/2000 | Chouinard |
| 6,168,615 B1 | 1/2001 | Ken et al. |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,290,720 B1 | 9/2001 | Khosravi et al. |
| 6,312,458 B1 | 11/2001 | Golds |
| 6,319,287 B1 | 11/2001 | Frimberger |
| 6,325,823 B1 | 12/2001 | Horzewski et al. |
| 6,344,056 B1 | 2/2002 | Dehdashtian |
| 6,395,018 B1 | 5/2002 | Castaneda |
| 6,406,420 B1 | 6/2002 | McCarthy |
| 6,428,565 B1 | 8/2002 | Wisselink |
| 6,451,048 B1 | 9/2002 | Berg et al. |
| 6,506,211 B1 | 1/2003 | Skubitz et al. |
| 6,565,597 B1 | 5/2003 | Fearnot et al. |
| 6,613,075 B1 | 9/2003 | Healy et al. |
| 6,613,078 B1 | 9/2003 | Barone |
| 6,635,083 B1 | 10/2003 | Cheng et al. |
| 6,645,242 B1 | 11/2003 | Quinn |
| 6,648,901 B2 | 11/2003 | Fleischman et al. |
| 6,648,911 B1 | 11/2003 | Sirhan |
| 6,652,567 B1 | 11/2003 | Deaton |
| 6,656,214 B1 | 12/2003 | Fogarty et al. |
| 6,673,080 B2 | 1/2004 | Reynolds et al. |
| 6,692,520 B1 | 2/2004 | Gambale et al. |
| 6,695,833 B1 | 2/2004 | Frantzen |
| 6,695,875 B2 | 2/2004 | Shelter et al. |
| 6,729,356 B1 | 5/2004 | Baker et al. |
| 6,730,117 B1 | 5/2004 | Tseng et al. |
| 6,743,195 B2 | 6/2004 | Zucker |
| 6,748,953 B2 | 6/2004 | Sherry et al. |
| 6,752,826 B2 | 6/2004 | Wholey et al. |
| 6,776,794 B1 | 8/2004 | Hong et al. |
| 6,808,534 B1 | 10/2004 | Escano |
| 6,814,749 B2 | 11/2004 | Cox et al. |
| 6,814,752 B1 | 11/2004 | Chuter |
| 6,824,560 B2 | 11/2004 | Pelton |
| 6,846,321 B2 | 1/2005 | Zucker |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,953,469 B2 | 10/2005 | Ryan |
| 6,964,679 B1 | 11/2005 | Marcade et al. |
| 6,986,774 B2 | 1/2006 | Middleman et al. |
| 7,008,441 B2 | 3/2006 | Zucker |
| 7,022,131 B1 | 4/2006 | DeRowe et al. |
| 7,044,962 B2 | 5/2006 | Elliott |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,122,052 B2 | 10/2006 | Greenhalgh |
| 7,144,421 B2 | 12/2006 | Carpenter et al. |
| 7,175,651 B2 | 2/2007 | Kerr |
| 7,198,638 B2 | 4/2007 | Dong |
| 7,201,772 B2 | 4/2007 | Schwammenthal et al. |
| 7,223,266 B2 | 5/2007 | Lindenbaum et al. |
| 7,261,733 B1 | 8/2007 | Brown et al. |
| 7,279,003 B2 | 10/2007 | Berra et al. |
| 7,294,145 B2 | 11/2007 | Ward |
| 7,306,623 B2 | 12/2007 | Watson |
| 7,341,598 B2 | 3/2008 | Davidson et al. |
| 7,399,313 B2 | 7/2008 | Brown et al. |
| 7,407,509 B2 | 8/2008 | Greenberg et al. |
| 7,413,573 B2 | 8/2008 | Hartley et al. |
| 7,429,269 B2 | 9/2008 | Schwammenthal et al. |
| 7,442,204 B2 | 10/2008 | Schwammenthal et al. |
| 7,473,272 B2 | 1/2009 | Pryor |
| 7,537,609 B2 | 5/2009 | Davidson et al. |
| 7,540,881 B2 | 6/2009 | Meyer et al. |
| 7,544,160 B2 | 6/2009 | Gross |
| 7,616,997 B2 | 11/2009 | Kieval et al. |
| 7,637,939 B2 | 12/2009 | Tischler |
| 7,645,298 B2 | 1/2010 | Hartley et al. |
| 7,662,161 B2 | 2/2010 | Briganti et al. |
| 7,662,168 B2 | 2/2010 | McGuckin, Jr. et al. |
| 7,670,369 B2 | 3/2010 | Schaeffer |
| 7,678,141 B2 | 3/2010 | Greenan et al. |
| 7,708,704 B2 | 5/2010 | Mitelberg |
| 7,722,626 B2 | 5/2010 | Middleman et al. |
| 7,731,732 B2 | 6/2010 | Ken |

(56) References Cited

U.S. PATENT DOCUMENTS

| | | |
|---|---|---|
| 7,803,178 B2 | 9/2010 | Whirley |
| 7,806,923 B2 | 10/2010 | Moloney |
| 7,815,673 B2 | 10/2010 | Bloom et al. |
| 7,833,259 B2 | 11/2010 | Boatman |
| 7,887,575 B2 | 2/2011 | Kujawski |
| 7,914,572 B2 | 3/2011 | Hartley et al. |
| 7,955,374 B2 | 6/2011 | Erickson et al. |
| 7,959,662 B2 | 6/2011 | Erbel et al. |
| 8,021,419 B2 | 9/2011 | Hartley et al. |
| 8,043,365 B2 | 10/2011 | Thramann |
| 8,048,140 B2 | 11/2011 | Purdy |
| 8,052,741 B2 | 11/2011 | Bruszewski et al. |
| 8,066,755 B2 | 11/2011 | Zacharias |
| 8,080,026 B2 | 12/2011 | Konstantino et al. |
| 8,080,053 B2 | 12/2011 | Satasiya |
| 8,100,960 B2 | 1/2012 | Bruszewski |
| 8,157,810 B2 | 4/2012 | Case et al. |
| 8,167,926 B2 | 5/2012 | Hartley et al. |
| 8,172,892 B2 | 5/2012 | Chuter |
| 8,197,475 B2 | 6/2012 | Bruszewski et al. |
| 8,211,158 B2 | 7/2012 | Wolf |
| 8,216,298 B2 | 7/2012 | Wright et al. |
| 8,221,494 B2 | 7/2012 | Schreck et al. |
| 8,226,706 B2 | 7/2012 | Hartley et al. |
| 8,251,963 B2 | 8/2012 | Chin et al. |
| 8,262,719 B2 | 9/2012 | Erickson et al. |
| 8,273,115 B2 | 9/2012 | Hamer et al. |
| 8,292,951 B2 | 10/2012 | Muzslay |
| 8,333,800 B2 | 12/2012 | Bruszewski et al. |
| 8,353,898 B2 | 1/2013 | Lutze et al. |
| 8,394,136 B2 | 3/2013 | Hartley et al. |
| 8,506,622 B2 | 8/2013 | Bruszewski et al. |
| 8,728,148 B2 | 5/2014 | Roeder et al. |
| 8,808,355 B2 | 8/2014 | Barrand |
| 8,945,203 B2 | 2/2015 | Shalev et al. |
| 8,968,384 B2 | 3/2015 | Pearson et al. |
| 9,101,457 B2 | 8/2015 | Benary |
| 9,168,123 B2 | 10/2015 | Barrand |
| 9,254,209 B2 | 2/2016 | Shalev |
| 10,201,413 B2 | 2/2019 | Shalev et al. |
| 2001/0004705 A1 | 6/2001 | Killion |
| 2001/0010006 A1 | 7/2001 | Bachinski et al. |
| 2001/0014823 A1 | 8/2001 | Resseman et al. |
| 2001/0034550 A1 | 10/2001 | Buirge |
| 2001/0044647 A1 | 11/2001 | Pinchuk et al. |
| 2001/0044651 A1 | 11/2001 | Steinke |
| 2001/0044652 A1 | 11/2001 | Moore |
| 2001/0047198 A1 | 11/2001 | Drasler |
| 2001/0053930 A1 | 12/2001 | Kugler et al. |
| 2002/0040236 A1 | 4/2002 | Lau |
| 2002/0052644 A1 | 5/2002 | Shaolian et al. |
| 2002/0099438 A1 | 7/2002 | Furst |
| 2002/0099441 A1 | 7/2002 | Dehdashtian |
| 2002/0107564 A1 | 8/2002 | Cox |
| 2002/0123791 A1 | 9/2002 | Harrison |
| 2002/0156495 A1 | 10/2002 | Brenneman et al. |
| 2002/0156517 A1 | 10/2002 | Prouse et al. |
| 2003/0040791 A1 | 2/2003 | Oktay |
| 2003/0040804 A1 | 2/2003 | Stack et al. |
| 2003/0057156 A1 | 3/2003 | Peterson et al. |
| 2003/0065345 A1 | 4/2003 | Weadock |
| 2003/0074055 A1 | 4/2003 | Haverkost |
| 2003/0093145 A1 | 5/2003 | Lawrence-Brown et al. |
| 2003/0114061 A1 | 6/2003 | Matsuda et al. |
| 2003/0130720 A1 | 7/2003 | DePalma et al. |
| 2003/0139802 A1 | 7/2003 | Wulfman et al. |
| 2003/0139805 A1 | 7/2003 | Holmberg et al. |
| 2003/0144725 A1 | 7/2003 | Lombardi |
| 2003/0153944 A1 | 8/2003 | Phung et al. |
| 2003/0153968 A1 | 8/2003 | Geis et al. |
| 2003/0163187 A1 | 8/2003 | Weber |
| 2003/0191523 A1 | 10/2003 | Hojeibane |
| 2003/0199967 A1 | 10/2003 | Hartley et al. |
| 2003/0199968 A1 | 10/2003 | Ainsworth et al. |
| 2003/0204236 A1 | 10/2003 | Letort |
| 2003/0204242 A1 | 10/2003 | Zarins et al. |
| 2003/0212449 A1 | 11/2003 | Cox |
| 2003/0236567 A1 | 12/2003 | Elliot |
| 2004/0015227 A1 | 1/2004 | Vardi et al. |
| 2004/0015229 A1 | 1/2004 | Fulkerson |
| 2004/0098091 A1 | 5/2004 | Erbel |
| 2004/0106972 A1 | 6/2004 | Deaton |
| 2004/0106978 A1 | 6/2004 | Greenberg et al. |
| 2004/0117003 A1 | 6/2004 | Ouriel et al. |
| 2004/0133266 A1 | 7/2004 | Clerc et al. |
| 2004/0171978 A1 | 9/2004 | Shalaby |
| 2004/0176832 A1 | 9/2004 | Hartley et al. |
| 2004/0181149 A1 | 9/2004 | Langlotz et al. |
| 2004/0215319 A1 | 10/2004 | Berra et al. |
| 2004/0215327 A1 | 10/2004 | Doig et al. |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0070995 A1 | 3/2005 | Zilla et al. |
| 2005/0085900 A1 | 4/2005 | Case |
| 2005/0102018 A1 | 5/2005 | Carpenter et al. |
| 2005/0102021 A1 | 5/2005 | Osborne |
| 2005/0131512 A1 | 6/2005 | Vonderwalde |
| 2005/0131517 A1 | 6/2005 | Hartley et al. |
| 2005/0143802 A1 | 6/2005 | Soykan et al. |
| 2005/0149166 A1 | 7/2005 | Schaeffer et al. |
| 2005/0154448 A1 | 7/2005 | Cully |
| 2005/0171598 A1 | 8/2005 | Schaeffer et al. |
| 2005/0177132 A1 | 8/2005 | Lentz et al. |
| 2005/0177222 A1 | 8/2005 | Mead |
| 2005/0177224 A1 | 8/2005 | Fogarty et al. |
| 2005/0203606 A1 | 9/2005 | VanCamp |
| 2005/0216018 A1 | 9/2005 | Sennett et al. |
| 2005/0222649 A1 | 10/2005 | Capuano |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0234542 A1 | 10/2005 | Melsheimer |
| 2005/0266042 A1 | 12/2005 | Tseng |
| 2005/0283188 A1 | 12/2005 | Loshakove et al. |
| 2006/0015170 A1 | 1/2006 | Jones et al. |
| 2006/0052799 A1 | 3/2006 | Middleman et al. |
| 2006/0069426 A1 | 3/2006 | Weinberger |
| 2006/0095104 A1 | 5/2006 | Magers et al. |
| 2006/0095114 A1 | 5/2006 | Hartley et al. |
| 2006/0100684 A1 | 5/2006 | Elliott |
| 2006/0106406 A1 | 5/2006 | Weinberger |
| 2006/0149360 A1 | 7/2006 | Schwammenthal et al. |
| 2006/0155358 A1 | 7/2006 | LaDuca et al. |
| 2006/0155359 A1 | 7/2006 | Watson |
| 2006/0155366 A1 | 7/2006 | LaDuca et al. |
| 2006/0167476 A1 | 7/2006 | Burdulis, Jr. et al. |
| 2006/0173530 A1 | 8/2006 | Das |
| 2006/0178733 A1 | 8/2006 | Pinchuk et al. |
| 2006/0193892 A1 | 8/2006 | Furst et al. |
| 2006/0229709 A1 | 10/2006 | Morris et al. |
| 2006/0241740 A1 | 10/2006 | Vardi et al. |
| 2006/0247761 A1 | 11/2006 | Greenberg et al. |
| 2006/0281966 A1 | 12/2006 | Peacock, III |
| 2007/0021822 A1 | 1/2007 | Boatman |
| 2007/0043425 A1 | 2/2007 | Hartley et al. |
| 2007/0050011 A1 | 3/2007 | Klein |
| 2007/0055350 A1 | 3/2007 | Erickson et al. |
| 2007/0055358 A1 | 3/2007 | Krolik et al. |
| 2007/0060989 A1 | 3/2007 | Deem et al. |
| 2007/0061002 A1 | 3/2007 | Paul, Jr. |
| 2007/0067014 A1 | 3/2007 | Ke et al. |
| 2007/0073373 A1 | 3/2007 | Bonsignore |
| 2007/0088425 A1 | 4/2007 | Schaeffer |
| 2007/0106368 A1 | 5/2007 | Vonderwalde |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Arnault de la et al. |
| 2007/0156167 A1 | 7/2007 | Connors et al. |
| 2007/0167898 A1 | 7/2007 | Peters et al. |
| 2007/0168018 A1 | 7/2007 | Amplatz |
| 2007/0179598 A1 | 8/2007 | Duerig |
| 2007/0185565 A1 | 8/2007 | Schwammenthal et al. |

(56) References Cited

U.S. PATENT DOCUMENTS

| | | |
|---|---|---|
| 2007/0208410 A1 | 9/2007 | Berra et al. |
| 2007/0213805 A1 | 9/2007 | Schaeffer et al. |
| 2007/0213807 A1 | 9/2007 | Roubin |
| 2007/0219610 A1 | 9/2007 | Israel |
| 2007/0219614 A1 | 9/2007 | Hartley |
| 2007/0219627 A1 | 9/2007 | Chu |
| 2007/0233229 A1 | 10/2007 | Berra et al. |
| 2007/0237973 A1 | 10/2007 | Purdy et al. |
| 2007/0239256 A1 | 10/2007 | Weber et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0015682 A1 | 1/2008 | Majercak et al. |
| 2008/0033527 A1 | 2/2008 | Nunez et al. |
| 2008/0058918 A1 | 3/2008 | Watson |
| 2008/0064957 A1 | 3/2008 | Spence |
| 2008/0086193 A1 | 4/2008 | Thramann |
| 2008/0109058 A1 | 5/2008 | Greenberg et al. |
| 2008/0109066 A1 | 5/2008 | Quinn |
| 2008/0114444 A1 | 5/2008 | Yu |
| 2008/0114445 A1 | 5/2008 | Melsheimer et al. |
| 2008/0114446 A1 | 5/2008 | Hartley et al. |
| 2008/0140178 A1 | 6/2008 | Rasmussen et al. |
| 2008/0147173 A1 | 6/2008 | McIff et al. |
| 2008/0167704 A1 | 7/2008 | Wright et al. |
| 2008/0176271 A1 | 7/2008 | Silver et al. |
| 2008/0195190 A1 | 8/2008 | Bland et al. |
| 2008/0195191 A1 | 8/2008 | Luo |
| 2008/0249598 A1 | 10/2008 | Sherry |
| 2008/0262595 A1 | 10/2008 | Chu et al. |
| 2008/0262598 A1 | 10/2008 | Elmaleh |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0294234 A1 | 11/2008 | Hartley et al. |
| 2008/0300665 A1 | 12/2008 | Lootz |
| 2008/0312732 A1 | 12/2008 | Hartley et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030497 A1 | 1/2009 | Metcalf et al. |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang |
| 2009/0069881 A1 | 3/2009 | Chalekian et al. |
| 2009/0069882 A1 | 3/2009 | Venturelli |
| 2009/0082841 A1 | 3/2009 | Zacharias |
| 2009/0099648 A1 | 4/2009 | Yu |
| 2009/0099649 A1 | 4/2009 | Chobotov et al. |
| 2009/0099650 A1 | 4/2009 | Bolduc et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0157014 A1 | 6/2009 | Osborne et al. |
| 2009/0164001 A1 | 6/2009 | Biggs et al. |
| 2009/0171437 A1 | 7/2009 | Brocker et al. |
| 2009/0182270 A1 | 7/2009 | Nanavati |
| 2009/0182405 A1 | 7/2009 | Arnault De La Menardiere et al. |
| 2009/0227997 A1 | 9/2009 | Wang |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2009/0319022 A1 | 12/2009 | Hartley et al. |
| 2010/0004728 A1 | 1/2010 | Rao |
| 2010/0029608 A1 | 2/2010 | Finley |
| 2010/0057186 A1 | 3/2010 | West et al. |
| 2010/0063575 A1 | 3/2010 | Shalev |
| 2010/0070019 A1 | 3/2010 | Shalev |
| 2010/0082091 A1 | 4/2010 | Berez |
| 2010/0161025 A1 | 6/2010 | Kuppurathanam et al. |
| 2010/0161026 A1 | 6/2010 | Brocker et al. |
| 2010/0161028 A1 | 6/2010 | Chuter et al. |
| 2010/0211159 A1 | 8/2010 | Schmid |
| 2010/0249899 A1 | 9/2010 | Chuter et al. |
| 2010/0256725 A1 | 10/2010 | Rasmussen |
| 2010/0268327 A1 | 10/2010 | Bruszewski et al. |
| 2010/0274187 A1 | 10/2010 | Argentine |
| 2010/0274345 A1 | 10/2010 | Rust |
| 2010/0292774 A1 | 11/2010 | Shalev |
| 2010/0312326 A1 | 12/2010 | Chuter et al. |
| 2010/0318171 A1 | 12/2010 | Porter |
| 2011/0022149 A1 | 1/2011 | Cox et al. |
| 2011/0093002 A1 | 4/2011 | Rucker et al. |
| 2011/0125251 A1 | 5/2011 | Cottone |
| 2011/0152998 A1 | 6/2011 | Berez et al. |
| 2011/0208289 A1 | 8/2011 | Shalev |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218607 A1 | 9/2011 | Arbefeuille et al. |
| 2011/0257720 A1 | 10/2011 | Peterson et al. |
| 2011/0257725 A1 | 10/2011 | Argentine |
| 2011/0262684 A1 | 10/2011 | Wintsch et al. |
| 2011/0264184 A1 | 10/2011 | Heltai |
| 2011/0264192 A1 | 10/2011 | Hartley et al. |
| 2011/0270385 A1 | 11/2011 | Muzslay |
| 2011/0301702 A1 | 12/2011 | Rust et al. |
| 2011/0319983 A1 | 12/2011 | Zhu et al. |
| 2012/0143317 A1 | 6/2012 | Cam et al. |
| 2012/0158038 A1 | 6/2012 | Leschinsky |
| 2012/0172965 A1 | 7/2012 | Kratzberg et al. |
| 2012/0179236 A1 | 7/2012 | Benary |
| 2012/0185031 A1 | 7/2012 | Ryan et al. |
| 2012/0271401 A1 | 10/2012 | Bruszewski et al. |
| 2013/0013050 A1 | 1/2013 | Shalev et al. |
| 2013/0046371 A1 | 2/2013 | Greenberg et al. |
| 2013/0116773 A1 | 5/2013 | Roeder et al. |
| 2013/0116775 A1 | 5/2013 | Roeder et al. |
| 2013/0158646 A1 | 6/2013 | Roeder |
| 2013/0274866 A1 | 10/2013 | Cox et al. |
| 2013/0289691 A1 | 10/2013 | Argentine et al. |
| 2013/0338787 A1 | 12/2013 | Hopkins et al. |
| 2014/0148888 A1 | 5/2014 | Barrand |
| 2014/0180378 A1 | 6/2014 | Roeder |
| 2014/0350658 A1 | 11/2014 | Benary et al. |
| 2014/0364930 A1 | 12/2014 | Strauss et al. |
| 2015/0073534 A1 | 3/2015 | Roeder et al. |
| 2015/0105851 A1 | 4/2015 | Shalev et al. |
| 2015/0196301 A1 | 7/2015 | Bodewadt et al. |
| 2015/0374383 A1 | 12/2015 | Bodewadt et al. |
| 2016/0262880 A1 | 9/2016 | Li et al. |

FOREIGN PATENT DOCUMENTS

| | | |
|---|---|---|
| CN | 1748660 | 3/2006 |
| CN | 201058061 | 5/2008 |
| DE | 10213055 | 9/2002 |
| EP | 1 177 780 | 2/2002 |
| EP | 1 325 716 | 7/2003 |
| EP | 1470797 | 10/2004 |
| EP | 1759666 | 3/2007 |
| EP | 2298248 | 3/2011 |
| JP | 2002-253682 | 9/2002 |
| WO | 98/06355 | 2/1998 |
| WO | 99/34748 | 7/1999 |
| WO | 00/28923 | 5/2000 |
| WO | 2000/074595 | 12/2000 |
| WO | 2000/076423 | 12/2000 |
| WO | 2001/052776 | 7/2001 |
| WO | 2002/083038 | 10/2002 |
| WO | 03/099108 | 12/2003 |
| WO | 2004/017868 | 3/2004 |
| WO | 2004/100836 | 11/2004 |
| WO | 05/002466 | 1/2005 |

(56) References Cited

FOREIGN PATENT DOCUMENTS

| | | |
|---|---|---|
| WO | 2005/034809 | 4/2005 |
| WO | 2005/037138 | 4/2005 |
| WO | 2005/041781 | 5/2005 |
| WO | 2005/041783 | 5/2005 |
| WO | 2005/046524 | 5/2005 |
| WO | 2005/046526 | 5/2005 |
| WO | 2006/007389 | 1/2006 |
| WO | 2006/028925 | 3/2006 |
| WO | 2006/036690 | 4/2006 |
| WO | 06/070372 | 7/2006 |
| WO | 2006/088905 | 8/2006 |
| WO | 2006/130755 | 12/2006 |
| WO | 2007/084547 | 7/2007 |
| WO | 2007/115017 | 10/2007 |
| WO | 2007/144782 | 12/2007 |
| WO | 08/008291 | 1/2008 |
| WO | 2008/021557 | 2/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/051704 | 5/2008 |
| WO | 2008/053469 | 5/2008 |
| WO | 2008/066923 | 6/2008 |
| WO | 2008/107885 | 9/2008 |
| WO | 2008/140796 | 11/2008 |
| WO | 2009/078010 | 6/2009 |
| WO | 2009/104000 | 8/2009 |
| WO | 2009/116041 | 9/2009 |
| WO | 2009/116042 | 9/2009 |
| WO | 09/118733 | 10/2009 |
| WO | 2010/024869 | 3/2010 |
| WO | 2010/024879 | 3/2010 |
| WO | 2010/031060 | 3/2010 |
| WO | 2010/042210 | 4/2010 |
| WO | 2010/045238 | 4/2010 |
| WO | 2010/062355 | 6/2010 |
| WO | 10/088776 | 8/2010 |
| WO | 2010/111583 | 9/2010 |
| WO | 2010/128162 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |
| WO | 2011/067764 | 6/2011 |
| WO | 2011/070576 | 6/2011 |
| WO | 2011/080738 | 7/2011 |
| WO | 2011/095979 | 8/2011 |
| WO | 2011/100290 | 8/2011 |
| WO | 2011/106532 | 9/2011 |
| WO | 2011/106533 | 9/2011 |
| WO | 2011/106544 | 9/2011 |
| WO | 2011/116307 | 9/2011 |
| WO | 2011/136930 | 11/2011 |

OTHER PUBLICATIONS

Fonseca A et al., "Intravascular ultrasound assessment of the novel AngioSculpt scoring balloon catheter for the treatment of complex coronary lesions," J Invasive Cardiol 20(1):21-7 (Jan. 2008).
Khlif H et al., "Contribution to the Improvement of Textile Vascular Prostheses Crimping," Trends in Applied Sciences Research 6(9):1019-1027 (2011).
An International Search Report dated Sep. 29, 2008, which issued during the prosecution of Applicant's PCT/IL08/000287.
A Written Opinion dated Sep. 29, 2008, which issued during the prosecution of Applicant's PCT/IL08/000287.
An Office Action dated Mar. 28, 2014, which issued during the prosecution of U.S. Appl. No. 13/519,971.
An International Search Report dated Feb. 4, 2011, which issued during the prosecution of Applicant's PCT/IB2010/052861.
A Written Opinion dated Feb. 4, 2011, which issued during the prosecution of Applicant's PCT/IB2010/052861.
An International Search Report dated Dec. 3, 2010, which issued during the prosecution of Applicant's PCT/IL2010/000564.
A Written Opinion dated Dec. 3, 2010, which issued during the prosecution of Applicant's PCT/IL2010/000564.
An International Search Report dated Nov. 5, 2010, which issued during the prosecution of Applicant's PCT/IL2010/000549.
A Written Opinion dated Nov. 5, 2010, which issued during the prosecution of Applicant's PCT/IL2010/000549.
An International Search Report dated Oct. 6, 2011, which issued during the prosecution of Applicant's PCT/IL2010/000999.
An International Search Report dated Mar. 10, 2011, which issued during the prosecution of Applicant's PCT/IL2010/000917.
An International Search Report dated Mar. 30, 2011, which issued during the prosecution of Applicant's PCT/IL2010/001018.
An International Search Report dated Apr. 18, 2011, which issued during the prosecution of Applicant's PCT/IL2010/001037.
An International Search Report dated Jul. 7, 2011, which issued during the prosecution of Applicant's PCT/IL2010/001087.
An International Search Report dated Aug. 11, 2011, which issued during the prosecution of Applicant's PCT/IL2011/000135.
An International Search Report dated Jun. 30, 2009, which issued during the prosecution of Applicant's PCT/IL2008/001621.
A Written Opinion dated Jun. 30, 2009, which issued during the prosecution of Applicant's PCT/IL2008/001621.
An International Search Report dated Mar. 11, 2009, which issued during the prosecution of Applicant's PCT/IL2007/001312.
A Written Opinion dated Mar. 11, 2009, which issued during the prosecution of Applicant's PCT/IL2007/001312.
An English translation of an Office Action dated Aug. 25, 2011, which issued during the prosecution of Chinese Patent Application No. 200880014919.9.
An Office Action dated Nov. 12, 2010, which issued during the prosecution of U.S. Appl. No. 12/447,684.
An Office Action dated Apr. 27, 2011, which issued during the prosecution of U.S. Appl. No. 12/447,684.
An Office Action dated Feb. 25, 2013, which issued during the prosecution of U.S. Appl. No. 13/031,871.
An Office Action dated Feb. 27, 2013, which issued during the prosecution of U.S. Appl. No. 12/808.037.
An Extended European Search Report dated Dec. 13, 2012, which issued during the prosecution of Applicant's European App No. 08719912.1.
An International Search Report together with Written Opinion both dated Sep. 6, 2012, which issued during the prosecution of Applicant's PCT/IL2012/000190.
An International Search Report together with Written Opinion both dated Aug. 31, 2012, which issued during the prosecution of Applicant's PCT/IL2012/000148.
An Office Action dated Oct. 11, 2012, which issued during the prosecution of U.S. Appl. No. 13/031,871.
An Office Action dated Jun. 19, 2012, which issued during the prosecution of U.S. Appl. No. 12/808,037.
An International Search Report together with Written Opinion both dated Sep. 24, 2012, which issued during the prosecution of Applicant's PCT/IL2012/000060.
An International Search Report together with Written Opinion both dated Oct. 1, 2012, which issued during the prosecution of Applicant's PCT/IL2012/000241.
An International Search Report together with Written Opinion both dated Oct. 4, 2012, which issued during the prosecution of Applicant's PCT/IL2012/000269.
An International Search Report together with Written Opinion both dated Nov. 27, 2012, which issued during the prosecution of Applicant's PCT/IL2012/000300.
U.S. Appl. No. 61/264,861, filed Nov. 30, 2009.
An Office Action dated Jun. 18, 2013, which issued during the prosecution of U.S. Appl. No. 13/512,778.
An Office Action dated Feb. 28, 2014, which issued during the prosecution of U.S. Appl. No. 13/512,778.
An Interview Summary dated Sep. 25, 2014, which issued during the prosecution of U.S. Appl. No. 13/512,778.
An Interview Summary dated Apr. 24, 2014, which issued during the prosecution of U.S. Appl. No. 13/512,778.

(56) References Cited

OTHER PUBLICATIONS

An Office Action dated Aug. 15, 2014, which issued during the prosecution of U.S. Appl. No. 13/512,778.
Notice of Allowance dated Oct. 8, 2014, which issued during the prosecution of U.S. Appl. No. 13/512,778.
Notice of Allowance dated Nov. 7, 2014, which issued during the prosecution of U.S. Appl. No. 13/512,778.
An English Translation of an Office Action dated Jan. 16, 2015, which issued during the prosecution of Chinese Patent Application No. 201080062714.5. (the relevant part only).
An Office Action dated Feb. 5, 2015, which issued during the prosecution of U.S. Appl. No. 13/384,075.
An Office Action dated Feb. 23, 2015, which issued during the prosecution of U.S. Appl. No. 13/513,397.
European Search Report dated Feb. 26, 2015, which issued during the prosecution of Applicant's European App No. 12806964.8.
An International Search Report and a Written Opinion both dated Mar. 18, 2015, which issued during the prosecution of Applicant's PCT/IL2014/050973.
An English translation of an Office Action dated Mar. 19, 2015, which issued during the prosecution of Chinese Patent Application No. 201080036970.7.
An Office Action dated Feb. 3, 2015, which issued during the prosecution of U.S. Appl. No. 12/447,684.
Notice of Allowance dated Dec. 19, 2014, which issued during the prosecution of U.S. Appl. No. 13/512,778.
An Office Action dated Mar. 26, 2015, which issued during the prosecution of U.S. Appl. No. 13/514,240.
European Search Report dated Mar. 20, 2015, which issued during the prosecution of Applicant's European App No. 08861980.4.
An Office Action dated Jul. 30, 2015, which issued during the prosecution of U.S. Appl. No. 14/240,600.
An Office Action dated Aug. 12, 2015, which issued during the prosecution of U.S. Appl. No. 13/513,397.
An International Search Report and a Written Opinion both dated Jul. 30, 2014, which issued during the prosecution of Applicant's PCT/IL2014/050174.
European Search Report dated Jun. 12, 2014, which issued during the prosecution of Applicant's European App No. 12855964.8.
An Office Action dated Sep. 11, 2015, which issued during the prosecution of U.S. Appl. No. 14/001,641.
An Office Action dated Sep. 23, 2015, which issued during the prosecution of U.S. Appl. No. 13/384,075.
An Office Action dated Oct. 2, 2015, which issued during the prosecution of U.S. Appl. No. 13/577,161.
An Office Action dated May 15, 2015, which issued during the prosecution of U.S. Appl. No. 13/577.161.
An Office Action dated May 28, 2015, which issued during the prosecution of U.S. Appl. No. 14/240,600.
European Search Report dated Apr. 22, 2015, which issued during the prosecution of Applicant's European App No. 12828495.7.
An Office Action dated Apr. 14, 2015, which issued during the prosecution of U.S. Appl. No. 14/130,213.
Invitation to Pay Additional Fees dated May 13, 2014, which issued during the prosecution of Applicant's PCT/IL2014/050019.
Invitation to Pay Additional Fees dated May 8, 2014, which issued during the prosecution of Applicant's PCT/IL2014/050174.
An Advisory Action dated Feb. 13, 2014, which issued during the prosecution of U.S. Appl. No. 13/807,880.
An Office Action dated Apr. 28, 2014, which issued during the prosecution of U.S. Appl. No. 13/939,798.
An Office Action dated Apr. 24, 2014, which issued during the prosecution of U.S. Appl. No. 13/380,278.
An Office Action dated Apr. 10, 2014, which issued during the prosecution of U.S. Appl. No. 13/807,906.
An English translation of an Office Action dated Jan. 28, 2014, which issued during the prosecution of Chinese Patent Application No. 201080036970.7.
European Search Report dated Feb. 17, 2014, which issued during the prosecution of Applicant's European App No. 12803376.
An Office Action dated Jul. 24, 2014, which issued during the prosecution of Canadian Patent Application No. 2,768,228.
An International Search Report and a Written Opinion both dated Feb. 17, 2016, which issued during the prosecution of Applicant's PCT/IL2015/051221.
Scurr, James; McWilliams, Richard. Fenestrated Aortic Stent Grafts. Seminars in Interventional Radiology vol. 24, No. 2. (2007).
European Search Report dated May 23, 2016, which issued during the prosecution of Applicant's European App No. 10832752.9.
An Office Action dated Mar. 28, 2016, which issued during the prosecution of U.S. Appl. No. 14/362,194.
An Office Action together with the English translation dated Jul. 22, 2016, which issued during the prosecution of Chinese Patent Application No. 201480012648.9.
An Office Action together dated Sep. 15, 2016, which issued during the prosecution of Canadian Patent Application No. 2,782,357.
European Search Report dated Aug. 31, 2016, which issued during the prosecution of Applicant's European App No. 14762507.3.
European Search Report dated Sep. 22, 2016, which issued during the prosecution of Applicant's European App No. 10834308.8.
European Search Report dated Oct. 27, 2016, which issued during the prosecution of Applicant's European App No. 14801036.6.
Notice of Allowance dated Nov. 10, 2016, which issued during the prosecution of U.S. Appl. No. 14/362,194.
An Office Action dated Jul. 7, 2017, which issued during the prosecution of U.S. Appl. No. 14/572,156.
Aortic Aneurysm O'Gara, Patrick T. Circulation. 2003; 107:e43-e45.
An Office Action dated Jan. 12, 2017, which issued during the prosecution of U.S. Appl. No. 14/518.542.
An International Search Report and a Written Opinion both dated Jan. 19, 2017, which issued during the prosecution of Applicant's PCT/IL2016/051207.
European Search Report dated Jan. 18, 2016 which issued during the prosecution of Applicant's European App No. 10799521.9.
European Search Report dated Oct. 27, 2015 which issued during the prosecution of Applicant's European App No. 10835608.0.
An Office Action dated Dec. 7, 2016, which issued during the prosecution of U.S. Appl. No. 14/400,699.
An Office Action dated Feb. 23, 2018, which issued during the prosecution of U.S. Appl. No. 14/572,156.
Notice of Allowance dated Feb. 9, 2017, which issued during the prosecution of U.S. Appl. No. 14/772,016.
An Office Action dated Mar. 6, 2017, which issued during the prosecution of U.S. Appl. No. 13/979,551.
An Office Action dated Jul. 17, 2017, which issued during the prosecution of U.S. Appl. No. 14/759,736.
An Office Action dated May 26, 2017, which issued during the prosecution of Canadian Patent Application No. 2,782.357.
An Office Action dated Jan. 23, 2018, which issued during the prosecution of U.S. Appl. No. 14/893,201.
An Office Action dated Dec. 27, 2016, which issued during the prosecution of Chinese Patent Application No. 201510685240.4.

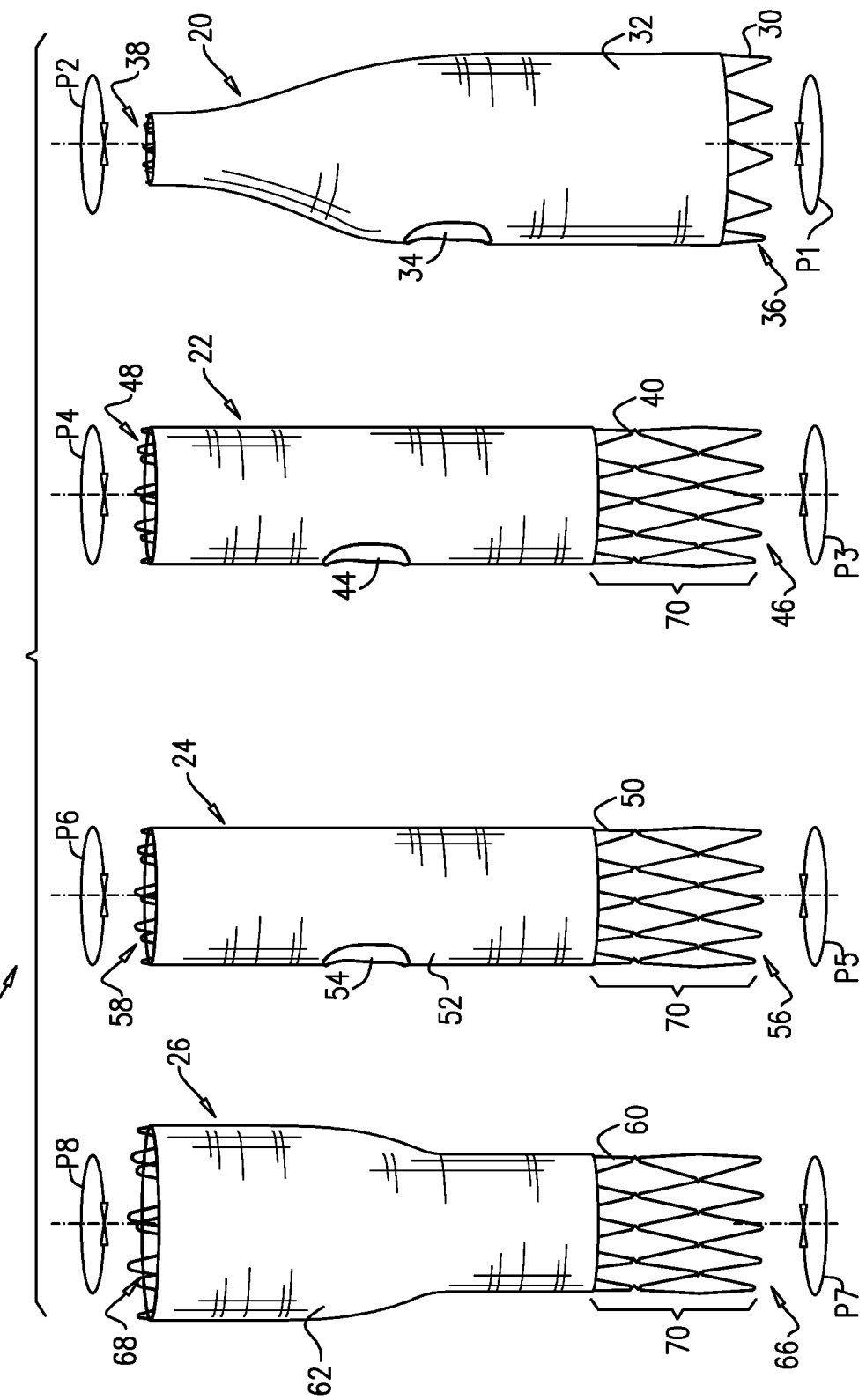

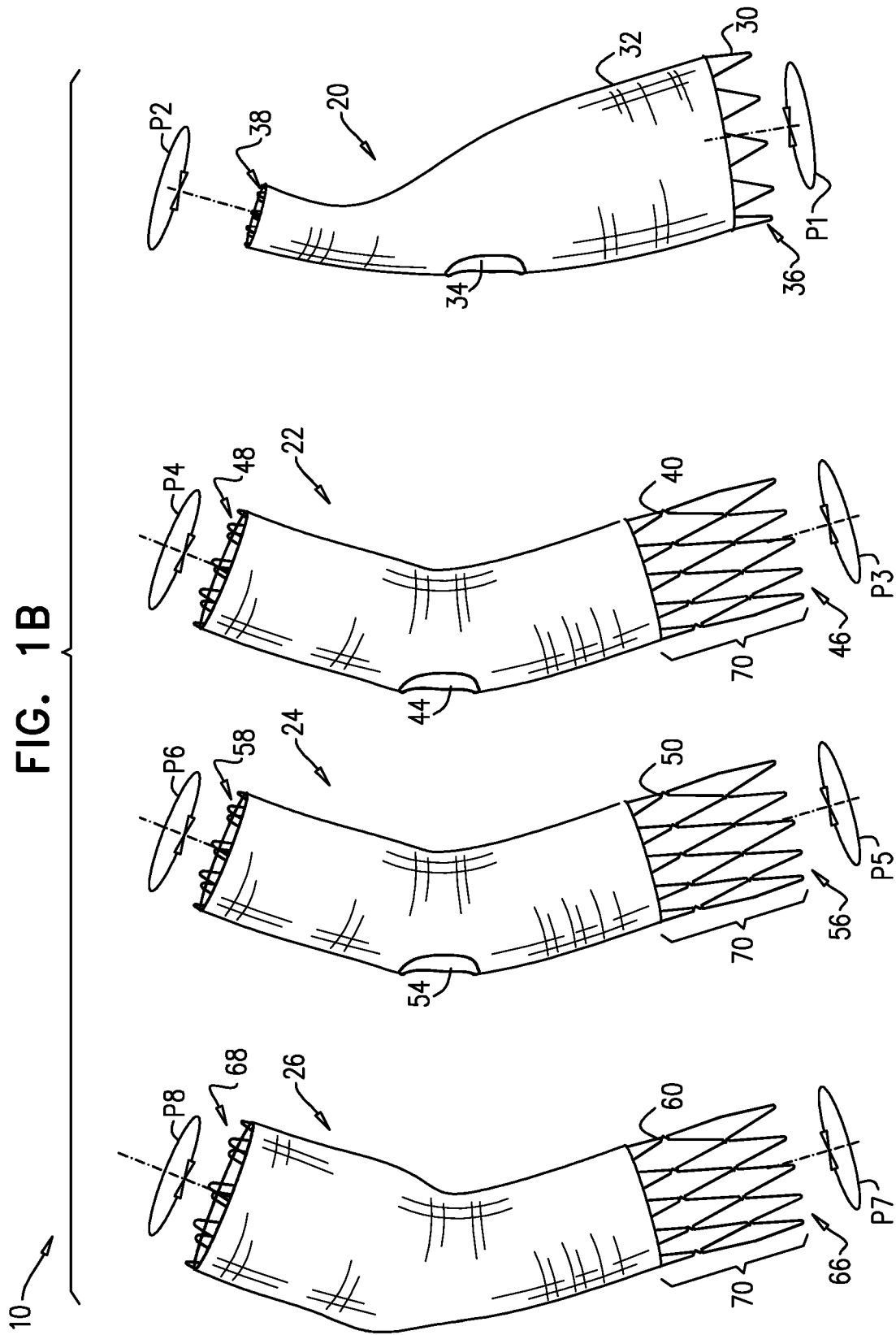

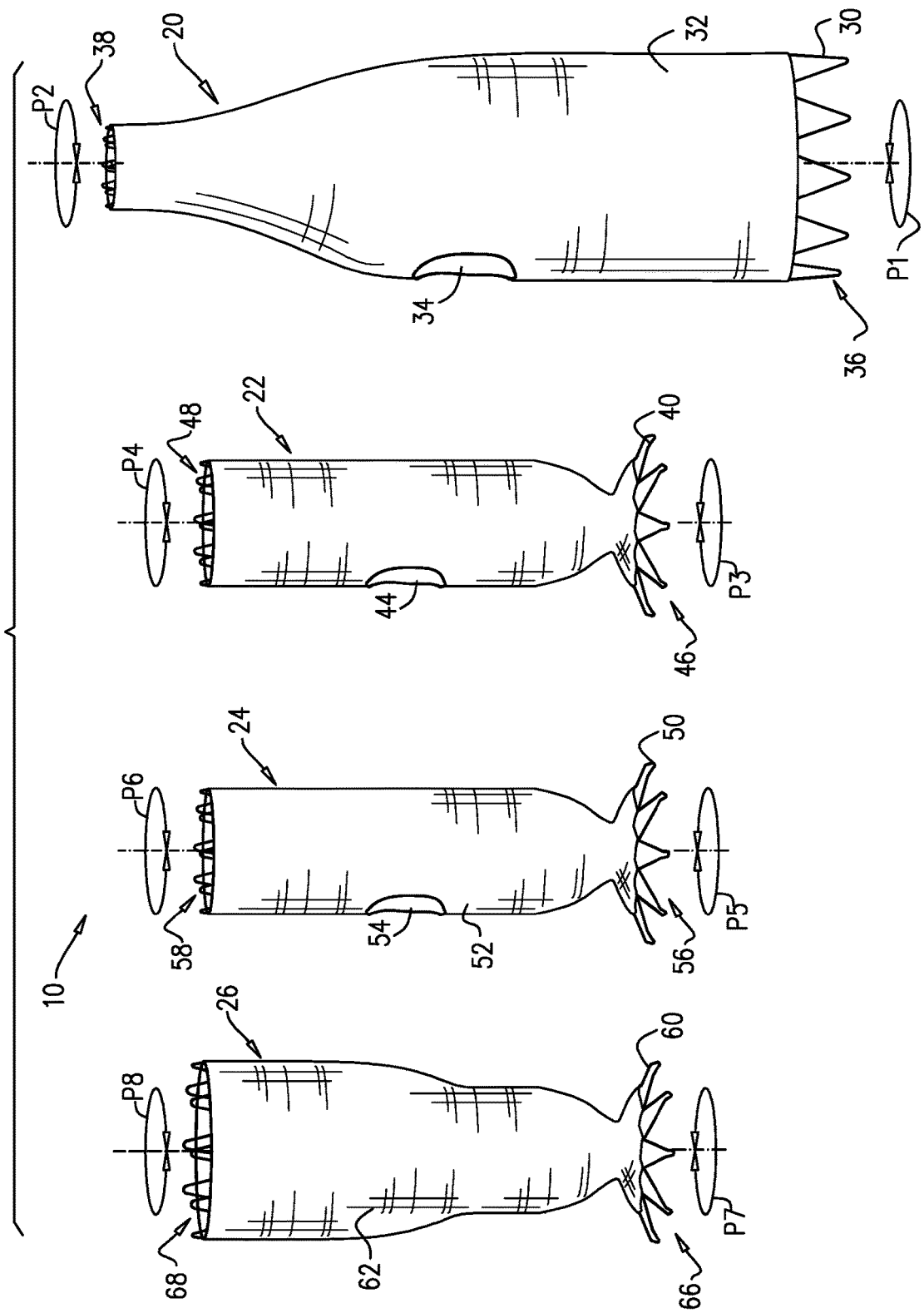

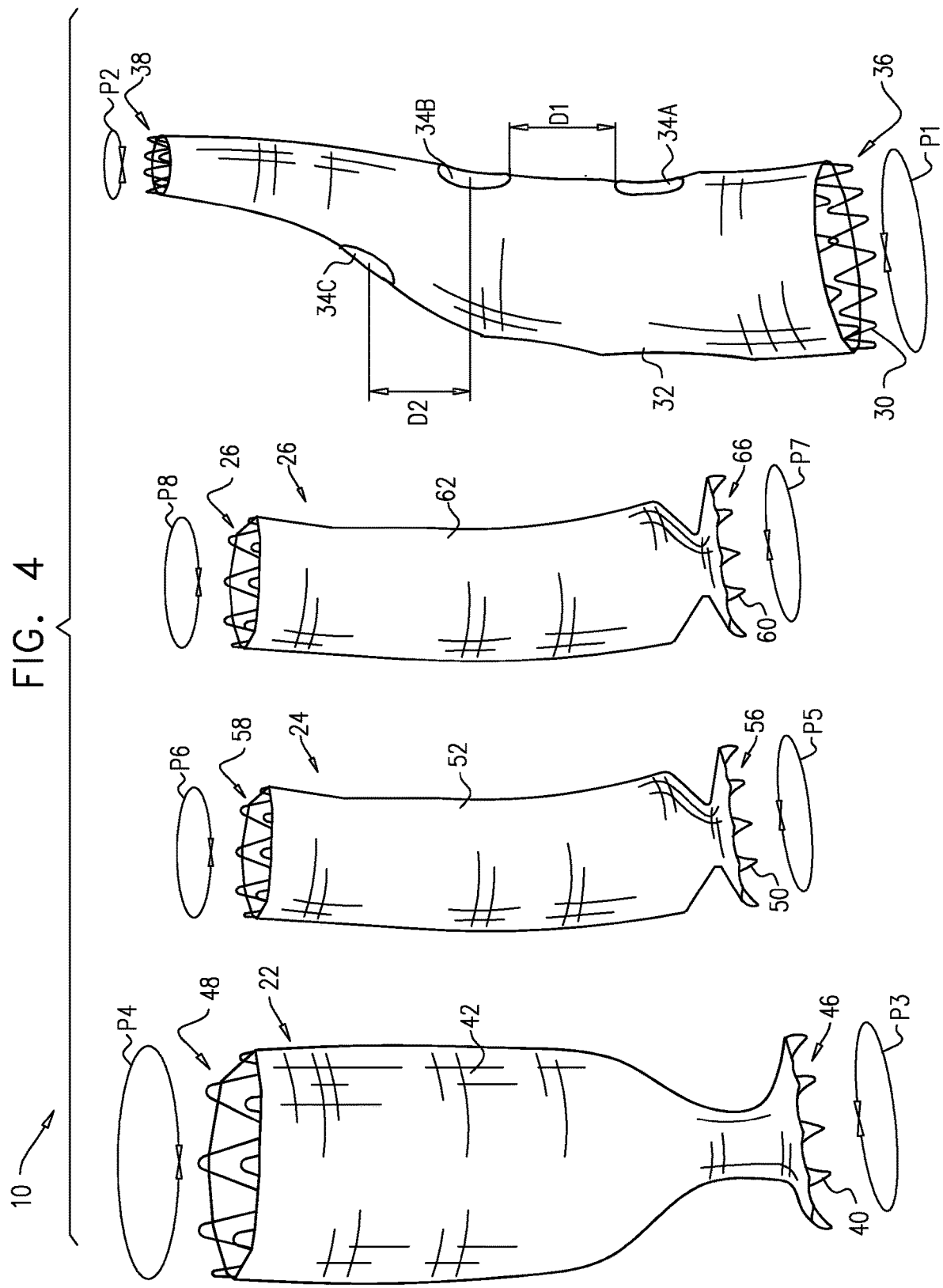

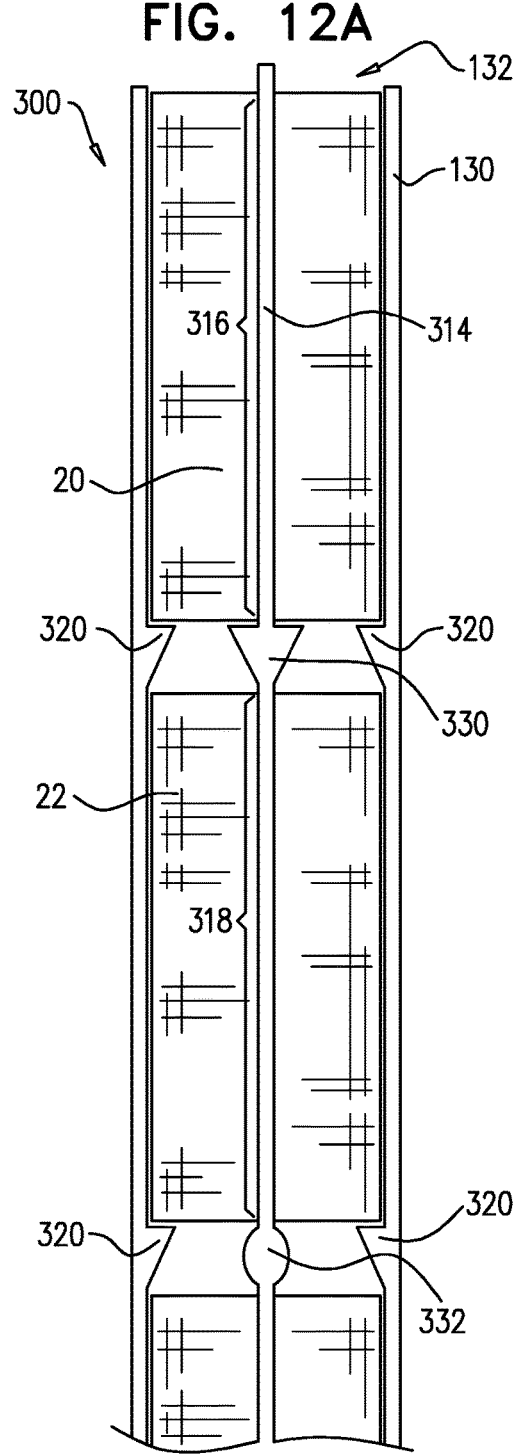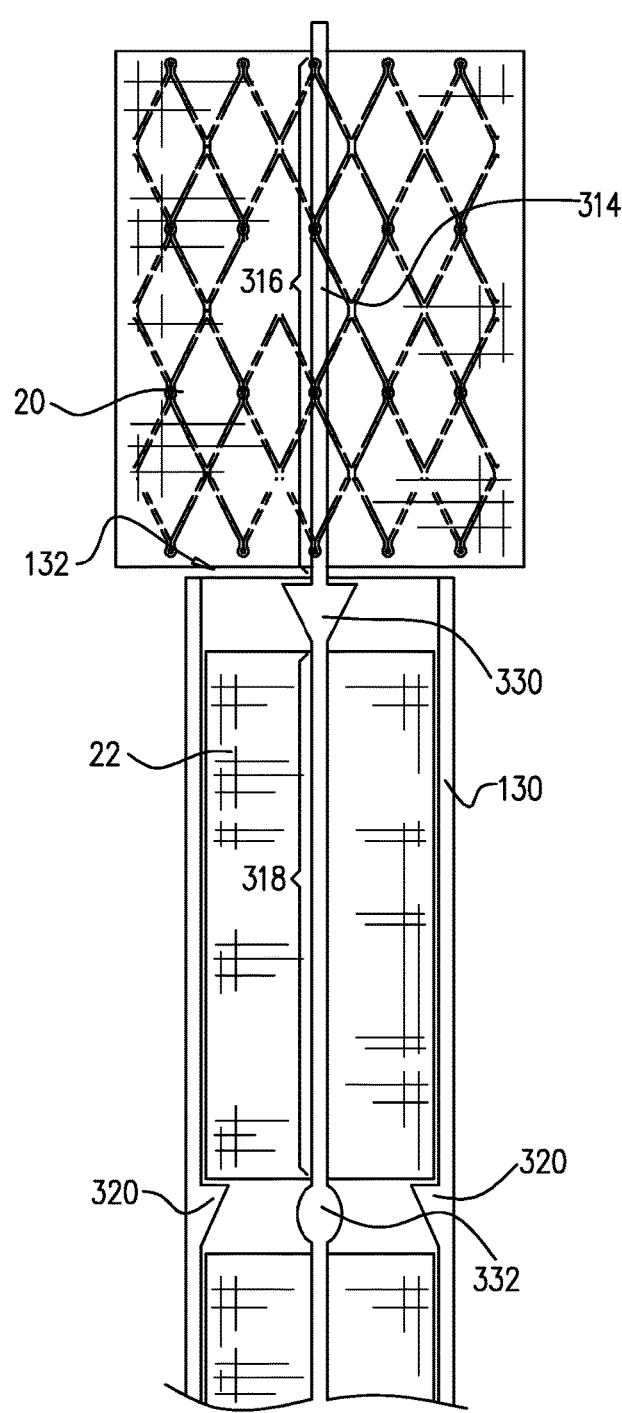

MULTI-COMPONENT STENT-GRAFT SYSTEM FOR IMPLANTATION IN A BLOOD VESSEL WITH MULTIPLE BRANCHES

CROSS-REFERENCE TO RELATED APPLICATIONS

The present patent application is a continuation of U.S. application Ser. No. 14/572,156, filed Dec. 16, 2014, now U.S. Pat. No. 10,201,413, which is a continuation of U.S. application Ser. No. 13/512,778, filed Sep. 24, 2012, now U.S. Pat. No. 8,945,203, which is the U.S. national stage of International Application PCT/IL2010/000999, filed Nov. 30, 2010, which claims priority from U.S. Provisional Application 61/264,861, filed Nov. 30, 2009, entitled, "A multi component stent graft system for implantation into a vessel with multiple adjacent branches and methods for using same," which is incorporated herein by reference.

FIELD OF THE APPLICATION

This present application relates generally to prostheses and surgical methods, and specifically to tubular prostheses, including endovascular grafts and stent-grafts, and surgical techniques for using the prostheses to maintain patency of body passages such as blood vessels, and treating aneurysms.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery.

Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs") and aortic uni-iliac ("AUI") aneurysms.

PCT Publication WO 2008/107885 to Shalev et al., and US Patent Application Publication 2010/0063575 to Shalev et al. in the US national stage thereof, which are incorporated herein by reference, describe a multiple-component expandable endoluminal system for treating a lesion at a bifurcation, including a self expandable tubular root member having a side-looking engagement aperture, and a self expandable tubular trunk member comprising a substantially blood impervious polymeric liner secured therealong. Both have a radially-compressed state adapted for percutaneous intraluminal delivery and a radially-expanded state adapted for endoluminal support.

U.S. Patent Application Publication 2009/0254170 to Hartley et al. describes a deployment system for introducing stent grafts which have a side arm or into which a side arm can be deployed. For instance the stent graft can be deployed into the thoracic arch of a patient. The deployment system includes an introducer, an auxiliary catheter disposed within the introducer and an auxiliary guide wire disposed within the auxiliary catheter. The auxiliary guide wire extends to adjacent the proximal end of the introducer an can be extended from the proximal end of the introducer so that it can be snared from a side branch artery to assist with deployment of a side arm of the stent graft into the side artery or for the deployment of a side arm stent graft into the stent graft.

The following references may be of interest:

U.S. Pat. No. 4,938,740 to Melbin
U.S. Pat. No. 5,824,040 to Cox et al.
U.S. Pat. No. 7,044,962 to Elliott
U.S. Patent Application Publication 2004/0106978 to Greenberg et al.
U.S. Patent Application Publication 2006/0229709 to Morris et al.
U.S. Patent Application Publication 2006/0241740 to Vardi et al.
U.S. Patent Application Publication 2007/0233229 to Berra et al.
U.S. Patent Application Publication 2008/0109066 to Quinn
U.S. Patent Application Publication 2008/0114445 to Melsheimer et al.
U.S. Patent Application Publication 2010/0161026 to Brocker et al.
PCT Publication WO 2004/017868 to Hartley
PCT Publication WO 2006/007389 to Greenberg et al.
PCT Publication WO 2007/084547 to Godlewski et al.
PCT Publication WO 2008/042266 to Yi Tseng et al.
PCT Publication WO 2008/047092 to Goddard et al.
PCT Publication WO 2008/140796 to Hartley et al.
PCT Publication WO 2010/024869 to Hartley et al.
PCT Publication WO 2010/024879 to Hartley et al.
PCT Publication WO 2010/062355 to Kolbel et al.
European Publication EP 1 177 780 A2 to Barone
European Publication EP 1 325 716 A1 to Depalma et al.
Canadian Publication CA 2 497 704 to Nelson

SUMMARY OF APPLICATIONS

Some applications of the present invention provide a multi-component stent-graft system for treating a thoracic aortic aneurysm, such as of the aortic arch. The system is configured to be deployed in the thoracic aorta and in one or more of the branches of the aortic arch (the brachiocephalic artery, the left common carotid artery, and/or the left subclavian artery). The multi-component stent-graft comprises first and second stent-grafts, and optionally a third stent-graft and/or a fourth stent-graft. Typically, the first stent-graft is shaped so as to define at least one first lateral opening. The second stent-graft is typically configured to be disposed through the first lateral opening, such that the second stent-graft forms a blood-impervious seal with the first stent-graft around the first lateral opening.

The multi-component stent-graft system is configured to be deployed in a straightforward procedure that readily accommodates ordinary anatomical variances among different patients. For example, the locations of the bifurcations of the three branches of the aortic arch vary among patients. The stent-grafts of the system are assembled in situ to accommodate the dimensions of the particular patient's anatomy, generally without requiring prior customization of the stent-grafts or in situ modifications to the stent-grafts, which might be expensive and/or complex.

Typically, upon deployment, the multi-component stent-graft system defines a blood-flow path from the ascending aorta, over the aortic arch, and to the descending aorta. The stent-graft system additionally provides blood-flow paths to the three branches of the aortic arch.

For some applications, the first stent-graft is configured to be positioned such that a proximal portion thereof, including a proximal end thereof, is positioned in the upper part of the descending aorta, and a distal portion thereof, including a distal end thereof, is positioned in one of the branches of the aortic arch. When thus positioned, the first lateral opening is disposed in the aortic arch facing upstream, generally toward the ascending aorta.

For some applications, the distal portion of the first stent-graft is positioned in the left subclavian artery. The second stent-graft is advanced up the descending aorta, through the proximal portion of the first-stent-graft, out of the first lateral opening, and into a second one of the branches of the aortic arch, such as the left common carotid artery. A proximal portion of the second stent-graft, including a proximal end thereof, is positioned within the first stent-graft in the upper part of the descending aorta, and a distal portion of the second stent-graft, including a distal end thereof, is positioned in the left common carotid artery. It is noted that this technique for positioning the second stent-graft readily accommodates the particular anatomical location of the second branch of the aortic arch (including with respect to the first branch), without requiring either the first or the second stent-graft to be customized (in shape or size) for the particular patient.

For some applications in which the third stent-graft is provided, the second stent-graft is shaped so as to define a second lateral opening, which faces upstream, generally toward the ascending aorta, upon placement of the second stent-graft as described above. The third stent-graft is advanced up the descending aorta and into a third one of the branches of the aortic arch, such as the brachiocephalic artery. A proximal portion of the third stent-graft is positioned within the second stent-graft in the aortic arch, and a distal portion of the third stent-graft, including a distal end thereof, is positioned in the brachiocephalic artery. It is noted that this technique for positioning the third stent-graft readily accommodates the particular anatomical location of the third branch of the aortic arch (including with respect to the first and second branches), without requiring either the first, second, or third stent-graft to be customized (in shape or size) for the particular patient.

For some applications in which the fourth stent-graft is provided, the third stent-graft is shaped so as to define a third lateral opening, which faces upstream, generally toward the ascending aorta, upon placement of the third stent-graft as described above. The fourth stent-graft is advanced up the descending aorta and into the aortic arch and/or the upper part of the ascending aorta. A proximal portion of the fourth stent-graft is positioned within the third stent-graft in the aortic arch, and a distal portion of the fourth stent-graft, including a distal end thereof, is positioned in the aortic arch and/or the upper part of the ascending aorta.

For other applications, the first stent-graft is shaped so as to define proximal and distal superior first lateral openings, and a distal inferior first lateral opening. A proximal portion of the first stent-graft, including a proximal end thereof, is positioned in the upper part of the descending aorta; a middle portion of the first stent-graft is positioned in the aortic arch; and a distal portion of the first stent-graft, including a distal end thereof, is positioned in the brachiocephalic artery. The proximal superior first lateral opening faces toward and is aligned with the left subclavian artery, and the distal superior first lateral opening faces toward and is aligned with the left common carotid artery. The distal inferior first lateral opening is disposed within the aortic arch facing upstream, generally toward the ascending aorta. It is noted that the distance between the bifurcations of the left common carotid artery and the left subclavian artery does not generally vary substantially among patients, so the generally fixed relative locations of the proximal and distal superior first lateral openings does not generally present difficulties during the procedure, particularly if some space is provided between the superior openings and the bifurcations to allow manipulation of third and fourth stent-grafts, described below. The two openings are readily aligned with the two branches during positioning of the first stent-graft, such that placement of the distal end of the first stent-graft in the brachiocephalic artery naturally accommodates the location of the bifurcation of the brachiocephalic artery with respect to the locations of the bifurcations of the left common carotid artery and the left subclavian artery.

The second stent-graft is advanced up the descending aorta, through a proximal portion of the first-stent-graft, out of the distal inferior first lateral opening, and into the aortic arch and/or the upper part of the ascending aorta. A proximal portion of the second stent-graft, including a proximal end thereof, is positioned within the first stent-graft in the aortic arch, and a distal portion of the second stent-graft, including a distal end thereof, is positioned in the aortic arch and/or the upper part of the ascending aorta.

The third and fourth stent-grafts are separately advanced up the descending aorta (in a single delivery tool, or two separate delivery tools) and through a proximal portion of the first stent-graft. One of these stent-grafts is advanced out of the proximal superior first lateral opening into the left subclavian artery, and the other is advanced out of the distal superior first lateral opening into the left common carotid artery. Proximal portions of the third and fourth stent-grafts, including proximal ends thereof, are positioned within the first stent-graft in the aortic arch, and distal portions of the third and fourth stent-grafts, including distal ends thereof, are positioned in the left subclavian artery and the left common carotid artery, respectively.

For still other applications, the first stent-graft is shaped so as to define a superior first lateral opening and an inferior first lateral opening. A proximal portion of the first stent-graft, including a proximal end thereof, is positioned in the upper part of the descending aorta; a middle portion of the first stent-graft is positioned in the aortic arch; and a distal portion of the first stent-graft, including a distal end thereof, is positioned in the left common carotid artery. The superior first lateral opening faces toward and is aligned with the left subclavian artery, and the inferior first lateral opening is disposed within the aortic arch facing upstream, generally toward the ascending aorta. It is noted that this technique for positioning the first stent-graft readily accommodates the particular anatomical location of the left common carotid artery.

The second stent-graft is advanced up the descending aorta, through a proximal portion of the first-stent-graft, out of the superior first lateral opening, and into the left subclavian artery. A proximal portion of the second stent-graft, including a proximal end thereof, is positioned within the first stent-graft in the aortic arch, and a distal portion of the second stent-graft, including a distal end thereof, is positioned in the left subclavian artery. It is noted that this technique for positioning the second stent-graft readily accommodates the particular anatomical location of the left common carotid artery.

The third stent-graft is advanced down the right subclavian artery and the brachiocephalic artery into the upper part of the ascending aorta. A proximal portion of the third stent-graft, including a proximal end thereof, is positioned within the brachiocephalic artery, and a distal portion of the third stent-graft, including a distal end thereof, is positioned in the aortic arch and/or the upper part of the ascending aorta. A third lateral opening defined by the third stent-graft is disposed within the aortic arch facing downstream, generally toward the descending aorta, such that the third lateral opening faces and is aligned with the inferior first lateral opening of the first stent-graft. It is noted that this technique for positioning the third stent-graft readily accommodates the particular anatomical location of the brachiocephalic artery with respect to the left subclavian artery and the left common carotid artery.

The fourth stent-graft is advanced up the descending aorta, through a proximal portion of the first stent-graft, and out of the inferior first lateral opening. A distal portion of the fourth stent-graft, including a distal end thereof, is positioned within the first stent-graft; a proximal portion of the fourth stent-graft, including a proximal end thereof, is positioned within the third stent-graft; and a middle portion of the fourth stent-graft is positioned in the aortic arch.

Although the multi-component stent-graft system is generally described herein as being applicable for placement in the area of the thoracic aorta, for some applications the stent-graft system is instead placed in another area of a main body lumen and one or more branching body lumens, such as a main blood vessel and one or more branching blood vessels. For some applications, a method for deploying the stent-graft system comprises transvascularly introducing and positioning a first stent-graft such that a proximal portion of the first stent-graft, including a proximal end of the first-stent-graft, is in a proximal portion of a main blood vessel, a distal portion of the first stent-graft, including a distal end of the first stent-graft, is in a branching blood vessel that branches from the main blood vessel, and a first lateral opening defined by the first stent-graft is disposed within the main blood vessel facing toward a distal portion of the main blood vessel; and transvascularly introducing and passing a second stent-graft through the proximal portion of the first stent-graft such that the second stent-graft is disposed through the first lateral opening and is disposed partially in the distal portion of the main blood vessel, and forms a blood-impervious seal with the first stent-graft around the first lateral opening.

There is therefore provided, in accordance with an application of the present invention, apparatus including a multi-component stent-graft system, which includes:

a first generally tubular stent-graft, which is shaped so as to define a first lateral opening when in a radially-expanded state;

a second generally tubular stent-graft, which is shaped so as to define a second lateral opening when in a radially-expanded state, wherein the first and second stent-grafts are configured such that the second stent-graft forms a blood-impervious seal with the first stent-graft around the first lateral opening when the second stent-graft is disposed therethrough, and the first and the second stent-grafts are in their radially-expanded states; and a third generally tubular stent-graft, which is configured to assume a radially-expanded state, wherein the second and the third stent-grafts are configured such that the third stent-graft forms a blood-impervious seal with the second stent-graft around the second lateral opening when the third stent-graft is disposed therethrough, and the second and third stent-grafts are in their radially-expanded states.

For some applications:

the first stent-graft includes a first generally tubular support element and a first covering element attached to the first support element so as to at least partially cover the first support element, and the first covering element and the first support element are shaped so as to together define the first lateral opening through the first stent-graft when the first stent-graft is in its radially-expanded state, the second stent-graft includes a second generally tubular support element and a second covering element attached to the second support element so as to at least partially cover the second support element, and the second covering element and the second support element are shaped so as to together define the second lateral opening through the second stent-graft when the second stent-graft is in its radially-expanded state, and the first and the second stent-grafts are configured such that the second covering element forms the blood-impervious seal with the first covering element around the first lateral opening when the second stent-graft is disposed therethrough, and the first and the second stent-grafts are in their radially-expanded states, and the third stent-graft includes a third generally tubular support element and a third covering element attached to the third support element so as to at least partially cover the third support element, and the second and the third stent-grafts are configured such that the third covering element forms the blood-impervious seal with the second covering element around the second lateral opening when the third stent-graft is disposed therethrough, and the second and third stent-grafts are in their radially-expanded states.

For some applications, the first, the second, and the third covering elements are not fixed to one another when the first, the second, and the third stent-grafts are in their radially-compressed states. For some applications, when the third stent-graft is disposed through the second lateral opening and the second and the third stent-grafts are in their radially-expanded states: a proximal portion of the third support element is disposed within the second stent-graft, and the third covering element does not fully cover the proximal portion of the third support element, thereby allowing blood flow through the second stent-graft.

For some applications, the second stent-graft is configured to transition, without inverting, from a radially-compressed state to its radially-expanded state. For some applications, the third stent-graft is configured to transition, without inverting, from a radially-compressed state to its radially-expanded state.

For some applications, the first, the second, and the third stent-grafts are not fixed to one other when in their radially-compressed states.

For some applications, the third stent-graft is adapted for transluminal delivery in a radially-compressed state through, sequentially, (a) a portion of the first stent-graft, (b) the first lateral opening, (c) a portion of the second stent-graft, and (d) the second lateral opening, while the first and the second stent-grafts are in their radially-expanded states.

For some applications, the third stent-graft is shaped so as to define a third lateral opening when in its radially-expanded state; the stent-graft system further includes a fourth generally tubular stent-graft, which is configured to assume a radially-expanded state; and the third and the fourth stent-grafts are configured such that the fourth stent-graft forms a blood-impervious seal with the third stent-graft around the third lateral opening when the fourth stent-graft is disposed therethrough, and the third and the fourth stent-grafts are in their radially-expanded states.

For some applications:

the third covering element and the third support element are shaped so as to together define the third lateral opening through the third stent-graft when the third stent-graft is in its radially-expanded state, the fourth stent-graft includes a fourth generally tubular support element and a fourth covering element, which is attached to the fourth support element so as to at least partially cover the fourth support element, and the third and the fourth stent-grafts are configured such that the fourth covering element forms the blood-impervious seal with the third covering element around the third lateral opening when the fourth stent-graft is disposed therethrough, and the third and the fourth stent-grafts are in their radially-expanded states.

For some applications, the fourth covering element and the fourth support element are not shaped so as to together define any lateral openings through the fourth stent-graft when the fourth stent-graft is in its radially-expanded state.

For some applications, the first, the second, the third, and the fourth stent-grafts are configured for transluminal delivery for transport to respective sites within a body lumen when in radially-compressed states, and the fourth stent-graft is adapted for transluminal delivery in its radially-compressed state through, sequentially, (a) a portion of the first stent-graft, (b) the first lateral opening, (c) a portion of the second stent-graft, (d) the second lateral opening, (e) a portion of the third stent-graft, and (f) the third lateral opening, while the first, the second, and the third stent-grafts are in their radially-expanded states.

For some applications, (a) a proximal portion of the first stent-graft, including a proximal end of the first-stent-graft, is configured to be positioned in a proximal portion of a main blood vessel, (b) a distal portion of the first stent-graft, including a distal end of the first stent-graft, is configured to be positioned in a branching blood vessel that branches from the main blood vessel, and (c) the first stent-graft is configured such that a first lateral opening defined by the first stent-graft is disposed within the main blood vessel facing toward a distal portion of the main blood vessel; and the second stent-graft is configured to be disposed partially in the distal portion of the main blood vessel.

For some applications, the first stent-graft is shaped so as to define exactly one first lateral opening when the first stent-graft is in its radially-expanded state.

There is further provided, in accordance with an application of the present invention, apparatus including a multi-component stent-graft system, which includes:

a first generally tubular stent-graft, which, when unconstrained in a radially-expanded state: (a) defines a first lateral opening, and (b) has a first perimeter of a first end thereof that equals at least 200% of a second perimeter of a second end thereof; and a second generally tubular stent-graft, which is configured to assume a radially-expanded state, wherein the first and the second stent-grafts are configured such that the second stent-graft forms a blood-impervious seal with the first stent-graft around the first lateral opening when the second stent-graft is disposed therethrough, and the first and second stent-grafts are in their radially-expanded states.

For some applications:

the first stent-graft includes a first generally tubular support element and a first covering element attached to the first support element so as to at least partially cover the first support element, and the first covering element and the first support element are shaped so as to together define the first lateral opening through the first stent-graft when the first stent-graft is in its radially-expanded state, and the second stent-graft includes a second generally tubular support element and a second covering element attached to the second support element so as to at least partially cover the second support element, and the first and the second stent-grafts are configured such that the second covering element forms the blood-impervious seal with the first covering element around the first lateral opening when the second stent-graft is disposed therethrough, and the first and the second stent-grafts are in their radially-expanded states.

For some applications, the first perimeter equals at least 250% of the second perimeter, such as at least 400% of the second perimeter. For some applications, the first perimeter is between 2.5 and 4.5 cm, and the second perimeter is between 1 and 1.5 cm.

For some applications, when the first stent-graft is unconstrained in its radially-expanded state, a perimeter of the first lateral opening is at least 40% of the first perimeter. For some applications, when the first stent-graft is unconstrained in its radially-expanded state, a perimeter of the first lateral opening is at least 60% of the second perimeter.

For some applications, the second stent-graft is configured to transition, without inverting, from a radially-compressed state to its radially-expanded state.

For some applications:

the first lateral opening includes a superior first lateral opening and an inferior first lateral opening, the first stent-graft is shaped so as to define the superior first lateral opening facing in a first radial direction, and the inferior first lateral opening facing a second radial direction generally opposite the first radial direction, and the first and the second stent-grafts are configured such that the second stent-graft forms the blood-impervious seal with the first stent-graft around one of the superior and inferior first lateral openings when the second stent-graft is disposed therethrough, and the first and second stent-grafts are in their radially-expanded states.

For some applications, the first and the second stent-grafts are configured such that the second stent-graft forms the blood-impervious seal with the first covering element around the superior first lateral opening when the second stent-graft is disposed therethrough, and the first and second stent-grafts are in their radially-expanded states.

For some applications, the first stent-graft is shaped so as to define exactly one first lateral opening when the first stent-graft is in its radially-expanded state.

There is still further provided, in accordance with an application of the present invention, apparatus including a multi-component stent-graft system, which includes:

a first stent-graft, which is shaped so as to define, when in a radially-expanded state, proximal and distal superior first lateral openings facing in a first radial direction, and a distal inferior first lateral opening facing a second radial direction generally opposite the first radial direction; and second, third, and fourth branching stent-grafts, which are configured assume radially-expanded states, wherein the first, the second, the third, and the fourth stent-grafts are configured such that the branching stent-grafts form respective blood-impervious seals with the first stent-graft around the distal inferior first lateral opening, the distal superior first lateral opening, and the proximal superior first lateral opening, respectively, when the branching stent-grafts are disposed therethrough, respectively, and the first, the second, the third, and the fourth stent-grafts are in their radially-expanded states.

For some applications:

the first stent-graft includes a first generally tubular support element and a first covering element attached to the first support element so as to at least partially cover the first support element, and the first covering element and the first support element are shaped so as to together define, when the first stent-graft is in its radially-expanded state, the proximal and the distal superior first lateral openings facing in the first radial direction, and the distal inferior first lateral opening facing the second radial direction, and the second, the third, and the fourth branching stent-grafts include respective generally tubular branching support elements and respective branching covering elements, attached to the branching support elements so as to at least partially cover the branching support elements, and the first, the second, the third, and the fourth stent-grafts are configured such that the branching covering elements form the respective blood-impervious seals with the first covering element around the distal inferior first lateral opening, the distal superior first lateral opening, and the proximal superior first lateral opening, respectively, when the branching stent-grafts are disposed therethrough, respectively, and the first, the second, the third, and the fourth stent-grafts are in their radially-expanded states.

For some applications, the distal inferior first lateral opening is not axially aligned with either of the proximal or distal superior first lateral openings. For some applications, the distal inferior first lateral opening does not axially overlap with either of the proximal or distal superior first lateral openings.

There is additionally provided, in accordance with an application of the present invention, apparatus including a multi-component stent-graft system, which includes:

a first stent-graft, which is shaped so as to define, when in a radially-expanded state, a superior first lateral opening facing in a first radial direction, and an inferior first lateral opening facing in a second radial direction generally opposite the first radial direction;

a second stent-graft, which is configured to assume a radially-expanded state, wherein the first and the second stent-grafts are configured such that the second stent-graft forms a blood-impervious seal with the first stent-graft around the superior first lateral opening when the second stent-graft is disposed therethrough, and the first and the second stent-grafts are in their radially-expanded states;

a third stent-graft, which is shaped so as to define a third lateral opening through the third stent-graft when the third stent-graft is in a radially-expanded state; and a fourth stent-graft having first and second ends, which stent-graft is configured to assume a radially-expanded state, wherein the first, the third, and the fourth stent-grafts are configured such that, when the first, the third, and the fourth stent-grafts are in their radially-expanded states, the fourth stent-graft forms blood-impervious seals with (a) the first stent-graft around the inferior first lateral opening when the first end of the fourth stent-graft is disposed therethrough, and (b) the third stent-graft around the third lateral opening when the second end of the fourth stent-graft is disposed therethrough.

For some applications:

the first stent-graft includes a first generally tubular support element and a first covering element attached to the first support element so as to at least partially cover the first support element, and the first covering element and the first support element are shaped so as to together define, when the first stent-graft is in its radially-expanded state, the superior first lateral opening facing in the first radial direction, and the inferior first lateral opening facing in the second radial direction, the second stent-graft includes a second generally tubular support element and a second covering element attached to the second support element so as to at least partially cover the second support element, and the first and the second stent-grafts are configured such that the second covering element forms the blood-impervious seal with the first covering element around the superior first lateral opening when the second stent-graft is disposed therethrough, and the first and the second stent-grafts are in their radially-expanded states, the third stent-graft includes a third generally tubular support element and a third covering element attached to the third support element so as to at least partially cover the third support element, and the third covering element and the third support element are shaped so as to together define the third lateral opening through the third stent-graft when the third stent-graft is in its radially-expanded state, and the fourth stent-graft includes a fourth generally tubular support element and a fourth covering element attached to the fourth support element so as to at least partially cover the fourth support element, and the first, the third, and the fourth stent-grafts are configured such that, when the first, the third, and the fourth stent-grafts are in their radially-expanded states, the fourth covering element forms the blood-impervious seals with (a) the first covering element around the inferior first lateral opening when the first end of the fourth stent-graft is disposed therethrough, and (b) the third covering element around the third lateral opening when the second end of the fourth stent-graft is disposed therethrough.

For some applications, the inferior first lateral opening is not axially aligned with the superior first lateral opening. For some applications, the inferior first lateral opening does not axially overlap with the superior first lateral opening.

There is yet additionally provided, in accordance with an application of the present invention, apparatus including a multi-component stent-graft system, which includes:

a first stent-graft, which is configured to assume radially-expanded and radially-compressed states;

a second stent-graft, which is configured to assume radially-expanded and radially-compressed states; and a delivery tool, which includes an outer tube, in which the first and the second stent-grafts are initially positioned at respective axial sites within the outer tube, in their radially-compressed states without being fixed to each other.

For some applications, the first and second stent-grafts are initially positioned in the outer tube such that at least one end of the first stent-graft is within a distance of a distal end of the outer tube, which distance equals the sum of 2 cm and an axial length of the first stent-graft; and the delivery tool is shaped so as to define first and second stopper elements, which are configured and initially positioned to prevent movement of the first and the second stent-grafts, respectively, in a proximal direction away from the distal end of the outer tube. For some applications, an inner surface of the outer tube is shaped so as to define the first and second stopper elements. For some applications, the delivery tool further includes an inner longitudinal member, which is initially positioned such that first and second portions thereof are within the first and the second stent-grafts, respectively, and the inner longitudinal member is shaped so as to define the first and the second stopper elements. For some applications, the inner longitudinal member is shaped so as to define a lumen therethrough.

For some applications:

the first and the second stent-grafts are initially positioned in the outer tube such that at least one end of the first stent-graft is within a distance of a distal end of the outer tube, which distance equals the sum of 2 cm and an axial length of the first stent-graft, the delivery tool further includes an inner longitudinal member, which is initially positioned such that first and second portions thereof are within the first and the second stent-grafts, respectively, and the inner longitudinal member is shaped so as to define a stopper element, which is:

configured and initially positioned to prevent movement of the first stent-graft in a proximal direction away from the distal end of the outer tube, and configured to be withdrawable in the proximal direction through the second stent-graft, and after being thus withdrawn, to prevent movement of the second stent-graft in the proximal direction.

For some applications, an inner surface of the outer tube is shaped so as to define at least one pusher element, which is configured to prevent movement of at least one of the first and the second stent-grafts in the proximal direction.

For some applications, the delivery tool further includes at least one pusher element, which is configured to prevent movement of at least one of the first and the second stent-grafts in the proximal direction.

For some applications, the inner longitudinal member is shaped so as to define a lumen therethrough.

For some applications, the first stent-graft is initially positioned in the outer tube such that at least one end of the first stent-graft is within a distance of a distal end of the outer tube, which distance equals the sum of 2 cm and an axial length of the first stent-graft, and the second stent-graft is initially positioned in the outer tube such that the first stent-graft is longitudinally between the distal end of the outer tube and the second stent-graft.

For some applications, the first stent-graft is shaped so as to define a first lateral opening. For some applications, the first stent-graft includes a first generally tubular support element and a first covering element, which is attached to the first support element so as to at least partially cover the first support element, and the first covering element and the first support element are shaped so as to together define the first lateral opening; the second stent-graft includes a second generally tubular support element and a second covering element, which is attached to the second support element so as to at least partially cover the second support element; and the first and the second stent-grafts are configured such that the second covering element forms a blood-impervious seal with the first covering element around the first lateral opening when the second stent-graft is disposed therethrough, and the first and the second stent-grafts are in their radially-expanded states.

For any of the applications described above, when the second stent-graft is disposed through the first lateral opening and the first and the second stent-grafts are in their radially-expanded states: a proximal portion of the second support element may be disposed within the first stent-graft, and the second covering element may not fully cover the proximal portion of the second support element, thereby allowing blood flow through the first stent-graft. For some applications, an axial portion of the proximal portion of the second support element having a length of at least 1 cm has a perimeter that is at least 10% greater than a perimeter of a portion of the first stent-graft in which the proximal portion of the second support element is disposed, when the first and second stent-grafts are in their radially-expanded states. For some applications, the second covering element is configured to cover a distal sub-portion, and not a proximal sub-portion, of the proximal portion of the second support element.

For any of the applications described above, a proximal end of the second stent-graft may be flared radially outward in a proximal direction, when the second stent-graft is in its radially-expanded state.

For any of the applications described above, a section of the second covering element may extend through the first lateral opening and into a portion of the first stent-graft when the second stent-graft is disposed through the first lateral opening.

For any of the applications described above, the second stent-graft may have a generally cylindrical shape when the second stent-graft is unconstrained in its radially-expanded state.

For any of the applications described above, the first and the second stent-grafts may be configured for transluminal delivery for transport to respective sites within a body lumen when in their radially-compressed states. For some applications, the second stent-graft is adapted for transluminal delivery in its radially-compressed state through a portion of the first stent-graft and the first lateral opening, while the first stent-graft is in its radially-expanded state.

For any of the applications described above, the first covering element only partially covers the first support element.

For any of the applications described above, the first stent-graft may further include one or more radiopaque markers, located in a vicinity of the first lateral opening.

For any of the applications described above, at least one of the first and the second support elements may be shaped so as to define one or more circumferentially-disposed, radially-protruding barbs, when the at least one of the first and second support elements is in its radially-expanded state.

For any of the applications described above, an axial length of the first stent-graft may be between 5 and 30 cm, when the first stent-graft is unconstrained in its radially-expanded state. For any of the applications described above, an axial length of the second stent-graft may be between 5 and 20 cm, when the second stent-graft is unconstrained in its radially-expanded state. For any of the applications described above, a greatest perimeter of the first stent-graft may be between 4.5 and 19 cm, when the first stent-graft is unconstrained in its radially-expanded state. For any of the applications described above, a greatest perimeter of the second stent-graft may be between 9 and 22 cm, when the second stent-graft is unconstrained in its radially-expanded state.

For any of the applications described above, a perimeter of one end of the first stent-graft may be between 7.5 and 15 cm, when the first stent-graft is unconstrained in its radially-expanded state. For any of the applications described above, a perimeter of one end of the second stent-graft may be between 5 and 15.4 cm, when the second stent-graft is unconstrained in its radially-expanded state.

There is also provided, in accordance with an application of the present invention, a method for treating a patient, including:

transvascularly introducing and positioning a first stent-graft, which is shaped so as to define one or more first lateral openings, such that (a) a proximal portion of the first stent-graft, including a proximal end of the first-stent-graft, is in a proximal portion of a main blood vessel, (b) a distal portion of the first stent-graft, including a distal end of the first stent-graft, is in a branching blood vessel that branches from the main blood vessel at a bifurcation, and (c) one of the one or more first lateral openings is disposed within the main blood vessel facing toward a distal portion of the main blood vessel, which distal portion is distal to the bifurcation; and transvascularly introducing and passing a second stent-graft through the proximal portion of the first stent-graft such that the second stent-graft is disposed through the first lateral opening and is disposed partially in the distal portion of the main blood vessel, and forms a blood-impervious seal with the first stent-graft around the first lateral opening.

There is further provided, in accordance with an application of the present invention, a method for treating a patient, including:

transvascularly introducing and positioning a first stent-graft, which is shaped so as to define one or more first lateral openings, such that (a) a proximal portion of the first stent-graft, including a proximal end of the first-stent-graft, is in an upper part of a descending aorta, (b) a distal portion of the first stent-graft, including a distal end of the first stent-graft, is in a branch of an aortic arch, and (c) one of the one or more first lateral openings is disposed within the aortic arch facing upstream, generally toward an ascending aorta; and transvascularly introducing and passing a second stent-graft through the proximal portion of the first stent-graft such that the second stent-graft is disposed through the one of the one or more first lateral openings and is disposed partially in the aortic arch, and forms a blood-impervious seal with the first stent-graft around the one of the one or more first lateral openings.

For some applications, the branch is a left subclavian artery, and positioning the first stent-graft includes positioning the first stent-graft such that the distal portion of the first stent-graft, including the distal end of the first stent-graft, is in the left subclavian artery. For some applications, passing includes passing the second stent-graft through the proximal portion of the first stent-graft such that the second stent-graft is disposed through the one of the one or more first lateral openings and is disposed partially in the aortic arch, and a distal portion of the second stent-graft, including a distal end of the second stent-graft, is in a left common carotid artery.

For some applications:
the branch is a brachiocephalic artery,
the first lateral openings include proximal and distal superior first lateral openings, and a distal inferior first lateral opening,
positioning the first stent-graft includes positioning the first stent-graft such that (a) the distal portion of the first stent-graft, including the distal end of the first stent-graft, is in the brachiocephalic artery, (b) the distal inferior first lateral opening faces upstream, generally toward the ascending aorta, and (c) the proximal and the distal superior first lateral openings face and are aligned with a left subclavian artery and a left common carotid artery, respectively, and passing the second stent-graft includes passing the second stent-graft through the proximal portion of the first stent-graft such that the second stent-graft is disposed through the distal inferior first lateral opening and is disposed partially in the distal portion of the main blood vessel.

For some applications, the method further includes transvascularly introducing and positioning third and fourth stent-grafts through the proximal portion of the first stent-graft such the third and fourth stent-grafts are disposed through the proximal and the distal superior first lateral openings, respectively, and are disposed partially in the left subclavian artery and the left common carotid artery, respectively, and form blood-impervious seals with the first stent-graft around the proximal and the distal superior first lateral openings, respectively.

For some applications:
the branch is a left common carotid artery,
the first lateral openings include a superior first lateral opening and an inferior first lateral opening,
positioning the first stent-graft includes positioning the first stent-graft such that (a) the distal portion of the first stent-graft, including the distal end of the first stent-graft, is in the left common carotid artery, (b) the inferior first lateral opening faces upstream, generally toward the ascending aorta, and (c) the superior first lateral opening faces and is aligned with a left subclavian artery, and further including transvascularly introducing a third stent-graft via a right subclavian artery, and positioning the third stent-graft such that a proximal portion of the third stent-graft, including a proximal end of the third stent-graft is disposed in a brachiocephalic artery, and a distal portion of the third stent-graft, including a proximal end of the third-stent graft, is disposed in a portion of at least one blood vessel selected from the group consisting of: the aortic arch, and an upper part of an ascending aorta, and a third lateral opening defined by the third stent-graft faces upstream, generally toward the descending aorta, passing the second stent-graft includes passing the second stent-graft through the proximal portion of the first stent-graft such that the second stent-graft is disposed through the inferior first lateral opening and the third lateral opening, and is disposed partially in the aortic arch.

For some applications, the method further includes transvascularly introducing and positioning a fourth stent-graft through the proximal portion of the first stent-graft such the fourth stent-graft is disposed through the superior first lateral opening, and is disposed partially in the left subclavian artery, and forms a blood-impervious seal with the first stent-graft around the superior first lateral opening.

For some applications, transvascularly introducing the first and the second stent-grafts includes separately transvascularly introducing the first and the second stent-grafts while they are not fixed to one another.

For some applications:
transvascularly introducing the first stent-graft includes transvascularly introducing the first stent-graft while in a radially-compressed state, and transitioning the first stent-graft to a radially-expanded state after positioning the first stent-graft, transvascularly introducing the second stent-graft includes transvascularly introducing the second stent-graft while in a radially-compressed state, passing the second stent-graft including passing the second stent-graft, while in its radially-compressed state, through the proximal portion after the first stent-graft has been transitioned to its radially-expanded state, and the method further includes, after passing the second stent-graft, transitioning, without inverting, the second stent-graft from a radially-compressed state to a radially-expanded state.

For some applications, transitioning the first stent-graft includes transitioning the first stent-graft to its radially-expanded state in which a first perimeter of a first end of the first stent-graft equals at least 200% of a second perimeter of a second end of the first stent-graft, such as at least 250%, or at least 400%. For some applications, the first perimeter is between 2.5 and 4.5 cm, and the second perimeter is between 1 and 1.5 cm.

For some applications, the method further includes identifying that the patient suffers from a thoracic aortic aneurysm of an aortic arch, and transvascularly introducing the first stent-graft includes transvascularly introducing the first stent-graft responsively to the identifying.

There is still further provided, in accordance with an application of the present invention, a method for treating a patient, including:

transvascularly introducing and positioning a first stent into vasculature of the patient;

transvascularly introducing and passing a second stent through a portion of the first stent such that the second stent is disposed through a first lateral opening defined by the first stent; and transvascularly introducing and passing a third stent sequentially through (a) the portion of the first stent, (b) the first lateral opening, and (c) a portion of the second stent, such that the third stent is disposed through a second lateral opening defined by the second stent.

For some applications, the first and second stents include respective first and second support elements and respective first and second covering elements attached to the first and second support elements, respectively, and passing the second stent includes disposing the second stent through the first lateral opening such that the second covering element forms a blood-impervious seal with the first covering element around the first lateral opening.

For some applications, the second and third stents include respective second and third support elements and respective second and third covering elements attached to the second and third support elements, respectively, and passing the third stent includes disposing the third stent through the second lateral opening such that the third covering element forms a blood-impervious seal with the second covering element around the second lateral opening.

For some applications, transvascularly introducing the first, the second, and the third stent includes separately transvascularly introducing the first, the second, and the third stent while they are not fixed to one another.

For some applications, passing the third stent includes passing the third stent while the first and the second stent are in radially-expanded states, and the third stent is in a radially-compressed state.

For some applications, the method further includes transvascularly introducing and passing a fourth stent sequentially through (a) the portion of the first stent, (b) the first lateral opening, (c) the portion of the second stent, (d) the second lateral opening, and (e) a portion of the third stent, such that the fourth stent is disposed through a third lateral opening defined by the third stent. For some applications, passing the fourth stent includes passing the fourth stent while the first, the second, and the third stent are in radially-expanded states, and the fourth stent is in a radially-compressed state.

For some applications:

positioning the first stent includes positioning the first stent such that (a) a proximal portion of the first stent, including a proximal end of the first-stent, is in a proximal portion of a main blood vessel, (b) a distal portion of the first stent, including a distal end of the first stent, is in a branching blood vessel that branches from the main blood vessel at a bifurcation, and (c) the first lateral opening is disposed within the main blood vessel facing toward a distal portion of the main blood vessel, which distal portion is distal to the bifurcation, and passing the second stent includes passing the second stent through the portion of the first stent such that the second stent is disposed through the first lateral opening and is disposed partially in the distal portion of the main blood vessel.

For some applications:

the main blood vessel is an aorta, the branching blood vessel is a branch of an aortic arch, and the distal portion of the main body lumen is a portion of the aortic arch, positioning the first stent includes positioning the first stent such that the proximal portion of the first stent, including the proximal end of the first-stent, is in an upper part of a descending aorta, the distal portion of the first stent, including the distal end of the first stent, is in the branch of the aortic arch, and the first lateral opening faces upstream, generally toward an ascending aorta, and passing includes passing the second stent through the proximal portion of the first stent such that the second stent is disposed through the first lateral opening and is disposed partially in the aortic arch.

For some applications, the branch is a left subclavian artery, and positioning the first stent includes positioning the first stent such that the distal portion of the first stent, including the distal end of the first stent, is in the left subclavian artery. For some applications, passing includes passing the second stent through the proximal portion of the first stent such that the second stent is disposed through the first lateral opening and is disposed partially in the aortic arch, and a distal portion of the second stent, including a distal end of the second stent, is in a left common carotid artery.

For some applications:

transvascularly introducing the first stent includes transvascularly introducing the first stent while in a radially-compressed state, and transitioning the first stent to a radially-expanded state after positioning the first stent, transvascularly introducing the second stent includes transvascularly introducing the second stent while in a radially-compressed state, passing the second stent including passing the second stent, while in its radially-compressed state, through the proximal portion after the first stent has been transitioned to its radially-expanded state, and the method further includes, after passing the second stent, transitioning, without inverting, the second stent from a radially-compressed state to a radially-expanded state.

For some applications, transitioning the first stent includes transitioning the first stent to its radially-expanded state in which a first perimeter of a first end of the first stent equals at least 200% of a second perimeter of a second end of the first stent, such as at least 250% or at least 400%. For some applications, the first perimeter is between 7.5 and 15 cm, and the second perimeter is between 2.5 and 5.7 cm.

For some applications, the method further includes identifying that the patient suffers from a thoracic aortic aneurysm of an aortic arch, and transvascularly introducing the first stent includes transvascularly introducing the first stent responsively to the identifying.

There is additionally provided, in accordance with an application of the present invention, a method including:

transvascularly introducing, into vasculature of a patient, a delivery tool, which includes an outer tube, in which first and second stents are initially positioned at respective axial sites within the outer tube, in radially-compressed states without being fixed to each other;

deploying the first stent from a distal end of the outer tube, such that the first stent transitions to a radially-expanded state; and after the first stent transitions to the radially-expanded state, deploying the second stent from the distal end of the outer tube, such that the second stent transitions to a radially-expanded state.

For some applications:

the delivery tool is shaped so as to define first and second stopper elements, which are configured and initially positioned to prevent movement of the first and second stents, respectively, in a proximal direction away from the distal end of the outer tube, deploying the first stent includes withdrawing, in the proximal direction, the outer tube, such that the first stopper element prevents the movement of the first stent in the proximal direction, and deploying the second stent includes withdrawing the outer tube in the proximal direction, such that the second stopper element prevents the movement of the second stent in the proximal direction.

For some applications, an inner surface of the outer tube is shaped so as to define the first and second stopper elements.

For some applications, the delivery tool further includes an inner longitudinal member, which is initially positioned such that first and second portions thereof are within the first and second stents, respectively, and the inner longitudinal member is shaped so as to define the first and second stopper elements.

For some applications:

the delivery tool further includes an inner longitudinal member, which is initially positioned such that first and second portions thereof are within the first and second stents, respectively, the inner longitudinal member is shaped so as to define a stopper element, which is (a) configured and initially positioned to prevent movement of the first stent in a proximal direction away from the distal end of the outer tube, and (b) configured to be withdrawable in the proximal direction through the second stent, and after being thus withdrawn, to prevent movement of the second stent in the proximal direction, deploying the first stent includes withdrawing the outer tube in the proximal direction, such that the stopper element prevents the movement of the first stent in the proximal direction, and deploying the second stent includes:
  withdrawing the inner longitudinal member in the proximal direction, such that the stopper element passes through the second stent; and
  withdrawing the outer tube in the proximal direction, such that the stopper element prevents the movement of the second stent in the proximal direction.

There is yet additionally provided, in accordance with an application of the present invention, a method for treating a patient, including:

transvascularly introducing a stent-graft into vasculature of the patient; and positioning the stent-graft such that (a) a proximal portion of the stent-graft, including a proximal end of the first-stent-graft, is in a brachiocephalic artery, (b) a distal portion of the stent-graft, including a distal end of the stent-graft, is disposed in a portion of at least one blood vessel selected from the group consisting of: an aortic arch, and an upper part of an ascending aorta, and (c) a lateral opening defined by the stent-graft is disposed in the aortic arch facing generally toward a descending aorta.

For some applications, the stent-graft is a first stent-graft, and further including transvascularly introducing and positioning a second stent-graft through the lateral opening, such that the second stent-graft forms a blood-impervious seal with the first stent-graft around the lateral opening.

There is also provided, in accordance with an application of the present invention, a method for assembling a multi-component stent-graft system, the method including:

providing (a) a first generally tubular stent-graft, which is shaped so as to define a first lateral opening when the first stent-graft is in a radially-expanded state, (b) a second generally tubular stent-graft, which is shaped so as to define a second lateral opening when the second stent-graft is in a radially-expanded state, and (c) a third generally tubular stent-graft;

while the first stent-graft is in its radially-expanded state and the second stent-graft is in a radially-compressed state, disposing the second stent-graft through the first lateral opening, and causing the second stent-graft to transition to its radially-expanded state, such that the second stent-graft forms a blood-impervious seal with the first stent-graft around the first lateral opening; and while the second stent-graft is in its radially-expanded state and the third stent-graft is in a radially-compressed state, disposing the third stent-graft through the second lateral opening, and causing the third stent-graft to transition to a radially-expanded state, such that the third stent-graft forms a blood-impervious seal with the second stent-graft around the second lateral opening.

For some applications, the third stent-graft is shaped so as to define a third lateral opening when in its radially-expanded state, and the method further includes:

providing a fourth generally tubular stent-graft; and while the third stent-graft is in its radially-expanded state and the fourth stent-graft is in a radially-compressed state, disposing the fourth stent-graft through the third lateral opening, and causing the fourth stent-graft to transition to a radially-expanded state, such that the fourth stent-graft forms a blood-impervious seal with the third stent-graft around the third lateral opening.

There is further provided, in accordance with an application of the present invention, a method for assembling a multi-component stent-graft system, the method including:

providing (a) a first generally tubular stent-graft, which, when unconstrained in a radially-expanded state: (i) defines a first lateral opening, and (ii) has a first perimeter of a first end thereof that equals at least 200% of a second perimeter of a second end thereof, and (b) a second generally tubular stent-graft; and while the first stent-graft is in its radially-expanded state and the second stent-graft is in a radially-compressed state, disposing the second stent-graft through the first lateral opening, and causing the second stent-graft to transition to a radially-expanded state, such that the second stent-graft forms a blood-impervious seal with the first stent-graft around the first lateral opening.

There is still further provided, in accordance with an application of the present invention, a method for assembling a multi-component stent-graft system, the method including:

providing (a) a first stent-graft, which is shaped so as to define, when in a radially-expanded state, proximal and distal superior first lateral openings facing in a first radial direction, and a distal inferior first lateral opening facing a second radial direction generally opposite the first radial direction, and (b) second, third, and fourth branching stent-grafts; and while the first stent-graft is in its radially-expanded state and the second stent-graft is in a radially-compressed state, disposing the second stent-graft through the distal inferior first lateral opening, and causing the second stent-graft to transition to a radially-expanded state, such that the second stent-graft forms a blood-impervious seal with the first stent-graft around the distal inferior first lateral opening;

while the first stent-graft is in its radially-expanded state and the third stent-graft is in a radially-compressed state, disposing the third stent-graft through the distal superior first lateral opening, and causing the third stent-graft to transition to a radially-expanded state, such that the third stent-graft forms a blood-impervious seal with the first stent-graft around the distal superior first lateral opening; and while the first stent-graft is in its radially-expanded state and the fourth stent-graft is in a radially-compressed state, disposing the fourth stent-graft through the proximal superior first lateral opening, and causing the fourth stent-graft to transition to a radially-expanded state, such that the fourth stent-graft forms a blood-impervious seal with the first stent-graft around the proximal superior first lateral opening.

There is additionally provided, in accordance with an application of the present invention, a method for assembling a multi-component stent-graft system, the method including:

providing (a) a first stent-graft, which is shaped so as to define, when in a radially-expanded state, a superior first lateral opening facing in a first radial direction, and an inferior first lateral opening facing in a second radial direction generally opposite the first radial direction, (b) a second stent-graft, (c) a third stent-graft, which is shaped so as to define a third lateral opening through the third stent-graft when the third stent-graft is in a radially-expanded state, and (d) a fourth stent-graft;

while the first stent-graft is in its radially-expanded state and the second stent-graft is in a radially-compressed state, disposing the second stent-graft through the superior first lateral opening, and causing the second stent-graft to transition to a radially-expanded state, such that the second stent-graft forms a blood-impervious seal with the first stent-graft around the superior first lateral opening; and while the first and the third stent-grafts are in their radially-expanded states and the fourth stent-graft is in a radially-compressed state, disposing first and second ends of the fourth stent-graft through the inferior first lateral opening and the third lateral opening, respectively, and causing the fourth stent-graft to transition to a radially-expanded state, such that the fourth stent-graft forms blood-impervious seals with the first stent-graft around the inferior first lateral opening and the third stent-graft around the third lateral opening.

The present invention will be more fully understood from the following detailed description of embodiments thereof, taken together with the drawings, in which:

BRIEF DESCRIPTION OF THE DRAWINGS

FIGS. 1A-C are schematic illustrations of a multi-component stent-graft system, in accordance with respective applications of the present invention;

FIG. 4 is a schematic illustration of another configuration of the multi-component stent-graft system of FIGS. 1A-C and 2, in accordance with an application of the present invention;

FIGS. 12A-C are schematic illustrations of another configuration of the delivery tool of FIG. 10, in accordance with an application of the present invention.

DETAILED DESCRIPTION OF APPLICATIONS

Figure 2:
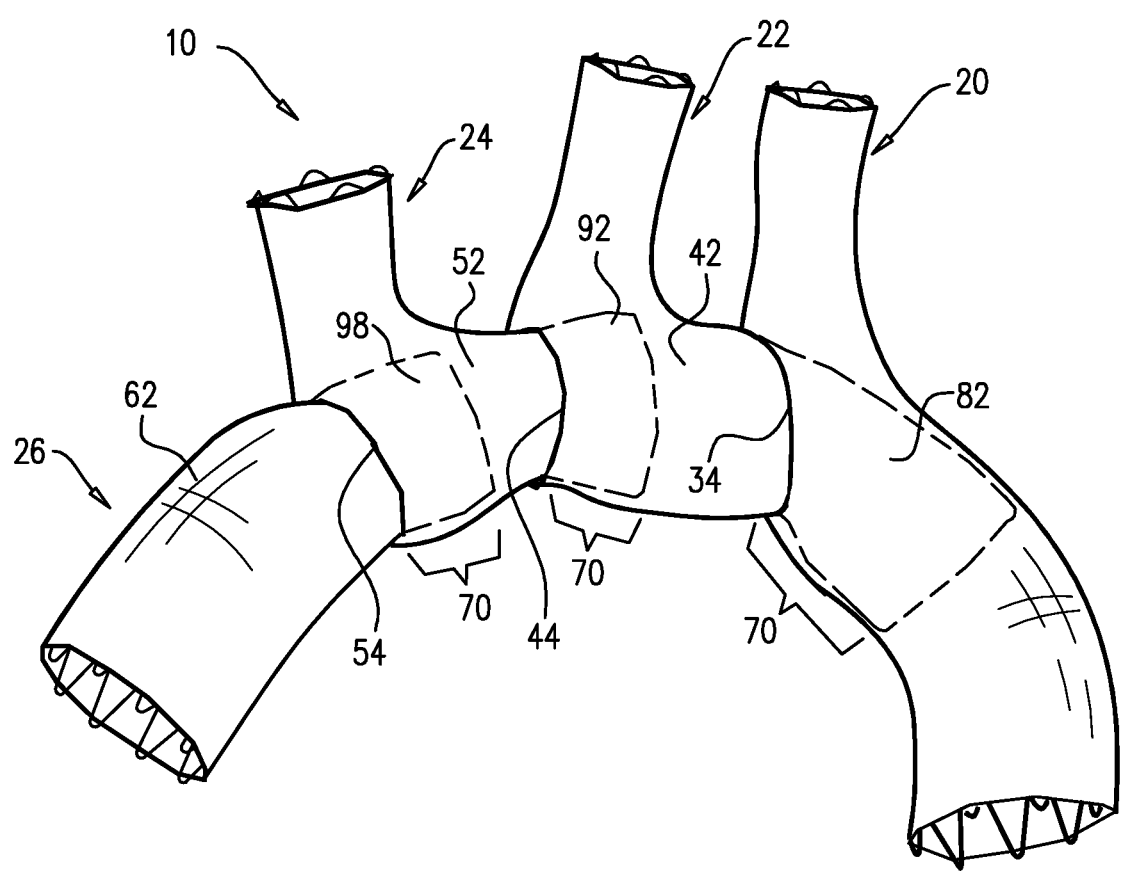
FIG. 2 is a schematic illustration of the multi-component stent-graft system of FIGS. 1-C in an assembled state, in accordance with an application of the present invention.

In some applications of the present invention, a multi-component stent-graft system 10 is provided for treating a thoracic aortic aneurysm 110, such as of the aortic arch. The system is configured to be deployed in the thoracic aorta and in one or more of the branches of the aortic arch (the brachiocephalic artery, the left common carotid artery, and/or the left subclavian artery).

The multi-component stent-graft system is configured to be deployed in a straightforward procedure that readily accommodates ordinary anatomical variances among different patients. For example, the locations of bifurcations of the three branches of the aortic arch vary among patients. The stent-grafts of the system are assembled in situ to accommodate the dimensions of the particular patient's anatomy, generally without requiring prior customization of the stent-grafts or in situ modifications to the stent-grafts, which might be expensive and/or complex.

Typically, upon deployment, the multi-component stent-graft system defines a blood-flow path from the ascending aorta, over the aortic arch, and to the descending aorta. The multi-component stent-graft system additionally provides blood-flow paths to the three branches of the aortic arch.

The multi-component stent-graft system may have various configurations, and may be deployed in various combinations and subsets of the aortic arch, ascending aorta, descending aorta, and three branches of the aortic arch. Hereinbelow are described three exemplary high-level configurations of the stent-graft system, each of which includes numerous sub-configurations. For the sake of convenience, and without limiting the features of these configurations, the three exemplary configurations are referred to hereinbelow as: (1) a "first stent-graft having a single lateral opening," (2) a "first stent-graft having three lateral openings," and (3) a "first stent-graft having two lateral openings."

First Stent-Graft Having a Single Lateral Opening

FIGS. 1A-C are schematic illustrations of multi-component stent-graft system 10, in accordance with respective applications of the present invention. In these applications, multi-component stent-graft system 10 comprises (a) a first stent-graft 20, (b) a second stent-graft 22, (c) optionally, a third stent-graft 24, and (d) optionally, a fourth stent-graft 26. The stent-grafts are configured to assume radially-compressed states, such as when initially positioned in one or more outer tubes of one or more delivery tools, as described hereinbelow with reference to FIGS. 3B, 3E, 3H, and 3K, and to assume radially-expanded states upon being deployed from the outer tube(s), as described hereinbelow with reference to FIGS. 3C, 3F, 3I, and 3L. FIGS. 1A-C show the stent-grafts in their radially-expanded states. For some applications, the stent-grafts are relaxed in their radially-expanded states. For some applications, the stent-grafts are configured to be self-expanding. For example, they may be heat-set to assume their radially-expanded states.

The First Stent-Graft

First stent-graft 20 typically comprises a first generally tubular support element 30 and a first covering element 32 attached to the first support element so as to at least partially cover (e.g., only partially cover) the first support element. Support element 30 typically comprises a plurality of structural stent elements. For some applications, at least some of, e.g., all of, the structural stent elements are interconnected (as shown in the figures), while for other applications, at least a portion of, e.g., all, of the structural stent elements are not interconnected (configuration not shown). For some applications, support element 30, as well as support elements 40, 50, and 60, which are described hereinbelow, comprise a super-elastic alloy, such as Nitinol. Covering element 32 serves as a blood flow guide through at least a portion of the first stent-graft. Each of covering element 32, as well as covering elements 42, 52, and 62, which are described hereinbelow, typically comprises at least one biologically-compatible substantially blood-impervious flexible sheet, which is attached (such as by stitching) to at least a portion of the respective support element, on either side of the surfaces defined by the support element. The flexible sheet may comprise, for example, a polymeric material (e.g., a polyester, or polytetrafluoroethylene), a textile material (e.g., polyethylene terephthalate (PET)), natural tissue (e.g., saphenous vein or collagen), or a combination thereof.

First covering element 32 and first support element 30 are shaped so as to together define a first lateral opening 34 through first stent-graft 20 when the first stent-graft is in its radially-expanded state. For some applications, the first covering element and first support element are shaped so as to together define exactly one first lateral opening, as shown in FIGS. 1A-C. For other applications, the first covering element and first support element are shaped so as to together define more than one first lateral opening, such as exactly three lateral openings or exactly two lateral openings, as described hereinbelow with reference to FIGS. 4-5 and 6-7, respectively, or more than three lateral openings (configuration not shown).

For some applications, when first stent-graft 20 is unconstrained in its radially-expanded state, i.e., no forces are applied to the stent-graft by a delivery tool, walls of a blood vessel, or otherwise, a first perimeter P1 of a first (proximal) end 36 of the first stent-graft is greater than a second perimeter P2 of a second (distal) end 38 of the first stent-graft, and/or a first cross-sectional area of the first end 36 is greater than a second cross-sectional area of second end 38. For applications in which first stent-graft 20 is generally cylindrical when unconstrained in its radially-expanded state, first and second perimeters P1 and P2 are first and second diameters. For example, first perimeter P1 may equal at least 150% of second perimeter P2, such as at least 200%, at least 250%, at least 300%, or at least 400%, and/or the first cross-sectional area may equal at least 225% of the second cross-sectional area, such as at least 400%, at least 625%, at least 900%, or at least 1600%. For some applications, a proximal axial quarter of first-stent graft 20 includes a portion of the stent-graft extending from first proximal end 36 along 25% of an axial length of the stent-graft, and a distal axial quarter of the first stent-graft includes a portion of the stent-graft extending from second distal end 38 along 25% of the axial length of the stent-graft. For some applications, an average perimeter of the proximal axial quarter equals at least 150% of an average perimeter of the distal axial quarter, such as at least 200%, at least 250%, at least 300%, or at least 400%.

For example, first perimeter P1 may be at least 7.5 cm, no more than 15 cm, and/or between 7.5 and 15 cm, such as at least 9 cm, no more than 13 cm, and/or between 9 and 13 cm, and second perimeter P2 may be at least 2.5 cm, no more than 5.7 cm, and/or between 2.5 and 5.7 cm, such as at least 3 cm, no more than 4.5 cm, and/or between 3 and 4.5 cm.

For some applications, when first stent-graft 20 is unconstrained in its radially-expanded state, a perimeter of first lateral opening 34 is at least 4.5 cm, no more than 14 cm, and/or between 4.5 and 14 cm, such as at least 6 cm, no more than 12.5 cm, and/or between 6 and 12.5 cm.

For some applications, when first stent-graft 20 is unconstrained in its radially-expanded state, a perimeter of first lateral opening 34 is at least 30%, e.g., at least 40%, or at least 75% of first perimeter P1, and/or at least 83%, e.g., at least 100%, or at least 200% of second perimeter P2. For some applications in which first perimeter P1 does not equal second perimeter P2, the perimeter of first lateral opening 34 is at least 60% of the lesser of first and second perimeters P1 and P2.

For some applications, first stent-graft 20, when unconstrained in its radially-expanded state, has an axial length of at least 5 cm, no more than 40 cm, and/or between 5 and 30 cm, such as at least 10 cm, no more than 30 cm, and/or between 10 and 30 cm. (The axial length is measured along a central longitudinal axis of the stent-graft, including in applications in which the stent-graft is curved, as described hereinbelow with reference to FIG. 1B.) For some applications, first stent-graft 20, when unconstrained in its radially-expanded state, has a greatest perimeter (at any axial location along the stent-graft) of at least 4.5 cm, no more than 19 cm, and/or between 4.5 and 19 cm, such as at least 12.5 cm, no more than 16 cm, and/or between 12.5 and 16 cm.

Figure 3A:
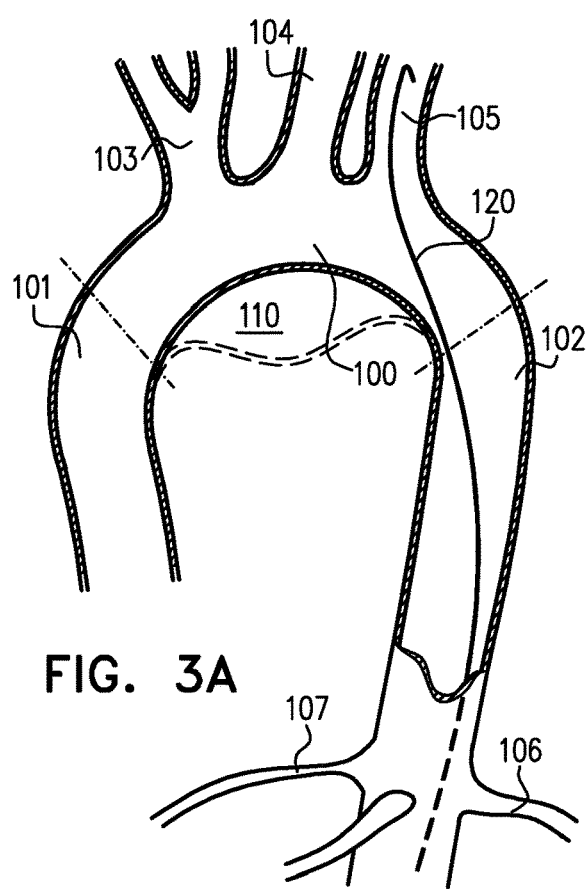
FIGS. 3A-L are schematic illustrations of an exemplary transluminal delivery procedure for implanting the multi-component stent-graft system of FIGS. 1A, 1B, 1C, and/or 2, in accordance with an application of the present invention.
Figure 3B:
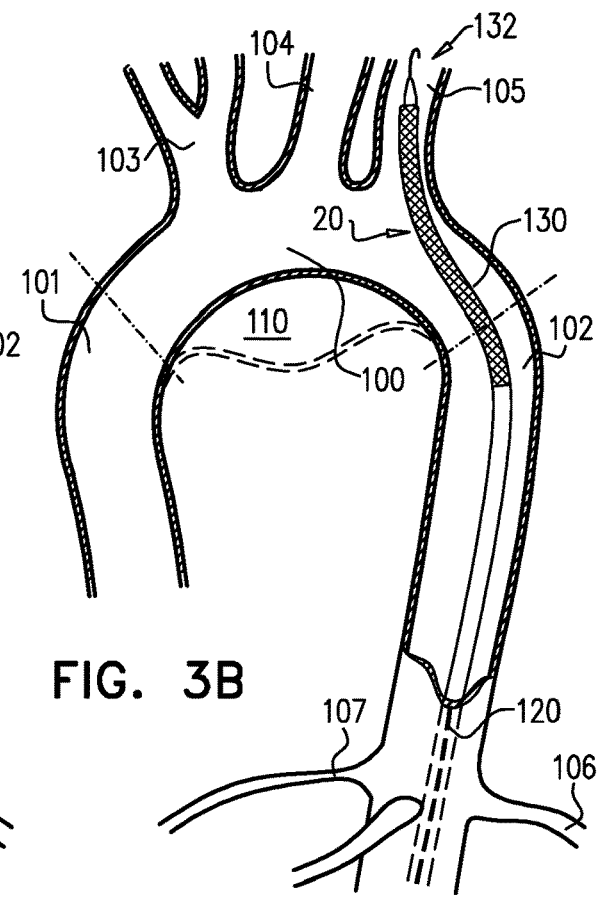
Figure 3C:
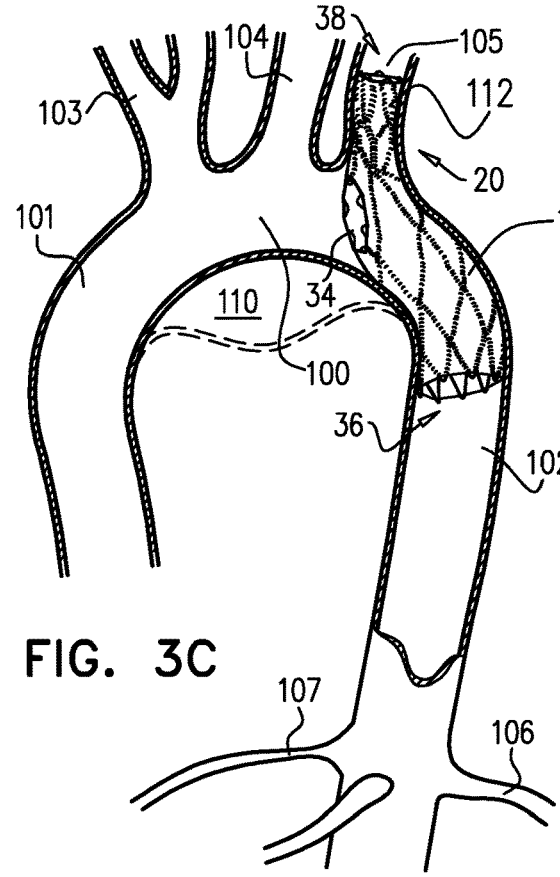

For some applications, such dimensions allow the first stent-graft to be positioned such that (a) a proximal, radially larger, portion of the stent-graft, including proximal end 36 thereof, is disposed in the aorta downstream from the bifurcation with the left subclavian artery, at least partially in the upper part of the descending aorta, and (b) a distal, radially smaller, portion of the stent-graft, including distal end 38 thereof, is disposed in the left subclavian artery, such as described hereinbelow with reference to FIG. 3C. For some applications, the proximal portion of the stent-graft has an average perimeter that is greater than (e.g., between 5% and 15% greater than) an average perimeter of the portion of the aorta in which it is disposed (excluding expansion of the aorta due to the aneurysm, i.e., assuming the aorta were healthy). For some applications, the distal portion of the stent-graft has an average perimeter that is greater than (e.g., between 5% and 15% greater than) the average perimeter of the portion of the left subclavian artery in which it is disposed.

The Second Stent-Graft

Second stent-graft 22 typically comprises a second generally tubular support element 40 and a second covering element 42 attached to the second support element so as to at least partially cover the second support element. Support element 40 typically comprises a plurality of structural stent elements. For some applications, at least some of, e.g., all of, the structural stent elements are interconnected (as shown in the figures), while for other applications, at least a portion of, e.g., all, of the structural stent elements are not interconnected (configuration not shown). Covering element 42 serves as a blood flow guide through at least a portion of the second stent-graft.

For applications in which multi-component stent-graft system 10 further comprises third stent-graft 24, second covering element 42 and second support element 40 are typically shaped so as to together define a second lateral opening 44 through second stent-graft 22 when the second stent-graft is in its radially-expanded state. The second stent-graft is typically configured to transition, without inverting, from its radially-compressed state to its radially-expanded state, typically upon being deployed from an outer tube of a deployment tool, such as described hereinbelow with reference to FIG. 3F.

For some applications, when second stent-graft 22 is unconstrained in its radially-expanded state, i.e., no forces are applied to the stent-graft by a delivery tool, walls of a blood vessel, or otherwise, a third perimeter P3 of a first (proximal) end 46 of the second stent-graft may be at least 5 cm, no more than 15.4 cm, and/or between 5 and 15.4 cm, and a fourth perimeter P4 of a second (distal) end 48 of the second stent-graft may be at least 2.5 cm, no more than 5.7 cm, and/or between 2.5 and 5.7 cm. For applications in which second stent-graft 22 is generally cylindrical when unconstrained in its radially-expanded state, third and fourth perimeters P3 and P4 are third and fourth diameters. For some applications, third and fourth perimeters P3 and P4 are equal.

For some applications, when second stent-graft 22 is unconstrained in its radially-expanded state, a perimeter of second lateral opening 44 is at least 4.5 cm, no more than 14 cm, and/or between 4.5 and 14 cm, such as at least 6 cm, no more than 12.5 cm, and/or between 6 and 12.5 cm.

For some applications, second stent-graft 22, when unconstrained in its radially-expanded state, has an axial length of at least 5 cm, no more than 20 cm, and/or between 5 and 20 cm, such as at least 8 cm, no more than 15 cm, and/or between 8 and 15 cm. (The axial length is measured along a central longitudinal axis of the stent-graft, including in applications in which the stent-graft is curved, as described hereinbelow with reference to FIG. 1B.) For some applications, second stent-graft 22, when unconstrained in its radially-expanded state, has a greatest perimeter (at any axial location along the stent-graft) of at least 9 cm, no more than 22 cm, and/or between 9 and 22 cm, and/or at least 12 cm, no more than 19 cm, and/or between 12 and 19 cm.

For some applications, such dimensions allow the second stent-graft to be positioned such that (a) a proximal portion of the stent-graft is disposed within the lateral opening 34 of the first stent-graft, and (b) a distal portion of the stent-graft, including distal end 48 thereof, is disposed in a left common carotid artery, such as described hereinbelow with reference to FIG. 3F. For some applications, the proximal portion of the stent-graft has an average perimeter that is less than (e.g., between 40% and 70% less than) an average perimeter of the portion of the aortic arch in which it is disposed (excluding expansion of the aortic arch due to the aneurysm, i.e., assuming the aortic arch were healthy). For some applications, the distal portion of the stent-graft has an average perimeter that is greater than (e.g., between 5% and 15% greater than) the average perimeter of the portion of the left common carotid artery in which it is disposed.

The third stent-graft

For applications in which multi-component stent-graft system 10 further comprises third stent-graft 24, the third stent-graft typically comprises a third generally tubular support element 50 and a third covering element 52 attached to the third support element so as to at least partially cover the third support element. Support element 50 typically comprises a plurality of structural stent elements. For some applications, at least some of, e.g., all of, the structural stent elements are interconnected (as shown in the figures), while for other applications, at least a portion of, e.g., all, of the structural stent elements are not interconnected (configuration not shown). Covering element 52 serves as a blood flow guide through at least a portion of the third stent-graft.

For applications in which multi-component stent-graft system 10 further comprises fourth stent-graft 26, third covering element 52 and third support element 50 are typically shaped so as to together define a third lateral opening 54 through third stent-graft 24 when the third stent-graft is in its radially-expanded state. The third stent-graft is typically configured to transition, without inverting, from its radially-compressed state to its radially-expanded state, typically upon being deployed from an outer tube of a deployment tool, such as described hereinbelow with reference to FIG. 3I.

For some applications, when third stent-graft 24 is unconstrained in its radially-expanded state, i.e., no forces are applied to the stent-graft by a delivery tool, walls of a blood vessel, or otherwise, a fifth perimeter P5 of a first end 56 of the third stent-graft may be at least 5.5 cm, no more than 17 cm, and/or between 5.5 and 17 cm, and a sixth perimeter P6 of a second end 58 of the third stent-graft may be at least 2.75 cm, no more than 6.3 cm, and/or between 2.75 and 6.3 cm. For applications in which third stent-graft 24 is generally cylindrical when unconstrained in its radially-expanded state, fifth and sixth perimeters P5 and P6 are fifth and sixth diameters. For some applications, fifth and sixth perimeters P5 and P6 are equal.

For some applications, when third stent-graft 24 is unconstrained in its radially-expanded state, a perimeter of third lateral opening 54 is at least 4.5 cm, no more than 14 cm, and/or between 4.5 and 14 cm, such as at least 4.5 cm, no more than 12 cm, and/or between 4.5 and 12 cm.

For some applications, third stent-graft 24, when unconstrained in its radially-expanded state, has an axial length of at least 8.8 cm, or more than 16.5 cm, and/or between 8.8 and 16.5 cm. (The axial length is measured along a central longitudinal axis of the stent-graft, including in applications in which the stent-graft is curved, as described hereinbelow with reference to FIG. 1B.) For some applications, third stent-graft 24, when unconstrained in its radially-expanded state, has a greatest perimeter (at any axial location along the stent-graft) of at least 4.4 cm, no more than 7.7 cm, and/or between 4.4 and 7.7 cm, such as at least 3.3 cm, no more than 6.6 cm, and/or between 3.3 and 6.6 cm.

For some applications, such dimensions allow the third stent-graft to be positioned such that (a) a proximal portion of the stent-graft is disposed in the aortic arch, and (b) a distal portion of the stent-graft, including distal end 58 thereof, is disposed in a brachiocephalic artery, such as described hereinbelow with reference to FIG. 3I. For some applications, the proximal portion of the stent-graft has an average perimeter that is less than (e.g., between 40% and 70% less than) an average perimeter of the portion of the aortic arch in which it is disposed (excluding expansion of the aortic arch due to the aneurysm, i.e., assuming the aortic arch were healthy). For some applications, the distal portion of the stent-graft has an average perimeter that is greater than (e.g., between 5% and 15% greater than) the average perimeter of the portion of the brachiocephalic artery in which it is disposed.

The Fourth Stent-Graft

For applications in which multi-component stent-graft system 10 further comprises fourth stent-graft 26, the fourth stent-graft typically comprises a fourth generally tubular support element 60 and a third covering element 62 attached to the fourth support element so as to at least partially cover the fourth support element. Support element 60 typically comprises a plurality of structural stent elements. For some applications, at least some of, e.g., all of, the structural stent elements are interconnected (as shown in the figures), while for other applications, at least a portion of, e.g., all of, the structural stent elements are not interconnected (configuration not shown). Covering element 62 serves as a blood flow guide through at least a portion of the fourth stent-graft.

For some applications, fourth covering element 62 and fourth support element 60 are not shaped so as to together define any lateral openings through the fourth stent-graft when the fourth stent-graft is in its radially-expanded state.

For some applications, when fourth stent-graft 26 is unconstrained in its radially-expanded state, i.e., no forces are applied to the stent-graft by a delivery tool, walls of a blood vessel, or otherwise, a seventh perimeter P7 of a first (proximal) end 66 of the fourth stent-graft may be at least 3 cm, no more than 7 cm, and/or between 3 and 7 cm, and a eighth perimeter P8 of a second (distal) end 68 of the fourth stent-graft may be at least 6 cm, no more than 19 cm, and/or between 6 and 19 cm. For applications in which fourth stent-graft 26 is generally cylindrical when unconstrained in its radially-expanded state, seventh and eighth perimeters P7 and P8 are seventh and eighth diameters. For some applications, seventh and eighth perimeters P7 and P8 are equal.

For some applications, fourth stent-graft 26, when unconstrained in its radially-expanded state, has an axial length of at least 9.7 cm, no more than 18 cm, and/or between 9.7 and 18 cm. (The axial length is measured along a central longitudinal axis of the stent-graft, including in applications in which the stent-graft is curved, as described hereinbelow with reference to FIG. 1B.) For some applications, fourth stent-graft 26, when unconstrained in its radially-expanded state, has a greatest perimeter (at any axial location along the stent-graft) of at least 4.8 cm, no more than 8.5 cm, and/or between 4.8 and 8.5 cm, and/or between 3.6 and 7.3 cm.

For some applications, such dimensions allow the fourth stent-graft to be positioned in the aortic arch and/or the upper end of an ascending aorta, such as described hereinbelow with reference to FIG. 3L. For some applications, the proximal portion of the stent-graft has an average perimeter that is less than (e.g., between 40% and 70% greater than) an average perimeter of the portion of the aorta in which it is disposed (excluding expansion of the aorta due to the aneurysm, i.e., assuming the aorta were healthy).

Additional Configuration Detail

Typically, first and second stent-grafts 20 and 22 are not fixed to one other when they are in their radially-compressed states. Likewise, when third stent-graft 24 is provided, first, second, and third stent-grafts 20, 22, and 24 are typically not fixed to one other when they are in their radially-compressed states. Furthermore, when third and fourth stent-grafts 24 and 26 are provided, first, second, third, and fourth stent-grafts 20, 22, 24, and 26 are typically not fixed to one other when they are in their radially-compressed states. In other words, the stent-grafts are initially provided as separate, non-connected components, as shown in FIGS. 1A-C (although they are typically initially positioned in outer tube(s) of delivery tool(s), as described hereinbelow), which are typically assembled in situ. Typically, first and second covering element 32 and 42 are not fixed to one other when they are in their radially-compressed states. Likewise, when third stent-graft 24 is provided, first, second, and third covering element 32, 42, and 52 are typically not fixed to one other when first, second, and third stent-grafts 20, 22, and 24 are in their radially-compressed states. Furthermore, when third and fourth stent-grafts 24 and 26 are provided, first, second, third, and fourth covering elements 32, 42, 52, and 62 are typically not fixed to one other when first, second, third, and fourth stent-grafts 20, 22, 24, and 26 are in their radially-compressed states.

Reference is still made to FIGS. 1A-C. In the configurations shown in FIGS. 1A and 1C, stent-grafts 20, 22, 24, and 26 are configured (e.g., heat-set) to have generally straight longitudinal axes when unconstrained in their radially-expanded states, i.e., no forces are applied to the stent-grafts by a delivery tool, walls of a blood vessel, or otherwise. The stent-grafts typically assumed curved shapes when placed in respective blood vessels because of the force applied to the stent-grafts by the walls of the blood vessels, such as shown in FIGS. 3A-L.

In the configuration shown in FIG. 1B, stent-grafts 20, 22, 24, and 26 are configured (e.g., heat-set) to have generally curved longitudinal axes when unconstrained in their radially-expanded states, i.e., no forces are applied to the stent-grafts by a delivery tool, walls of a blood vessel, or otherwise. This curvature may help properly position the stent-grafts with respect to one another, such as shown in FIGS. 2 and 3A-L. For some applications in which the stent-grafts are curved, first lateral openings 34, second lateral openings 44, and/or third lateral opening 54 are positioned on outer portions of the curves, as shown in FIG. 1B.

For some applications, at least one the stent-grafts is generally straight, as shown in FIG. 1A, while at least another one of the stent-grafts is generally curved, as shown in FIG. 1B.

For some applications, such as in the configurations shown in FIGS. 1A and 1B, the respective covering element 42, 52, and/or 62 of one or more of second, third, and fourth stent-grafts 22, 24, and 26 does not fully cover a proximal sub-portion 70 of the support element, thereby allowing blood flow through the stent-graft, as described hereinbelow with reference to FIG. 2. Optionally, one or more of proximal sub-portions 70 is flared radially outward in a proximal direction at their proximal ends.

For some applications, such as in the configurations shown in FIG. 1C, one or more of proximal ends 46, 56, and 66 of second, third, and fourth stent-grafts 22, 24, and 26 are outwardly flared in a proximal direction when the stent-grafts are unconstrained in their radially-expanded states, i.e., no forces are applied to the stent-grafts by a delivery tool, walls of a blood vessel, or otherwise. Optionally, the stent-grafts are additionally slightly indented radially inward immediately distal to the outward flares. Typically, covering elements 42, 52, and 62 cover at least a distal portion of the outward flares. The flares enable secure anchoring of the stent-grafts to one another, such as described hereinbelow with reference to FIGS. 2 and 3F-L. The flared portions (together with radially-indented portions) may serve as interface members, and may generally have the shape of an hourglass. The radially-indented (narrower) portions may be sized to be firmly coupled with a lateral opening of another stent-graft.

For some applications, one or more of the stents both define a flare, as shown in FIG. 1C, and are curved, as shown in FIG. 1B. Alternatively or additionally, for some applications, at least one the stent-grafts defines a flare, as shown in FIG. 1C, while at least another one of the stent-grafts does not define a flare, as shown in FIGS. 1A-B.

For some applications, one or more (e.g., all) of the lateral openings are circumscribed by respective generally annular structural stent elements of the support elements.

Assembly of the Stent-Grafts

FIG. 2 is a schematic illustration of multi-component stent-graft system 10, having the configurations shown in FIG. 1-C, in an assembled state, in accordance with an application of the present invention. As mentioned above, such assembly is typically performed in situ during an implantation procedure, but such assembly may also be performed ex vivo. First, second, third, and fourth stent-grafts 20, 22, 24, and 26 are shown in FIG. 2 in their radially-expanded states. Second stent-graft 22 is configured to be disposed through first lateral opening 34, such that a portion of the second stent-graft is disposed within first stent-graft 20, and a portion of the second stent-graft is disposed outside of the first stent-graft. The first and second stent-grafts are configured such that second covering element 42 forms a blood-impervious seal with first covering element 32 around first lateral opening 34, when the second stent-graft is thus disposed through the first lateral opening, and first and second stent-grafts 20 and 22 are in their radially-expanded states. The first and second stent-grafts are securely anchored to each other. The blood-impervious seal is typically formed because support element 30 of the first stent-graft is configured to having a resting perimeter that is greater than the perimeter of the first lateral opening, such that the first lateral opening squeezes the first stent-graft when the first stent-graft expands.

For some applications, when second stent-graft 22 is disposed through first lateral opening 34 and first and second stent-grafts 20 and 22 are in their radially-expanded states, a proximal portion 82 of second support element 40 is disposed within first stent-graft 20, and second covering element 42 does not fully cover proximal portion 82, thereby allowing blood flow through the first stent-graft (i.e., the second covering element does not fully cover proximal sub-portion 70). (Optionally, proximal sub-portion 70 is flared radially outward in a proximal direction at its proximal end.) Typically, at least a distal-most portion of proximal portion 82 is covered by second covering element 42, in order to form the above-mentioned blood-impervious seal with first covering element 32. Thus, second covering element 42 may be configured to cover a distal sub-portion, and not a proximal sub-portion, of proximal portion 82.

For some applications, such as for the configurations shown in FIGS. 1A-B, second support element 40 is configured to extend into first stent-graft 20 a distance sufficient to help anchor the second stent-graft to the first stent-graft, such as at least 4 cm, no more than 10 cm, and/or between 4 and 10 cm. For some applications, proximal portion 82 has a perimeter that is sufficient to apply a radially-outward force against an inner surface of a wall of first stent-graft 20, in order to help anchor the second stent-graft to the first stent-graft. For example, an axial portion of proximal portion 82 having a length of at least 1 cm may have a perimeter that is at least 10% greater than a perimeter of a portion of the first stent-graft in which proximal portion 82 is disposed. Typically, second stent-graft 22 is deployed such that proximal portion 82 extends into the first stent-graft in a proximal direction from first lateral opening 34, as shown in FIG. 2.

For applications in which third stent-graft 24 is provided, the third stent-graft is configured to be disposed through second lateral opening 44, such that a portion of the third stent-graft is disposed within second stent-graft 22 (and, optionally, depending on the length of the portion, also within first stent-graft 20), and a portion of the third stent-graft is disposed outside of the second stent-graft. The second and third stent-grafts are configured such that third covering element 52 forms a blood-impervious seal with second covering element 42 around second lateral opening 44, when the third stent-graft is thus disposed through the second lateral opening, and second and third stent-grafts 22 and 24 are in their radially-expanded states. The second and third stent-grafts are securely anchored to each other.

For some applications, when third stent-graft 24 is disposed through second lateral opening 44 and second and third stent-grafts 22 and 24 are in their radially-expanded states, a proximal portion 92 of third support element 50 is disposed within second stent-graft 22, and third covering element 52 does not fully cover proximal portion 92, thereby allowing blood flow through the second stent-graft (i.e., the third covering element does not fully cover proximal sub-portion 70). (Optionally, proximal sub-portion 70 is flared radially outward in a proximal direction at its proximal end.) Typically, at least a distal-most portion of proximal portion 92 is covered by third covering element 52, in order to form the above-mentioned blood-impervious seal with second covering element 42. Thus, third covering element 52 may be configured to cover a distal sub-portion, and not a proximal sub-portion, of proximal portion 92.

For some applications, such as for the configurations shown in FIGS. 1A-B, third support element 50 is configured to extend into second stent-graft 22 a distance sufficient to help anchor the third stent-graft to the second stent-graft, such as at least 4 cm, no more than 10 cm, and/or between 4 and 10 cm. For some applications, proximal portion 92 has a perimeter that is sufficient to apply a radially-outward force against an inner surface of a wall of second stent-graft 22, in order to help anchor the third stent-graft to the second stent-graft. For example, an axial portion of proximal portion 92 having a length of at least 1 cm may have a perimeter that is at least 10 greater than a perimeter of a portion of the second stent-graft in which proximal portion 92 is disposed. Typically, third stent-graft 24 is deployed such that proximal portion 92 extends into the second stent-graft in a proximal direction from second lateral opening 44, such as described hereinbelow with reference to FIGS. 3H-I.

For applications in which fourth stent-graft 26 is provided, the fourth stent-graft is configured to be disposed through third lateral opening 54, such that a portion of the fourth stent-graft is disposed within third stent-graft 24 (and, optionally, depending on the length of the portion, also within second stent-graft 22, or within both second stent-graft 22 and first stent-graft 20), and a portion of the fourth stent-graft is disposed outside of the third stent-graft. The third and fourth stent-grafts are configured such that fourth covering element 62 forms a blood-impervious seal with third covering element 52 around third lateral opening 54, when the fourth stent-graft is thus disposed through the third lateral opening, and third and fourth stent-grafts 24 and 26 are in their radially-expanded states. The third and fourth stent-grafts are securely anchored to each other.

For some applications, when fourth stent-graft 26 is disposed through third lateral opening 54 and third and fourth stent-grafts 24 and 26 are in their radially-expanded states, a proximal portion 98 of fourth support element 60 is disposed within third stent-graft 24, and fourth covering element 62 does not fully cover proximal portion 98, thereby allowing blood flow through the third stent-graft (i.e., the fourth covering element does not fully cover proximal sub-portion 70). (Optionally, proximal sub-portion 70 is flared radially outward in a proximal direction at its proximal end.) Typically, at least a distal-most portion of proximal portion 98 is covered by fourth covering element 62, in order to form the above-mentioned blood-impervious seal with third covering element 52. Thus, fourth covering element 62 may be configured to cover a distal sub-portion, and not a proximal sub-portion, of proximal portion 98.

For some applications, such as for the configurations shown in FIGS. 1A-B, fourth support element 60 is configured to extend into third stent-graft 24 a distance sufficient to help anchor the third stent-graft to the second stent-graft, such as at least 4 cm, no more than 10 cm, and/or between 4 and 10 cm. For some applications, proximal portion 98 has a perimeter that is sufficient to apply a radially-outward force against an inner surface of a wall of third stent-graft 24, in order to help anchor the fourth stent-graft to the third stent-graft. For example, an axial portion of proximal portion 98 having a length of at least 1 cm may have a perimeter that is at least 10% greater than a perimeter of a portion of the third stent-graft in which proximal portion 98 is disposed. Typically, fourth stent-graft 26 is deployed such that proximal portion 98 extends into the third stent-graft in a proximal direction from third lateral opening 54, such as described hereinbelow with reference to FIGS. 3K-L.

Although FIG. 2 shows the proximal ends of the stent-grafts having the configuration shown in FIGS. 1A-B, for some applications, one or more of the stent-grafts instead has the flaring proximal end configurations shown in FIG. 1C.

For some applications, a method is provided that comprises assembling first and second stent-grafts 20 and 22, optionally third stent-graft 24, and optionally fourth stent-graft 26, as described hereinabove with reference to FIG. 2, either in situ or ex vivo.

An Exemplary Deployment Procedure for the Configuration in which the First Stent-Graft has a Single Lateral Opening Reference is made to FIGS. 3A-L, which are schematic illustrations of an exemplary transluminal delivery procedure for implanting multi-component stent-graft system 10, as configured in FIGS. 1A, 1B, 1C, and/or 2, in accordance with an application of the present invention. FIGS. 3A-L schematically show a portion of a typical aorta, including a thoracic aorta, which includes an upper part of an ascending aorta 101, an aortic arch 100, and an upper part of a supra-renal descending aorta 102. Also shown are the three branches of aortic arch 100: a brachiocephalic artery 103, a left common carotid artery 104, and a left subclavian artery 105. In addition, left and right renal arteries 106 and 107 are shown.

In this exemplary procedure, the stent-grafts of system 10 are transvascularly (typically percutaneously) introduced into the thoracic aorta via one of the iliac arteries, while the stent-grafts are positioned in one or more outer tubes of a delivery tool in their radially-compressed states. Alternatively, for some applications, one or more of the stent-grafts are deployed via a right subclavian artery, such as described hereinbelow with reference to FIG. 9D.

Deployment of the First Stent-Graft

The exemplary procedure begins with the advancing of a guidewire 120 up descending aorta 102 and into a first one of the branches of aortic arch 100, such as left subclavian artery 105, as shown in FIG. 3A.

First stent-graft 20 is initially positioned in its radially-compressed state within an outer tube 130 of a delivery tool, typically near a distal end 132 of the outer tube (e.g., such that at least one end of stent-graft 20 is within a distance of distal end 132, which distance equals the sum of 2 cm and an axial length of the first stent-graft). Outer tube 130 is advanced over guidewire 120, until first stent-graft 20 is partially disposed in left subclavian artery 105 and partially disposed in the upper part of descending aorta 102, as shown in FIG. 3B. The guidewire is withdrawn, leaving outer tube 130 in place.

As shown in FIG. 3C, the first stent-graft is held in place as outer tube 130 is withdrawn, thereby delivering the first stent-graft from the outer tube. Optionally, techniques for holding the first stent-graft in place may be used that are described hereinbelow with reference to FIGS. 10 and 11A-E or FIGS. 12A-C. First stent-graft 20 typically self-expands, until it assumes its radially-expanded state, upon reaching its maximum unconstrained size, and/or being constrained from further expansion by the wall of the blood vessels. Alternatively, the first stent-graft (and/or the second, third, and/or fourth stent-grafts, as described hereinbelow) is delivered using an over-the-wire (OTW) approach, in which the guidewire is left in place until the stent-graft is expanded, and thereafter the guidewire is withdrawn.

A proximal portion 111 of first stent-graft 20, including proximal end 36, is positioned in the upper part of descending aorta 102, and a distal portion 112 of first stent-graft 20 is positioned in left subclavian artery 105. First lateral opening 34 is disposed in aortic arch 100 facing upstream, generally toward ascending aorta 101, in a vicinity of the bifurcation of aortic arch 100 and left subclavian artery 105. For some applications, proper rotational alignment and/or axial orientation of the first lateral opening is achieved using fluoroscopy. For example, first stent-graft 20 may comprise one or more radiopaque markers in a vicinity of (e.g., on a periphery of) the first lateral opening.

Deployment of the Second Stent-Graft

Figure 3D:
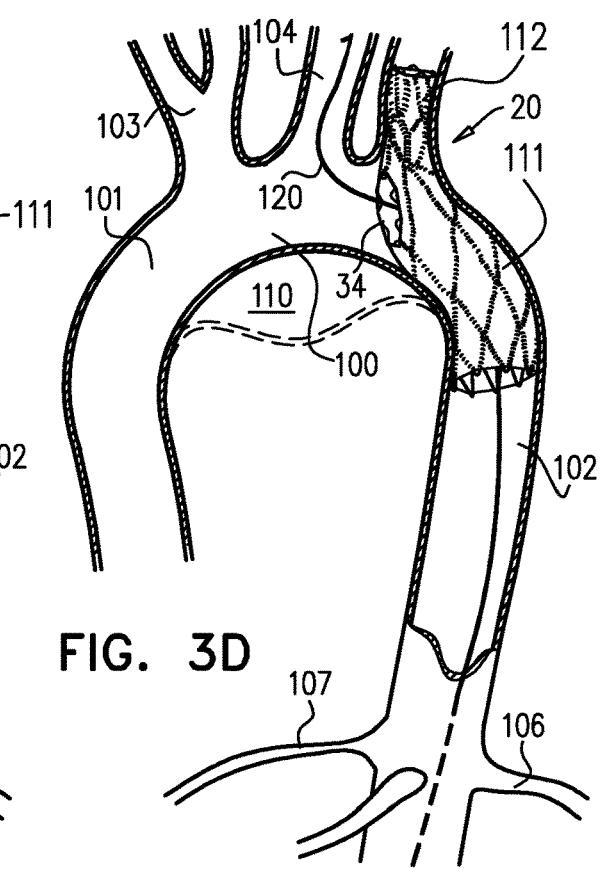

A guidewire (either the same guidewire 120 used to deploy the first stent-graft, or a second guidewire) is advanced up descending aorta 102, through a proximal portion of first-stent-graft 20, out of first lateral opening 34, and into a second one of the branches of aortic arch 100, such as left common carotid artery 104, as shown in FIG. 3D.

Figure 3E:
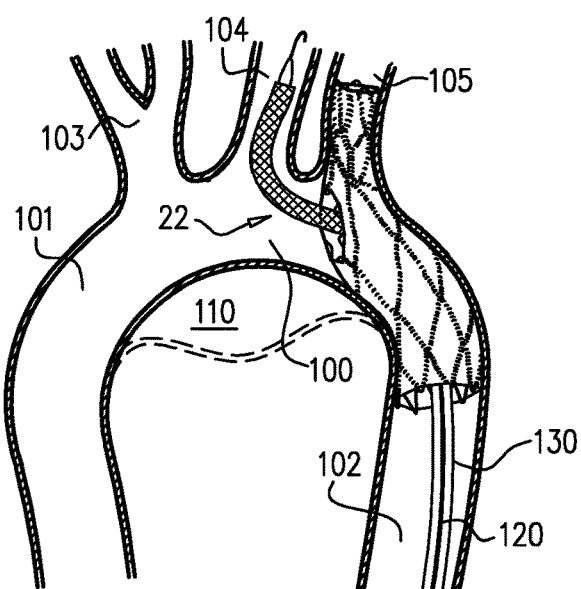

Second stent-graft 22 is positioned in its radially-compressed state within an outer tube of a delivery tool (either the same outer tube 130 used to deploy the first stent-graft, or a second outer tube), typically near distal end 132 of the outer tube (e.g., such that at least one end of stent-graft 22 is within a distance of distal end 132, which distance equals the sum of 2 cm and an axial length of the first stent-graft). Outer tube 130 is advanced over guidewire 120, until second stent-graft 22 is partially disposed in left common carotid artery 104 and partially disposed within radially-expanded first stent-graft 20 in the upper part of descending aorta 102, as shown in FIG. 3E. The guidewire is withdrawn, leaving outer tube 130 in place.

Figure 3F:
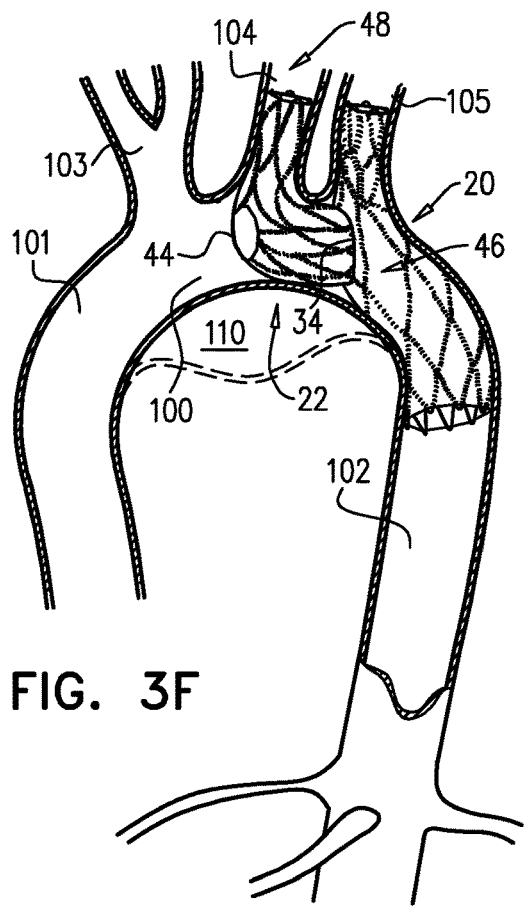

As shown in FIG. 3F, the second stent-graft is held in place as outer tube 130 is withdrawn, thereby delivering the second stent-graft from the outer tube. Optionally, techniques for holding the second stent-graft in place may be used that are described hereinbelow with reference to FIGS. 10 and 11A-E or FIGS. 12A-C. Second stent-graft 22 typically self-expands, until it assumes its radially-expanded state, upon reaching its maximum unconstrained size, and/or being constrained from further expansion by the wall of the blood vessels.

A proximal portion of second stent-graft 22, including proximal end 46, is positioned within first stent-graft 20 in the upper part of descending aorta 102, and a distal portion of second stent-graft 22, including distal end 48, is positioned in left common carotid artery 104. For application in which third stent-graft 24 is provided, and second stent-graft 22 is shaped so as to define second lateral opening 44, the second lateral opening is disposed in aortic arch 100 facing upstream, generally toward ascending aorta 101, in a vicinity of the bifurcation of aortic arch 100 and left common carotid artery 104.

For some applications, proper rotational alignment and/or axial orientation of the second lateral opening is achieved using fluoroscopy. For example, second stent-graft 22 may comprise one or more radiopaque markers in a vicinity (e.g., on a periphery of) the second lateral opening.

Second stent-graft 22 is thus adapted for transluminal delivery in its radially-compressed state through a portion of first stent-graft 20 and first lateral opening 34, while the first stent-graft is in its radially-expanded state.

Deployment of the Third Stent-Graft

Figure 3G:
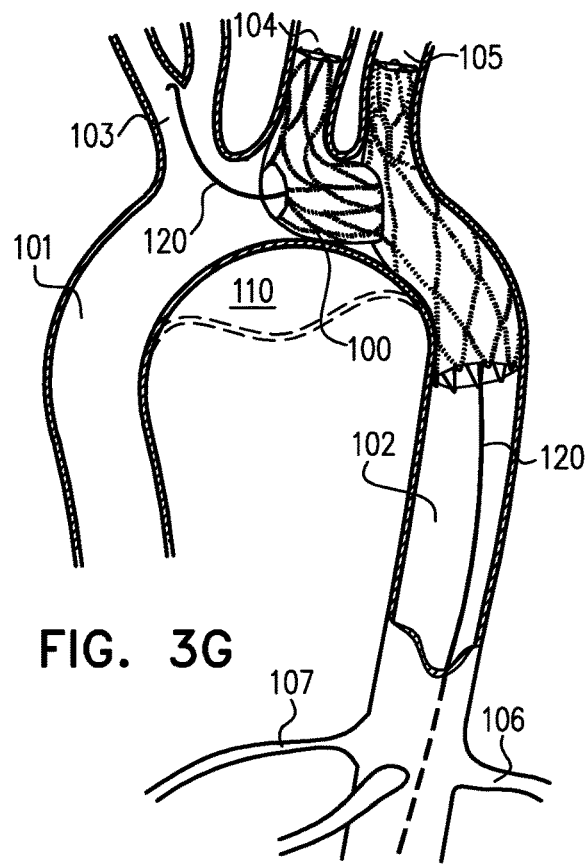

For applications in which third stent-graft 24 is provided, a guidewire (either the same guidewire 120 used to deploy the first and/or second stent-grafts, or an additional guidewire) is advanced up descending aorta 102 and into a third one of the branches of aortic arch 100, such as brachiocephalic artery 103, as shown in FIG. 3G.

Figure 3H:
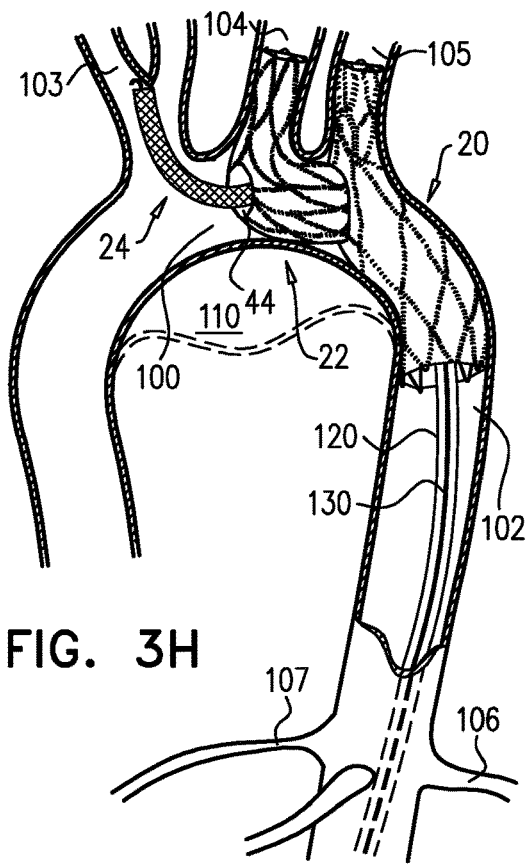

Third stent-graft 24 is positioned in its radially-compressed state within an outer tube of a delivery tool (either the same outer tube 130 used to deploy the first and/or second stent-grafts, or another outer tube), typically near distal end 132 of the outer tube (e.g., such that at least one end of stent-graft 24 is within a distance of distal end 132, which distance equals the sum of 2 cm and an axial length of the first stent-graft). Outer tube 130 is advanced over guidewire 120, until third stent-graft 24 is partially disposed in brachiocephalic artery 103 and partially disposed within radially-expanded second stent-graft 22 in aortic arch 100, as shown in FIG. 3H. The guidewire is withdrawn, leaving outer tube 130 in place.

Figure 3I:
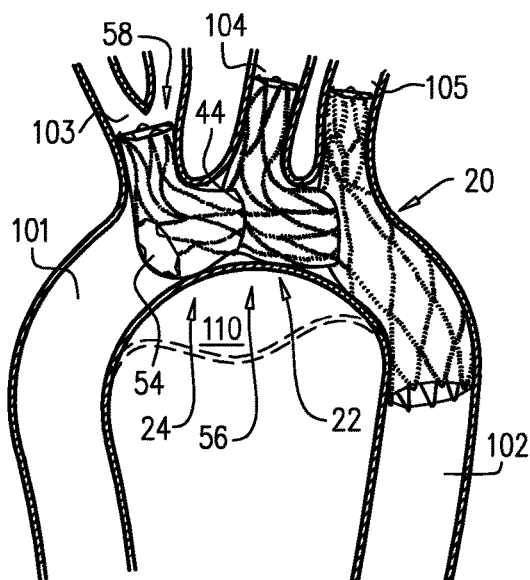

As shown in FIG. 3I, the third stent-graft is held in place as outer tube 130 is withdrawn, thereby delivering the third stent-graft from the outer tube. Optionally, techniques for holding the third stent-graft in place may be used that are described hereinbelow with reference to FIGS. 10 and 11A-E or FIGS. 12A-C. Third stent-graft 24 typically self-expands, until it assumes its radially-expanded state, upon reaching its maximum unconstrained size, and/or being constrained from further expansion by the wall of the blood vessels.

A proximal portion of third stent-graft 24 is positioned within second stent-graft 22 in aortic arch 100, and a distal portion of third stent-graft 24, including distal end 58, is positioned in brachiocephalic artery 103. For application in which fourth stent-graft 26 is provided, and third stent-graft 24 is shaped so as to define third lateral opening 54, the third lateral opening is disposed in aortic arch 100 facing upstream, generally toward ascending aorta 101, in a vicinity of the bifurcation of aortic arch 100 and brachiocephalic artery 103. For some applications, proper rotational alignment and/or axial orientation of the third lateral opening is achieved using fluoroscopy. For example, third stent-graft 24 may comprise one or more radiopaque markers in a vicinity (e.g., on a periphery of) the third lateral opening.

Third stent-graft 24 is thus adapted for transluminal delivery in its radially-compressed state through, sequentially, (a) a portion of first stent-graft 20, (b) first lateral opening 34, (c) a portion of second stent-graft 22, and (d) second lateral opening 44, while the first and second stent-grafts are in their radially-expanded states.

Deployment of the Fourth Stent-Graft

Figure 3J:
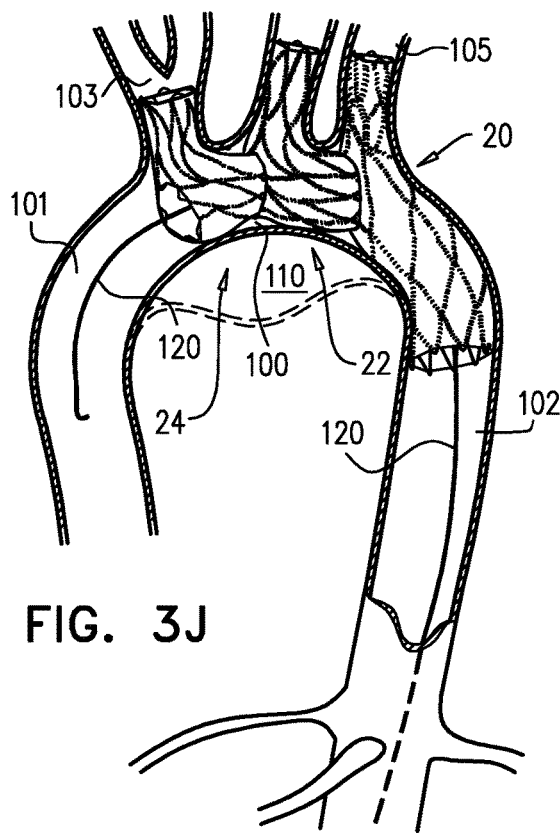

For applications in which fourth stent-graft 26 is provide, a guidewire (either the same guidewire 120 used to deploy the first, second, and/or third stent-grafts, or an additional guidewire) is advanced up descending aorta 102 and into the upper part of ascending aorta 101, as shown in FIG. 3J.

Figure 3K:
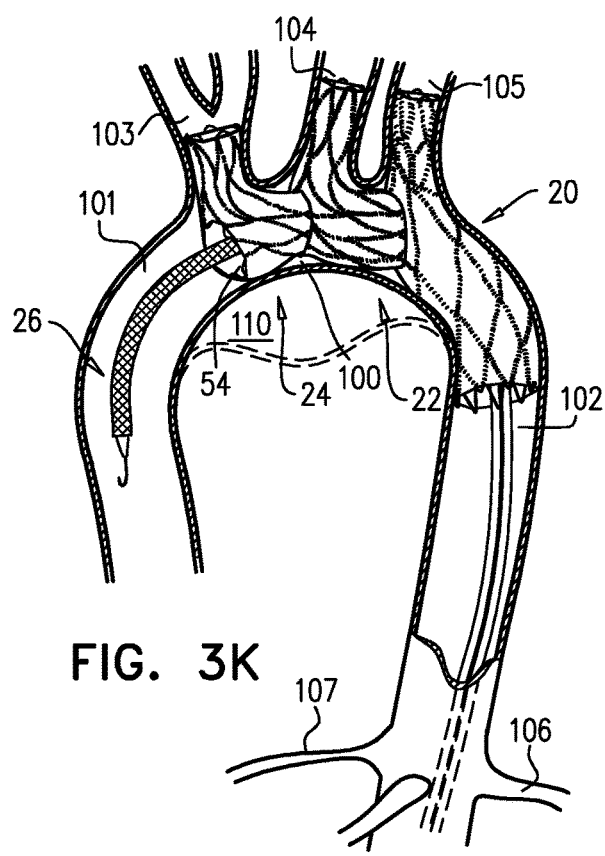

Fourth stent-graft 26 is positioned in its radially-compressed state within an outer tube of a delivery tool (either the same outer tube 130 used to deploy the first, second, and/or third stent-grafts, or an additional outer tube), typically near distal end 132 of the outer tube (e.g., such that at least one end of stent-graft 26 is within a distance of distal end 132, which distance equals the sum of 2 cm and an axial length of the first stent-graft). Outer tube 130 is advanced over guidewire 120, until fourth stent-graft 26 is partially disposed in the upper part of ascending aorta 101 and partially disposed within radially-expanded third stent-graft 24 in aortic arch 100, as shown in FIG. 3K. The guidewire is withdrawn, leaving outer tube 130 in place.

Figure 3L:
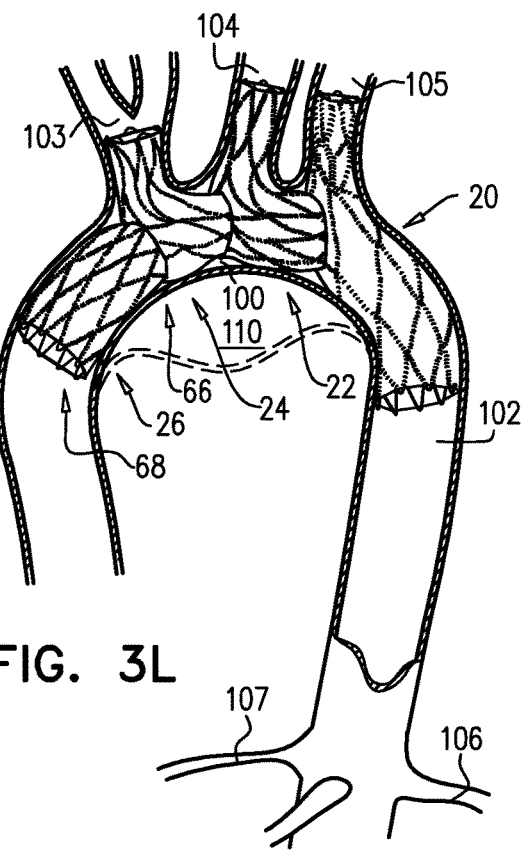

As shown in FIG. 3L, the fourth stent-graft is held in place as outer tube 130 is withdrawn, thereby delivering the fourth stent-graft from the outer tube. Optionally, techniques for holding the fourth stent-graft in place may be used that are described hereinbelow with reference to FIGS. 10 and 11A-E or FIGS. 12A-C. Fourth stent-graft 26 typically self-expands, until it assumes its radially-expanded state, upon reaching its maximum unconstrained size, and/or being constrained from further expansion by the wall of the blood vessels.

A proximal portion of fourth stent-graft 26 is positioned within third stent-graft 24 (and, optionally, in second stent-graft 22) in aortic arch 100, and a distal portion of fourth stent-graft 26, including distal end 68, is positioned in aortic arch 100 and/or the upper part of ascending aorta 101.

Fourth stent-graft 26 is thus adapted for transluminal delivery when in its radially-compressed state through, sequentially, (a) a portion of first stent-graft 20, (b) first lateral opening 34, (c) a portion of second stent-graft 22, (d) second lateral opening 44, (e) a portion of third stent-graft 24, and (f) third lateral opening 54 while first, second, and third stent-grafts 20, 22, and 24 are in their radially-expanded states.

As can be seen in FIG. 3L, upon deployment of all four stent-grafts, multi-component stent-graft system 10 defines a blood-flow path from ascending aorta 101, over aortic arch 100, and to descending aorta 102. Multi-component stent-graft system 10 additionally provides blood-flow paths to the three branches of the aortic arch: brachiocephalic artery 103, left common carotid artery 104, and left subclavian artery 105.

First Stent-Graft Having Three Lateral Openings

Reference is now made to FIG. 4, which is a schematic illustration of another configuration of multi-component stent-graft system 10, in accordance with an application of the present invention. In this configuration, multi-component stent-graft system 10 comprises (a) first stent-graft 20, (b) second stent-graft 22, (c) third stent-graft 24, and (d) fourth stent-graft 26, typically configured as described hereinbelow. Except as described below, the stent-grafts are generally similar to the configurations of the stent-grafts described hereinabove with reference to FIGS. 1A-C and 2. The stent-grafts are configured to assume radially-compressed states, such as when initially positioned in one or more outer tubes of one or more delivery tools, as described hereinbelow with reference to FIGS. 6A, 6B, 6E, and 6G, and to assume radially-expanded states upon being deployed from the outer tube(s), as described hereinbelow with reference to FIGS. 6B-D and 6F-H. FIG. 4 shows the stent-grafts in their radially-expanded states. For some applications, the stent-grafts are relaxed in their radially-expanded states. For some applications, the stent-grafts are configured to be self-expanding. For example, they may be heat-set to assume their radially-expanded states.

The First Stent-Graft

In the configuration shown in FIG. 4, first covering element 32 and first support element 30 are shaped so as to together define three (e.g., exactly three) first lateral openings 34 through first stent-graft 20 when the first stent-graft is in its radially-expanded state:

a proximal superior first lateral opening 34A;
a distal superior first lateral opening 34B; and
a distal inferior first lateral opening 34C.

Typically, when first stent-graft 20 is unconstrained in its radially-expanded state, proximal and distal superior first lateral openings 34A and 34B face in a first radial direction, and distal inferior first lateral opening 34C faces in a second radially direction generally circumferentially opposite the first radial direction. For example, if the stent-graft is viewed from one end, proximal and distal superior first lateral openings 34A and 34B may be disposed at between 11 o'clock and 1 o'clock (e.g., at 12 o'clock), and distal inferior first lateral opening 34C may disposed at between 5 o'clock and 7 o'clock (e.g., at 6 o'clock).

Typically, distal inferior first lateral opening 34C is not axially aligned with either of proximal superior first lateral opening 34A or distal superior first lateral opening 34B. Typically, distal inferior first lateral opening 34C does not axially overlap with either of proximal superior first lateral opening 34A or distal superior first lateral opening 34B.

For some applications, stent-graft 20 narrows in a vicinity of proximal superior first lateral opening 34A and/or distal superior first lateral opening 34B, with respect to a portion of stent-graft 20 proximal to the proximal superior first lateral opening 34A (i.e., the perimeter is less at one or both of the lateral openings than in the more proximal portion). Such narrowing may increase the maneuverability of third and/or fourth stent-grafts 24 and 26 when advancing these stent-grafts into left common carotid artery 104 and left subclavian artery 105, by providing more space between the superior lateral openings and the bifurcations of these arteries.

For some applications, when first stent-graft 20 is unconstrained in its radially-expanded state, first perimeter P1 of first end 36 of the first stent-graft is greater than second perimeter P2 of second end 38 of the first stent-graft, and/or a first cross-sectional area of the first end 36 is greater than a second cross-sectional area of second end 38. For example, first perimeter P1 may equal at least 150% of second perimeter P2, such as at least 250%, or at least 400%, and/or the first cross-sectional area may equal at least 225% of the second cross-sectional area, such as at least 625%, or at least 1600%.

For example, first perimeter P1 may be at least 7.5 cm, no more than 15 cm, and/or between 7.5 and 15 cm, such as at least 9 cm, no more than 13 cm, and/or between 9 and 13 cm, and second perimeter P2 may be at least 2.5 cm, no more than 5.7 cm, and/or between 2.5 and 5.7 cm, such as at least 3 cm, no more than 4.5 cm, and/or between 3 and 4.5 cm.

For some applications, when first stent-graft 20 is unconstrained in its radially-expanded state, a perimeter of each of proximal superior first lateral opening 34A and distal superior first lateral opening 34B is at least 2.5 cm, no more than 5 cm, and/or between 2.5 and 5 cm, and a perimeter of distal inferior first lateral opening 34C is at least 4.5 cm, no more than 12 cm, and/or between 4.5 and 12 cm.

For some applications, when first stent-graft 20 is unconstrained in its radially-expanded state, a perimeter of distal inferior first lateral opening 34C is at least 25%, e.g., at least 40%, or at least 60% of first perimeter P1, and/or at least 50%, e.g., at least 75%, or at least 100% of second perimeter P2. For some applications, first perimeter P1 does not equal second perimeter P2, and the perimeter of distal inferior first lateral opening 34C is at least 60% of the lesser of first and second perimeters P1 and P2.

For some applications, first stent-graft 20, when unconstrained in its radially-expanded state, has an axial length of at least 15 cm, no more than 40 cm, and/or between 15 and 40 cm. (The axial length is measured along a central longitudinal axis of the stent-graft, including in applications in which the stent-graft is curved.) For some applications, first stent-graft 20, when unconstrained in its radially-expanded state, has a greatest perimeter (at any axial location along the stent-graft) of at least 12 cm, no more than 21 cm, and/or between 12 and 21 cm.

For some applications, a closest axial distance D1 between proximal superior first lateral opening 34A and distal superior first lateral opening 34B is between 0.5 and 2 cm. For some applications, a distance D2 between the centers of distal superior first lateral opening 34B and distal inferior first lateral opening 34C is between 0 and 5 cm.

Figure 6A:
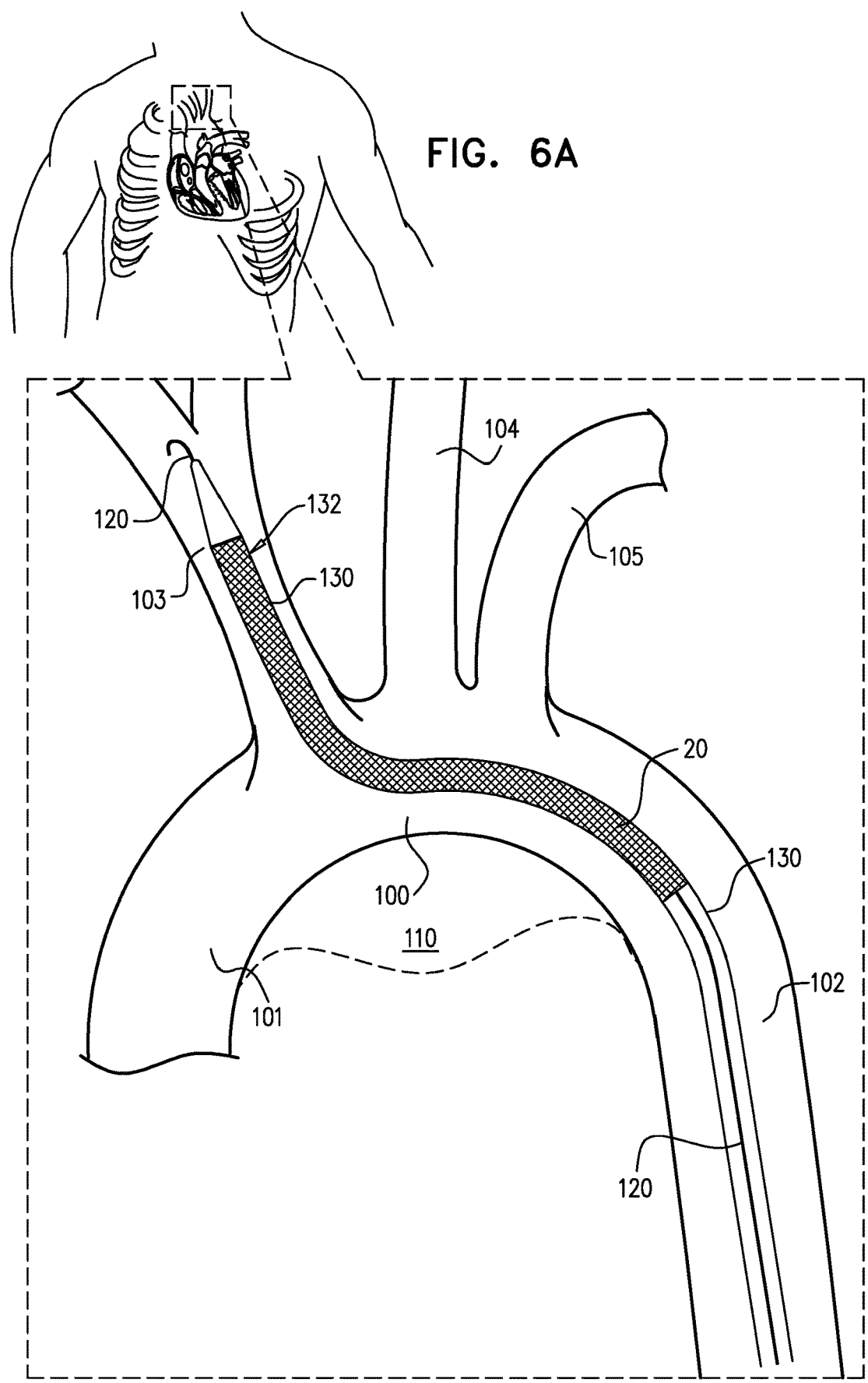
FIGS. 6A-H are schematic illustrations of an exemplary transluminal delivery procedure for implanting the multi-component stent-graft system of FIGS. 4 and 5, in accordance with an application of the present invention.
Figure 6B:
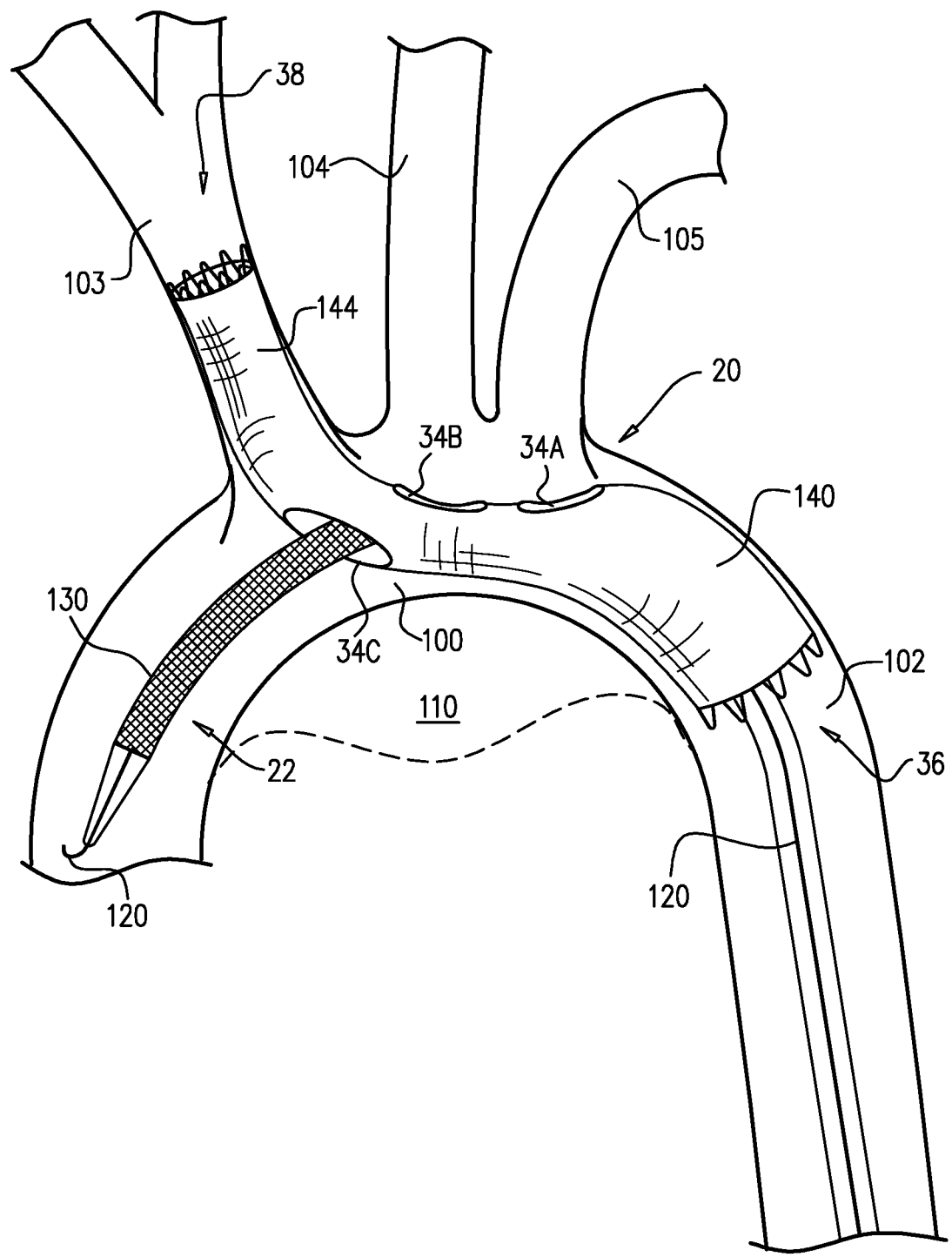

For some applications, such dimensions allow the first stent-graft to be positioned such that (a) a proximal, radially larger, portion of the stent-graft, including the proximal end thereof, is disposed in the aorta downstream from the bifurcation with the left subclavian artery, at least partially in the upper part of the descending aorta, (b) a distal, radially smaller, portion of the stent-graft, including the distal end thereof, is disposed in the brachiocephalic artery, and (c) a middle portion of the stent-graft is positioned in the aortic arch, such as described hereinbelow with reference to FIG. 6B. For some applications, the proximal portion of the stent-graft has an average perimeter that is greater than (e.g., between 5% and 15% greater than) an average perimeter of the portion of the aorta in which it is disposed (excluding expansion of the aorta due to the aneurysm, i.e., assuming the aorta were healthy). For some applications, the distal portion of the stent-graft has an average perimeter that is greater than (e.g., between 5% and 15% greater than) the average perimeter of the portion of the brachiocephalic artery in which it is disposed. For some applications, the middle portion of the stent-graft has an average perimeter that is less than (e.g., between 50% and 70% less than) an average perimeter of the portion of the aortic arch in which it is disposed (excluding expansion of the aortic arch due to the aneurysm, i.e., assuming the aortic arch were healthy).

The Second Stent-Graft

In the configuration shown in FIG. 4, second covering element 42 and second support element 40 of second stent-graft 22 are shaped so as to together define no lateral openings.

Typically, proximal end 46 of second stent-graft 22 is outwardly flared in a proximal direction when the stent-graft is unconstrained in its radially-expanded state. Optionally, the stent-graft is additionally slightly indented radially inward immediately distal to the outward flare. Typically, covering element 42 covers at least a distal portion of the outward flare. The flare enables secure anchoring of the second stent-graft to the first stent-graft, such as described hereinbelow with reference to FIGS. 5 and 6D.

For some applications, when second stent-graft 22 is unconstrained in its radially-expanded state, fourth perimeter P4 of second (distal) end 48 of the second stent-graft is substantially greater than third perimeter P3 of first (proximal) end 46 of the second stent-graft, such as at least 150% of P3, e.g., at least 200%. For some applications, third perimeter P3 is at least 3 cm, no more than 7 cm, and/or between 3 and 7 cm. For some applications, fourth perimeter P4 is at least 6 cm, no more than 19 cm, and/or between 6 and 19 cm.

For some applications, second stent-graft 22, when unconstrained in its radially-expanded state, has an axial length of at least 4 cm, no more than 20 cm, and/or between 4 and 20 cm. (The axial length is measured along a central longitudinal axis of the stent-graft, including in applications in which the stent-graft is curved.) For some applications, second stent-graft 22, when unconstrained in its radially-expanded state, has a greatest perimeter (at any axial location along the stent-graft) of at least 6 cm, no more than 10 cm, and/or between 6 and 10 cm.

For some applications, such dimensions allow the second stent-graft to be positioned such that (a) a proximal, radially smaller, portion of the stent-graft, including the proximal end thereof, is disposed in the aortic arch in the first stent-graft, and (b) a distal, radially larger, portion of the stent-graft, including the distal end thereof, is disposed in the aortic arch and/or upper part of descending aorta, such as described hereinbelow with reference to FIG. 6D. For some applications, the proximal portion of the stent-graft has an average perimeter that is less than (e.g., between 30% and 70% less than) an average perimeter of the portion of the aortic arch in which it is disposed (excluding expansion of the aortic arch due to the aneurysm, i.e., assuming the aortic arch were healthy) and at least 10% greater than the perimeter of distal inferior first lateral opening 34C of the first stent-graft. For some applications, the distal portion of the stent-graft has an average perimeter that is greater than (e.g., between 5% and 15% greater than) the average perimeter of the portion of the aorta in which it is disposed (excluding expansion of the aorta due to the aneurysm, i.e., assuming the aorta were healthy).

The Third and Fourth Stent-Grafts

For some applications of the configuration shown in FIG. 4, third and fourth stent-grafts 24 and 26 are identical or generally similar in shape and dimensions. In the configuration shown in FIG. 4, third covering element 52 and third support element 50 of third stent-graft 24 are shaped so as to together define no lateral openings, and fourth covering element 62 and fourth support element 60 of fourth stent-graft 26 are shaped so as to together define no lateral openings.

Typically, proximal ends 56 and 66 of third and fourth stent-grafts 24 and 26 are outwardly flared in a proximal direction when the stent-grafts are unconstrained in their radially-expanded state. Optionally, the stent-grafts are additionally slightly indented radially inward immediately distal to the outward flares. Typically, covering elements 52 and 62 cover at least a distal portion of the outward flares. The flares enable secure anchoring of the third and fourth stent-grafts to the first stent-graft, such as described hereinbelow with reference to FIGS. 6F and 6H.

For some applications, when third stent-graft 24 is unconstrained in its radially-expanded state, fifth perimeter P5 of first (proximal) end 56 of the third stent-graft is approximately equal to, or slightly greater than, sixth perimeter P6 of second (distal) end 58 of the third stent-graft, such as within 90% to 130% of P6. Similarly, for some applications, when fourth stent-graft 26 is unconstrained in its radially-expanded state, seventh perimeter P7 of first (proximal) end 66 of the fourth stent-graft is approximately equal to, or slightly greater than, eighth perimeter P8 of second (distal) end 68 of the fourth stent-graft, such as within 90% to 130% of P8. For some applications, each of fifth perimeter P5, sixth perimeter P6, seventh perimeter P7, and eighth perimeter P8 is at least 2.5 cm, no more than 6.3 cm, and/or between 2.5 and 6.3 cm.

For some applications, each of third and fourth stent-grafts 24 and 26, when unconstrained in their radially-expanded states, has an axial length of at least 3 cm, no more than 10 cm, and/or between 3 and 10 cm. (The axial length is measured along a central longitudinal axis of the stent-grafts, including in applications in which the stent-grafts are curved.) For some applications, each of third and fourth stent-grafts 24 and 26, when unconstrained in their radially-expanded states, has a greatest perimeter (at any axial location along the stent-grafts) of at least 2.5 cm, no more than 6.3 cm, and/or between 2.5 and 6.3 cm.

For some applications, such dimensions allow the third stent-graft to be positioned such that (a) a proximal portion of the stent-graft is disposed in the aorta in the first stent-graft, and (b) a distal portion of the stent-graft, including the distal end thereof, is disposed in the left common carotid artery, such as described hereinbelow with reference to FIG. 6F. For some applications, the proximal portion of the stent-graft has an average perimeter that is less than (e.g., between 30% and 70% less than) an average perimeter of the portion of the aortic arch in which it is disposed (excluding expansion of the aortic arch due to the aneurysm, i.e., assuming the aortic arch were healthy). For some applications, the distal portion of the stent-graft has an average perimeter that is greater than (e.g., between 5% and 15% greater than) the average perimeter of the portion of the left common carotid artery in which it is disposed.

For some applications, such dimensions allow the fourth stent-graft to be positioned such that (a) a proximal portion of the stent-graft is disposed in the aorta in the first stent-graft, and (b) a distal portion of the stent-graft, including the distal end thereof, is disposed in the left subclavian artery, such as described hereinbelow with reference to FIG. 6H. For some applications, the proximal portion of the stent-graft has an average perimeter that is less than (e.g., between 30% and 70% less than) an average perimeter of the portion of the aortic arch in which it is disposed (excluding expansion of the aortic arch due to the aneurysm, i.e., assuming the aortic arch were healthy). For some applications, the distal portion of the stent-graft has an average perimeter that is greater than (e.g., between 5% and 10% greater than) the average perimeter of the portion of the left subclavian artery in which it is disposed.

Additional Configuration Detail

For some applications, stent-grafts 20, 22, 24, and 26 are configured (e.g., heat-set) to have generally straight longitudinal axes when unconstrained in their radially-expanded states, i.e., no forces are applied to the stent-grafts by a delivery tool, walls of a blood vessel, or otherwise. The stent-grafts typically assumed curved shapes when placed in respective blood vessels because of the force applied to the stent-grafts by the walls of the blood vessels, such as shown in FIGS. 6A-H.

For other applications, stent-grafts 20, 22, 24, and 26 are configured (e.g., heat-set) to have generally curved longitudinal axes when unconstrained in their radially-expanded states, i.e., no forces are applied to the stent-grafts by a delivery tool, walls of a blood vessel, or otherwise. This curvature may help properly position the stent-grafts with respect to one another, such as shown in FIGS. 5 and 6A-H. This configuration is similar to the curved configuration shown in FIG. 1B. For some applications, at least one the stent-grafts is generally straight, while at least another one of the stent-grafts is generally curved.

Typically, first and second stent-grafts 20 and 22 are not fixed to one other when they are in their radially-compressed states. Likewise, first, second, and third stent-grafts 20, 22, and 24 are typically not fixed to one other when they are in their radially-compressed states. Furthermore, first, second, third, and fourth stent-grafts 20, 22, 24, and 26 are typically not fixed to one other when they are in their radially-compressed states. In other words, the stent-grafts are initially provided as separate, non-connected components, as shown in FIG. 4 (although they are typically initially positioned in outer tube(s) of delivery tool(s), as described hereinbelow), which are typically assembled in situ. Typically, first and second covering element 32 and 42 are not fixed to one other when they are in their radially-compressed states. Likewise, first, second, and third covering element 32, 42, and 52 are typically not fixed to one other when first, second, and third stent-grafts 20, 22, and 24 are in their radially-compressed states. Furthermore, first, second, third, and fourth covering elements 32, 42, 52, and 62 are typically not fixed to one other when first, second, third, and fourth stent-grafts 20, 22, 24, and 26 are in their radially-compressed states.

For some applications, one or more (e.g., all) of the lateral openings are circumscribed by respective generally annular structural stent elements of the support elements.

Assembly of the Stent-Grafts

Figure 5:
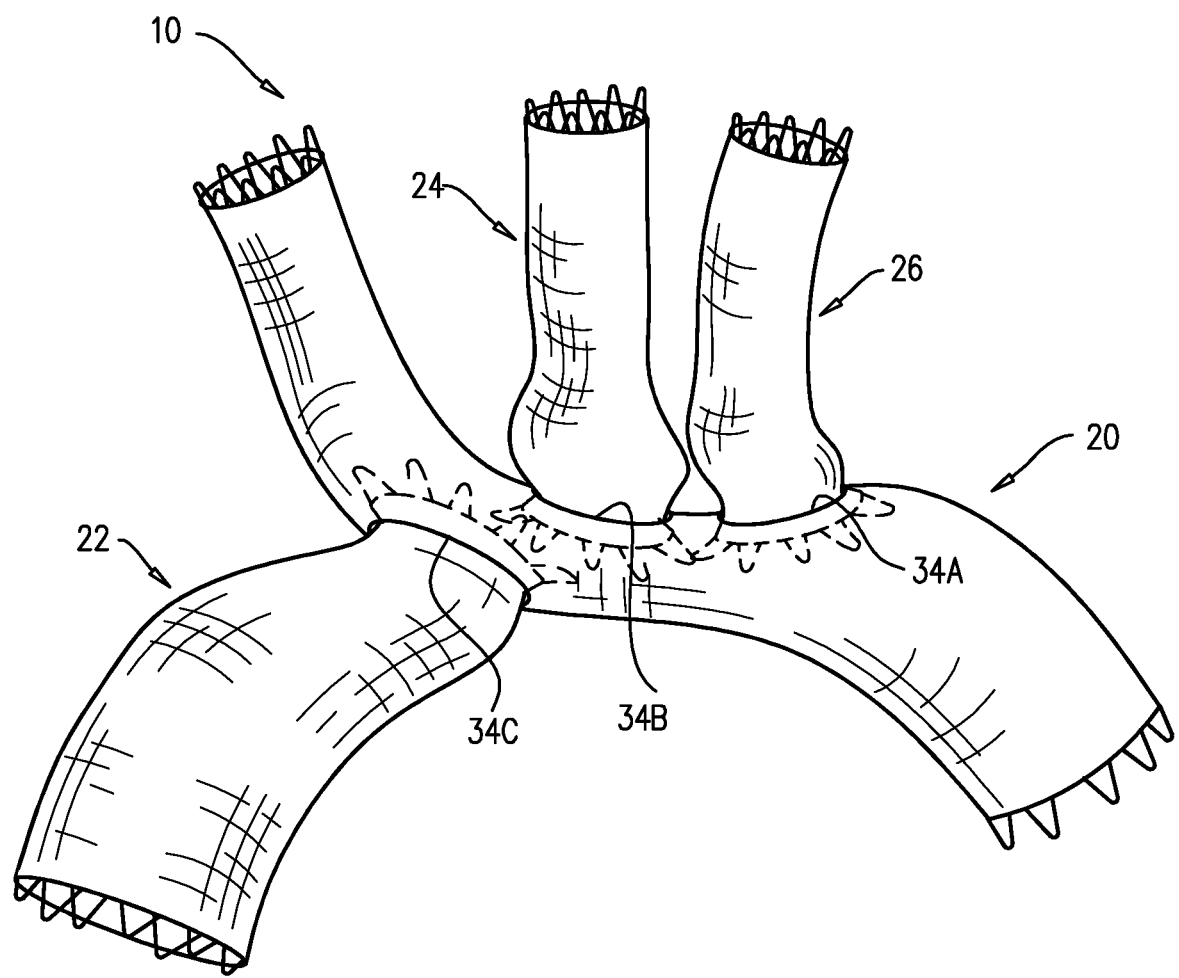
FIG. 5 is a schematic illustration of the multi-component stent-graft system of FIG. 4 in an assembled state, in accordance with an application of the present invention.

FIG. 5 is a schematic illustration of multi-component stent-graft system 10, having the configuration described with reference to FIG. 4, in an assembled state, in accordance with an application of the present invention. As mentioned above, such assembly is typically performed in situ during an implantation procedure, but such assembly may also be performed ex vivo. First, second, third, and fourth stent-grafts 20, 22, 24, and 26 are shown in FIG. 5 in their radially-expanded states. Second stent-graft 22 is configured to be disposed through distal inferior first lateral opening 34C, such that a portion (e.g., the flared portion) of the second stent-graft is disposed within first stent-graft 20, and a portion of the second stent-graft is disposed outside of the first stent-graft. The first and second stent-grafts are configured such that second covering element 42 forms a blood-impervious seal with first covering element 32 around distal inferior first lateral opening 34C, when the second stent-graft is thus disposed through the distal inferior first lateral opening, and first and second stent-grafts 20 and 22 are in their radially-expanded states. The first and second stent-grafts are securely anchored to each other. The blood-impervious seal is typically formed because support element 30 of the first stent-graft is configured to having a resting perimeter that is greater than the perimeter of the distal inferior first lateral opening, such that the distal inferior first lateral opening squeezes the second stent-graft when the second stent-graft expands.

Third stent-graft 24 is configured to be disposed through distal superior first lateral opening 34B, such that a portion (e.g., the flared portion) of the third stent-graft is disposed within first stent-graft 20, and a portion of the third stent-graft is disposed outside of the first stent-graft. The first and third stent-grafts are configured such that third covering element 52 forms a blood-impervious seal with first covering element 32 around distal superior first lateral opening 34B, when the third stent-graft is thus disposed through the distal superior first lateral opening, and first and third stent-grafts 20 and 24 are in their radially-expanded states. The first and third stent-grafts are securely anchored to each other.

Fourth stent-graft 26 is configured to be disposed through proximal superior first lateral opening 34A, such that a portion (e.g., the flared portion) of the fourth stent-graft is disposed within first stent-graft 20, and a portion of the fourth stent-graft is disposed outside of the first stent-graft. The first and fourth stent-grafts are configured such that fourth covering element 62 forms a blood-impervious seal with first covering element 32 around proximal superior first lateral opening 34A, when the fourth stent-graft is thus disposed through the proximal superior first lateral opening, and first and fourth stent-grafts 20 and 26 are in their radially-expanded states. The first and fourth stent-grafts are securely anchored to each other.

For some applications, a method is provided that comprises assembling first, second, third, and fourth stent-grafts 20, 22, 24, and 26, as described hereinabove with reference to FIG. 5, either in situ or ex vivo.

An Exemplary Deployment Procedure for the Configuration in which the First Stent-Graft has Three Lateral Openings Reference is made to FIGS. 6A-H, which are schematic illustrations of an exemplary transluminal delivery procedure for implanting multi-component stent-graft system 10, as configured in FIGS. 4 and 5, in accordance with an application of the present invention. In this exemplary procedure, the stent-grafts of system 10 are transvascularly (typically percutaneously) introduced into aortic arch 100 via one of the iliac arteries, while the stent-grafts are positioned in one or more outer tubes of a delivery tool in their radially-compressed states. Alternatively, for some applications, one or more of the stent-grafts are deployed via a right subclavian artery, such as described hereinbelow with reference to FIG. 9D.

Deployment of the First Stent-Graft

First stent-graft 20 is initially positioned in its radially-compressed state within outer tube 130 of a delivery tool, typically near distal end 132 of the outer tube (e.g., such that at least one end of stent-graft 20 is within a distance of distal end 132, which distance equals the sum of 2 cm and an axial length of the first stent-graft). The exemplary procedure begins with the advancing of guidewire 120 up descending aorta 102 and into a first one of the branches of the aortic arch, such as brachiocephalic artery 103. Outer tube 130 is advanced over guidewire 120, until first stent-graft 20 is partially disposed in brachiocephalic artery 103, partially disposed in aortic arch 100, and partially disposed an upper part of descending aorta 102, as shown in FIG. 6A. The guidewire is withdrawn, leaving outer tube 130 in place.

As shown in FIG. 6B, the first stent-graft is held in place as outer tube 130 is withdrawn, thereby delivering the first stent-graft from the outer tube. Optionally, techniques for holding the first stent-graft in place may be used that are described hereinbelow with reference to FIGS. 10 and 11A-E or FIGS. 12A-C. First stent-graft 20 typically self-expands, until it assumes its radially-expanded state, upon reaching its maximum unconstrained size, and/or being constrained from further expansion by the wall of the blood vessels. Alternatively, the first stent-graft (and/or the second, third, and/or fourth stent-grafts, as described hereinbelow) is delivered using an over-the-wire (OTW) approach, in which the guidewire is left in place until the stent-graft is expanded, and thereafter the guidewire is withdrawn.

A proximal portion 140 of first stent-graft 20, including proximal end 36, is positioned in the upper part of descending aorta 102, a middle portion 142 of first stent-graft 20 is positioned in aortic arch 100, and a distal portion 144 of first stent-graft 20, including distal end 38, is positioned in brachiocephalic artery 103. Proximal superior first lateral opening 34A faces toward and is aligned with left subclavian artery 105, and distal superior first lateral opening 34B faces toward and is aligned with left common carotid artery 104. Distal inferior first lateral opening 34C is disposed in aortic arch 100 facing upstream, generally toward ascending aorta 101, in a vicinity of the bifurcation of aortic arch 100 and brachiocephalic artery 103. For some applications, proper rotational alignment and/or axial orientation of the first lateral openings is achieved using fluoroscopy. For example, first stent-graft 20 may comprise one or more radiopaque markers in a vicinity (e.g., on a periphery of) the first lateral openings.

Deployment of the Second Stent-Graft

Also as shown in FIG. 6B, second stent-graft 22 is positioned in its radially-compressed state within an outer tube of a delivery tool (either the same outer tube 130 used to deploy the first stent-graft, or a second outer tube), typically near distal end 132 of the outer tube (e.g., such that at least one end of stent-graft 22 is within a distance of distal end 132, which distance equals the sum of 2 cm and an axial length of the first stent-graft). A guidewire (either the same guidewire 120 used to deploy the first stent-graft, or a second guidewire) is advanced up descending aorta 102, through a proximal portion of first stent-graft 20, out of distal inferior first lateral opening 34C, and into aortic arch 100 and/or the upper part of ascending aorta 101. Outer tube 130 is advanced over guidewire 120, until second stent-graft 22 is partially disposed in the upper part of ascending aorta 101 and partially disposed within radially-expanded first stent-graft 20 in aortic arch 100. The guidewire is withdrawn, leaving outer tube 130 in place.

Figure 6C:
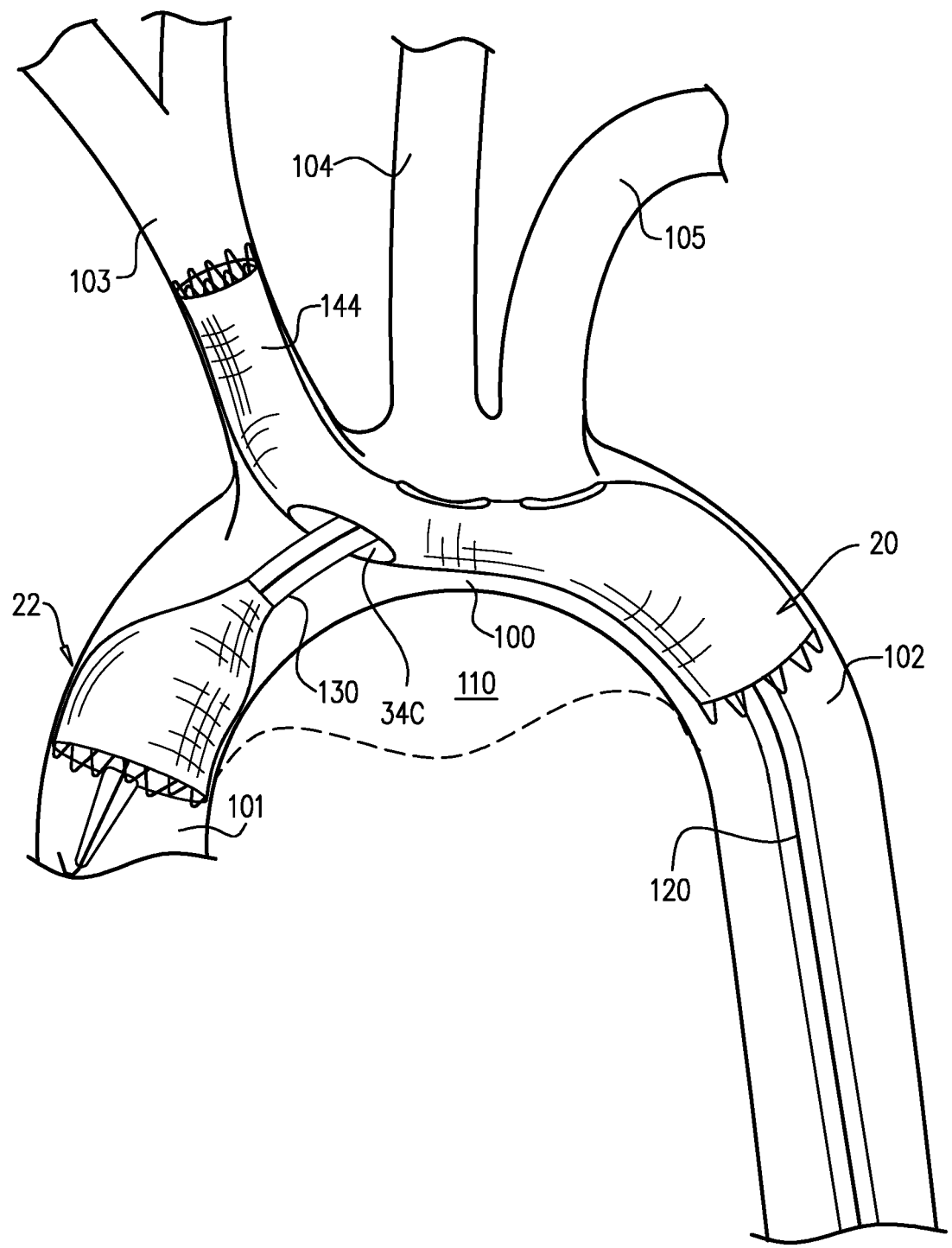
Figure 6D:
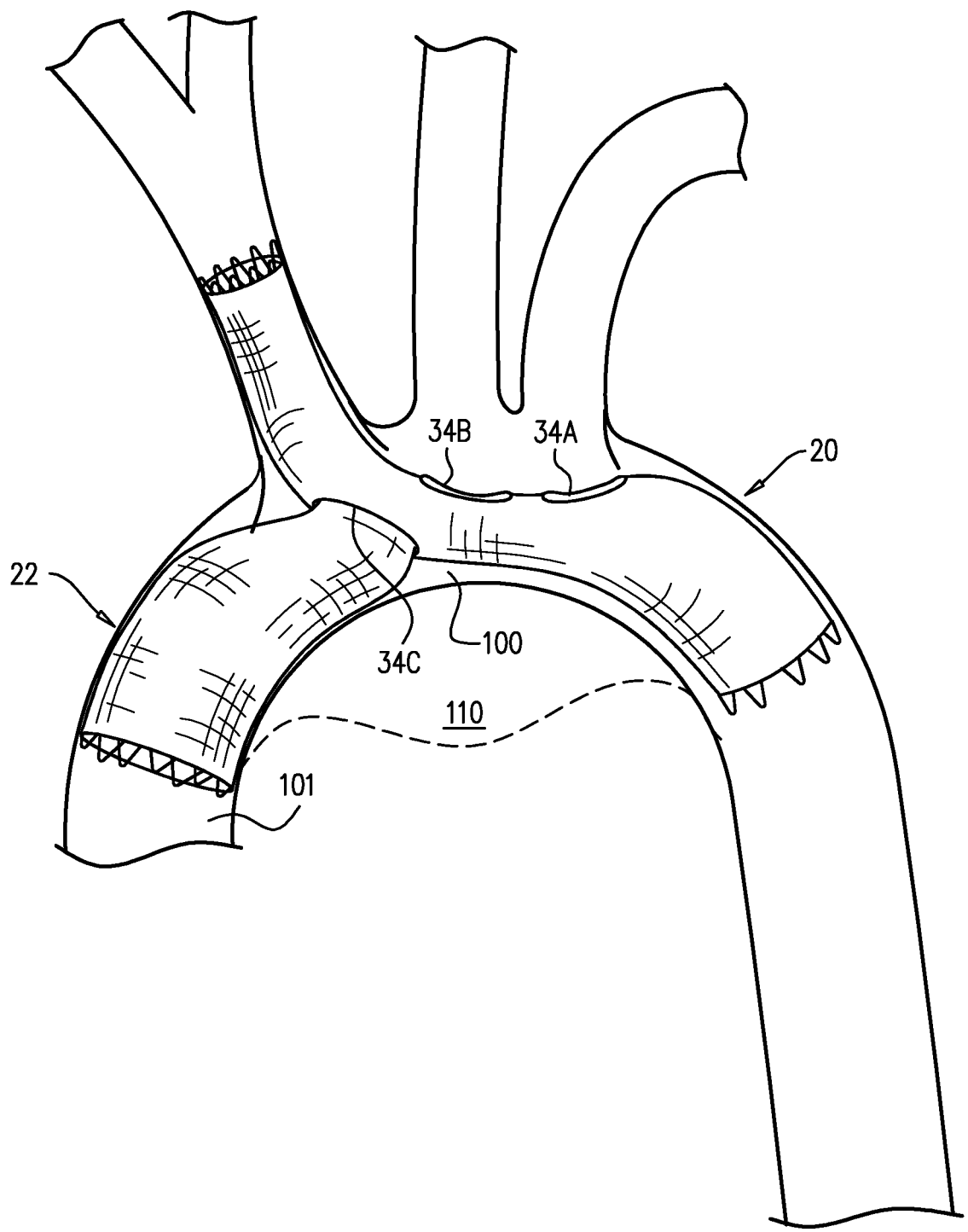

As shown in FIGS. 6C and 6D, the second stent-graft is held in place as outer tube 130 is withdrawn, thereby delivering the second stent-graft from the outer tube. Optionally, techniques for holding the second stent-graft in place may be used that are described hereinbelow with reference to FIGS. 10 and 11A-E or FIGS. 12A-C. Second stent-graft 22 typically self-expands, until it assumes its radially-expanded state, upon reaching its maximum unconstrained size, and/or being constrained from further expansion by the wall of the blood vessels. FIG. 6C shows the second stent-graft partially released from outer tube 130 (and thus partially expanded), and FIG. 6D shows the second stent-graft fully released from the outer tube (and thus fully expanded).

A proximal portion of second stent-graft 22, including proximal end 46, is positioned within first stent-graft 20 in aortic arch 100, and a distal portion of second stent-graft 22, including distal end 48, is positioned in the upper part of ascending aorta 101.

Second stent-graft 22 is thus adapted for transluminal delivery in its radially-compressed state through a portion of first stent-graft 20 and one of first lateral openings 34 (e.g., distal inferior first lateral opening 34C), while the first stent-graft is in its radially-expanded state.

Deployment of the Third Stent-Graft

Figure 6E:
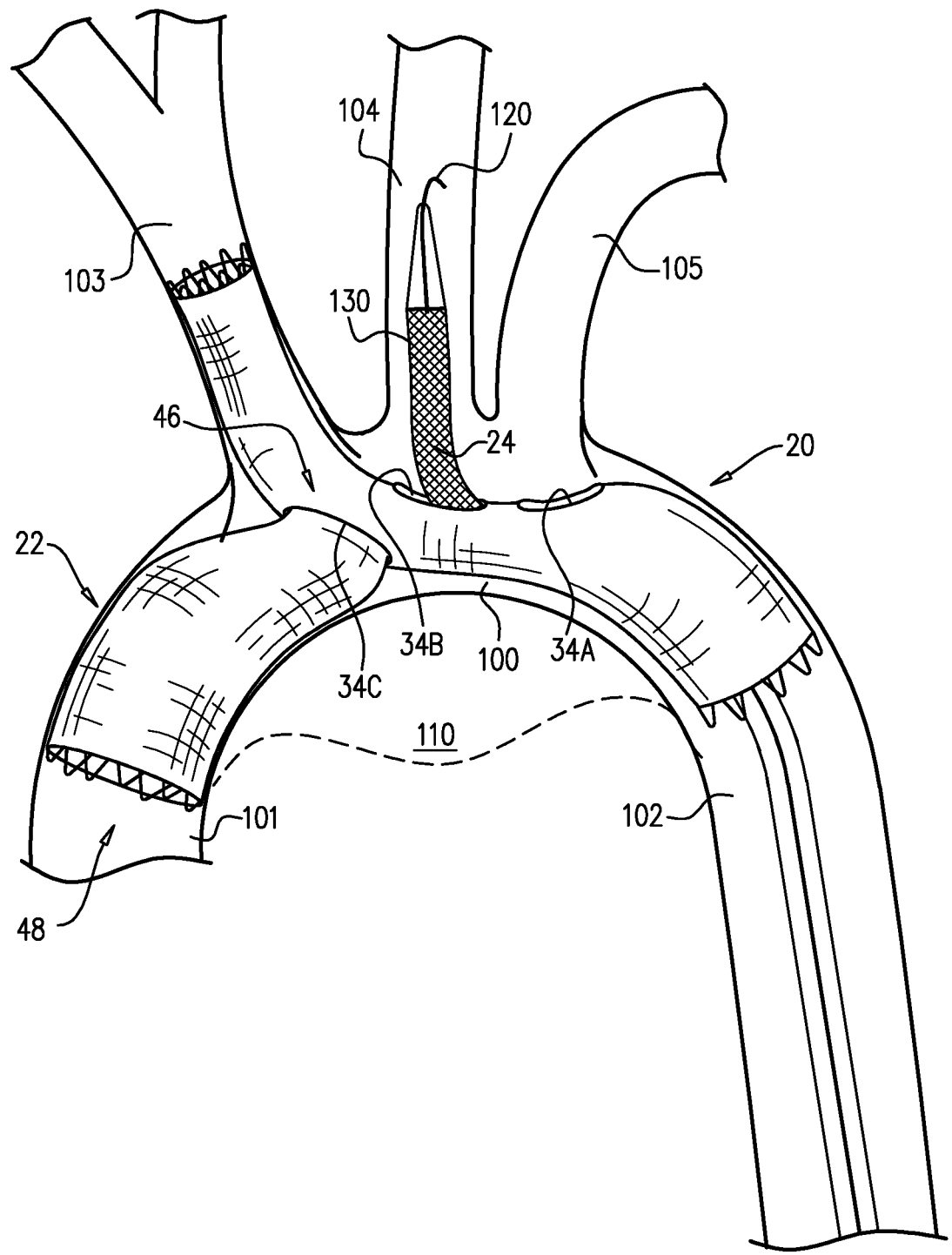

Third stent-graft 24 is positioned in its radially-compressed state within an outer tube of a delivery tool (either the same outer tube 130 used to deploy the first and/or second stent-grafts, or another outer tube), typically near distal end 132 of the outer tube (e.g., such that at least one end of stent-graft 24 is within a distance of distal end 132, which distance equals the sum of 2 cm and an axial length of the first stent-graft). A guidewire (either the same guidewire 120 used to deploy the first and/or second stent-grafts, or an additional guidewire) is advanced up descending aorta 102, through a proximal portion of first stent-graft 20, out of one of proximal superior first lateral opening 34A and distal superior first lateral opening 34B, and into a second one of the branches of aortic arch 100, such as left common carotid artery 104 or left subclavian artery 105. In the application shown in FIG. 6E, the guidewire is advanced out of distal superior first lateral opening 34B and into left common carotid artery 104. Alternatively, the guidewire is instead advanced out of proximal superior first lateral opening 34A and into left subclavian artery 105, in which case the fourth stent-graft, described below, is instead advanced out of distal superior first lateral opening 34B and into left common carotid artery 104. Outer tube 130 is advanced over guidewire 120, until third stent-graft 24 is partially disposed in the selected one of left common carotid artery 104 and left subclavian artery 105 (left common carotid artery 104 in FIG. 6E) and partially disposed within radially-expanded second stent-graft 22 in the aortic arch, as shown in FIG. 6E. The guidewire is withdrawn, leaving outer tube 130 in place.

Figure 6F:
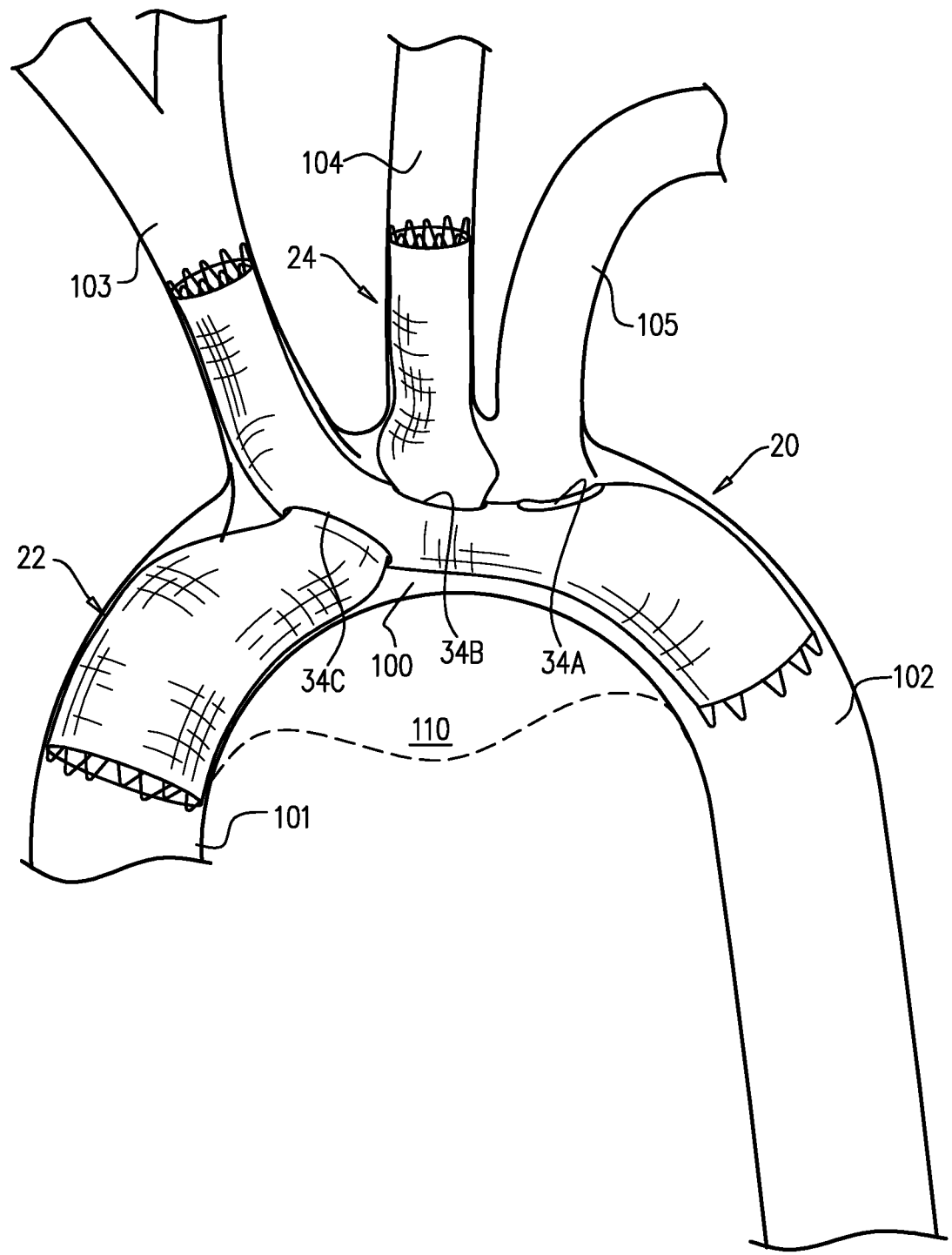

As shown in FIG. 6F, the third stent-graft is held in place as outer tube 130 is withdrawn, thereby delivering the third stent-graft from the outer tube. Optionally, techniques for holding the third stent-graft in place may be used that are described hereinbelow with reference to FIGS. 10 and 11A-E or FIGS. 12A-C. Third stent-graft 24 typically self-expands, until it assumes its radially-expanded state, upon reaching its maximum unconstrained size, and/or being constrained from further expansion by the wall of the blood vessels.

A proximal portion of third stent-graft 24, including proximal end 56, is positioned within first stent-graft 20 in aortic arch 100, and a distal portion of third stent-graft 24, including distal end 58, is positioned in left common carotid artery 104.

Third stent-graft 24 is thus adapted for transluminal delivery in its radially-compressed state through a portion of first stent-graft 20 and one of first lateral openings 34, such as one of proximal superior first lateral opening 34A and distal superior first lateral opening 34B, while the first stent-graft is in its radially-expanded state.

Deployment of the Fourth Stent-Graft

Figure 6G:
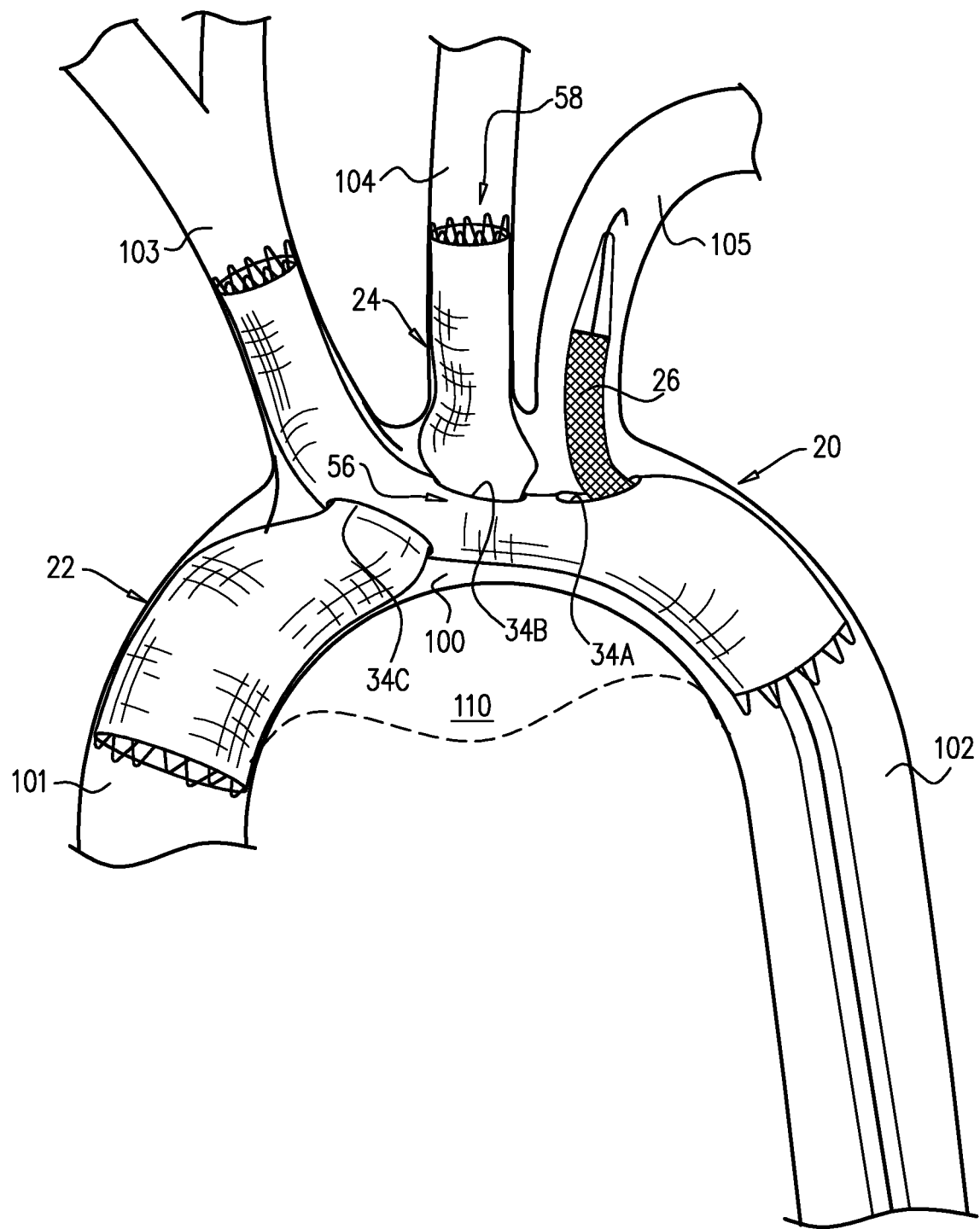

Fourth stent-graft 26 is positioned in its radially-compressed state within an outer tube of a delivery tool (either the same outer tube 130 used to deploy the first, second, and/or third stent-grafts, or an additional outer tube), typically near distal end 132 of the outer tube (e.g., such that at least one end of stent-graft 26 is within a distance of distal end 132, which distance equals the sum of 2 cm and an axial length of the first stent-graft). A guidewire (either the same guidewire 120 used to deploy the first, second, and/or third stent-grafts, or an additional guidewire) is advanced up descending aorta 102, through a proximal portion of first stent-graft 20, out of one of proximal superior first lateral opening 34A and distal superior first lateral opening 34B, and into a second one of the branches of aortic arch 100, such as left common carotid artery 104 or left subclavian artery 105. In the application shown in FIG. 6G, the guidewire is advanced out of proximal superior first lateral opening 34A and into left subclavian artery 105. Alternatively, the guidewire stent-graft is instead advanced out of distal superior first lateral opening 34B and into left common carotid artery 104, in which case the third stent-graft, described above, is instead advanced out of proximal superior first lateral opening 34A and into left subclavian artery 105. Outer tube 130 is advanced over guidewire 120, until fourth stent-graft 26 is partially disposed in the selected one of left common carotid artery 104 and left subclavian artery 105 (left subclavian artery 105 in FIG. 6G) and partially disposed within radially-expanded second stent-graft 22 in the aortic arch, as shown in FIG. 6G. The guidewire is withdrawn, leaving outer tube 130 in place.

Figure 6H:
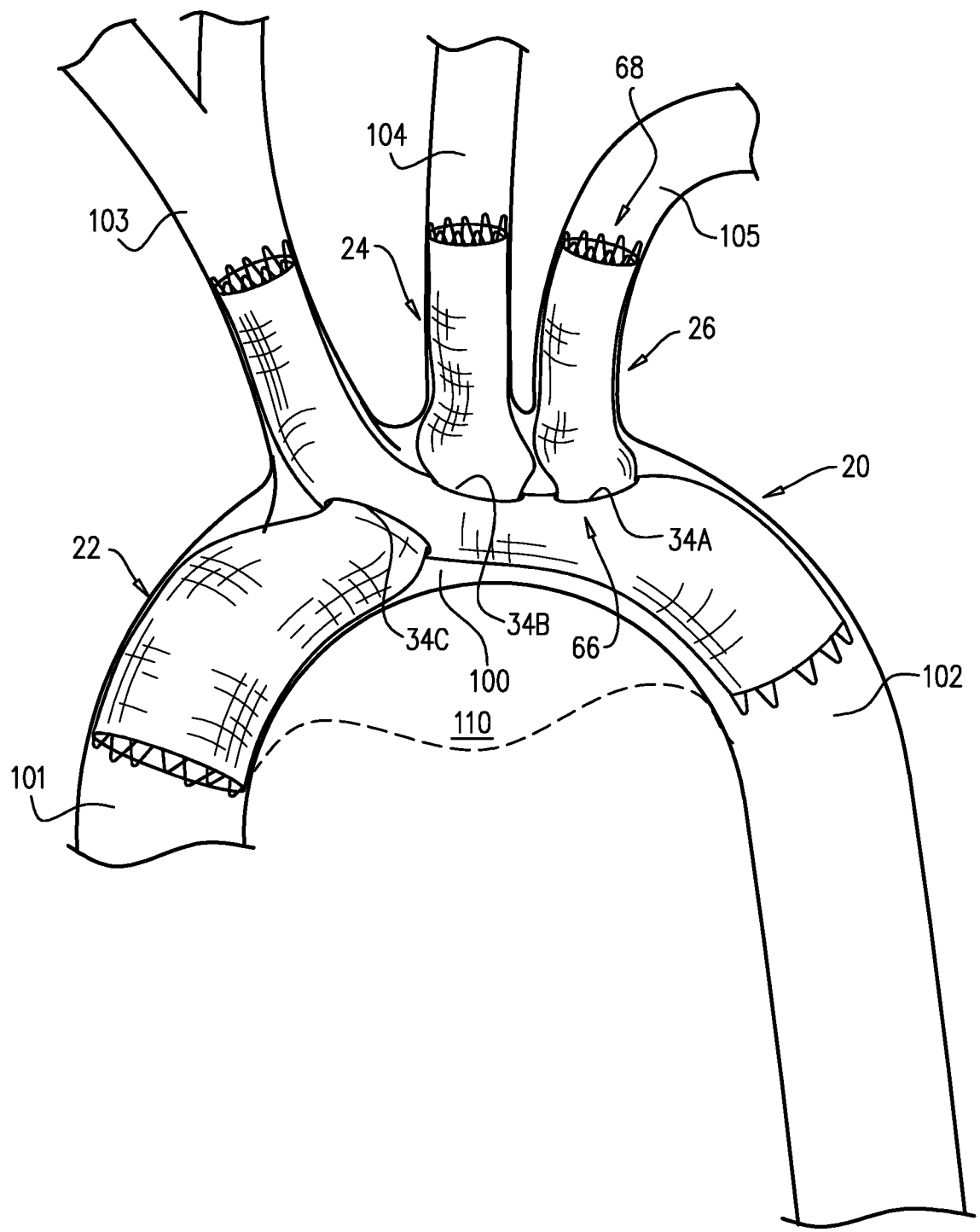

As shown in FIG. 6H, the fourth stent-graft is held in place as outer tube 130 is withdrawn, thereby delivering the fourth stent-graft from the outer tube. Optionally, techniques for holding the fourth stent-graft in place may be used that are described hereinbelow with reference to FIGS. 10 and 11A-E or FIGS. 12A-C. Fourth stent-graft 26 typically self-expands, until it assumes its radially-expanded state, upon reaching its maximum unconstrained size, and/or being constrained from further expansion by the wall of the blood vessels.

A proximal portion of fourth stent-graft 26, including proximal end 66, is positioned within first stent-graft 20 in aortic arch 100, and a distal portion of fourth stent-graft 26, including distal end 68, is positioned in left subclavian artery 105.

Fourth stent-graft 26 is thus adapted for transluminal delivery in its radially-compressed state through a portion of first stent-graft 20 and one of first lateral openings 34, such as one of proximal superior first lateral opening 34A and distal superior first lateral opening 34B, while the first stent-graft is in its radially-expanded state.

As can be seen in FIG. 6H, upon deployment of all four stent-grafts, multi-component stent-graft system 10 defines a blood-flow path from ascending aorta 101, over aortic arch 100, and to descending aorta 102. Multi-component stent-graft system 10 additionally provides blood-flow paths to the three branches of the aortic arch: brachiocephalic artery 103, left common carotid artery 104, and left subclavian artery 105.

First Stent-Graft Having Two Lateral Openings

Figure 7:
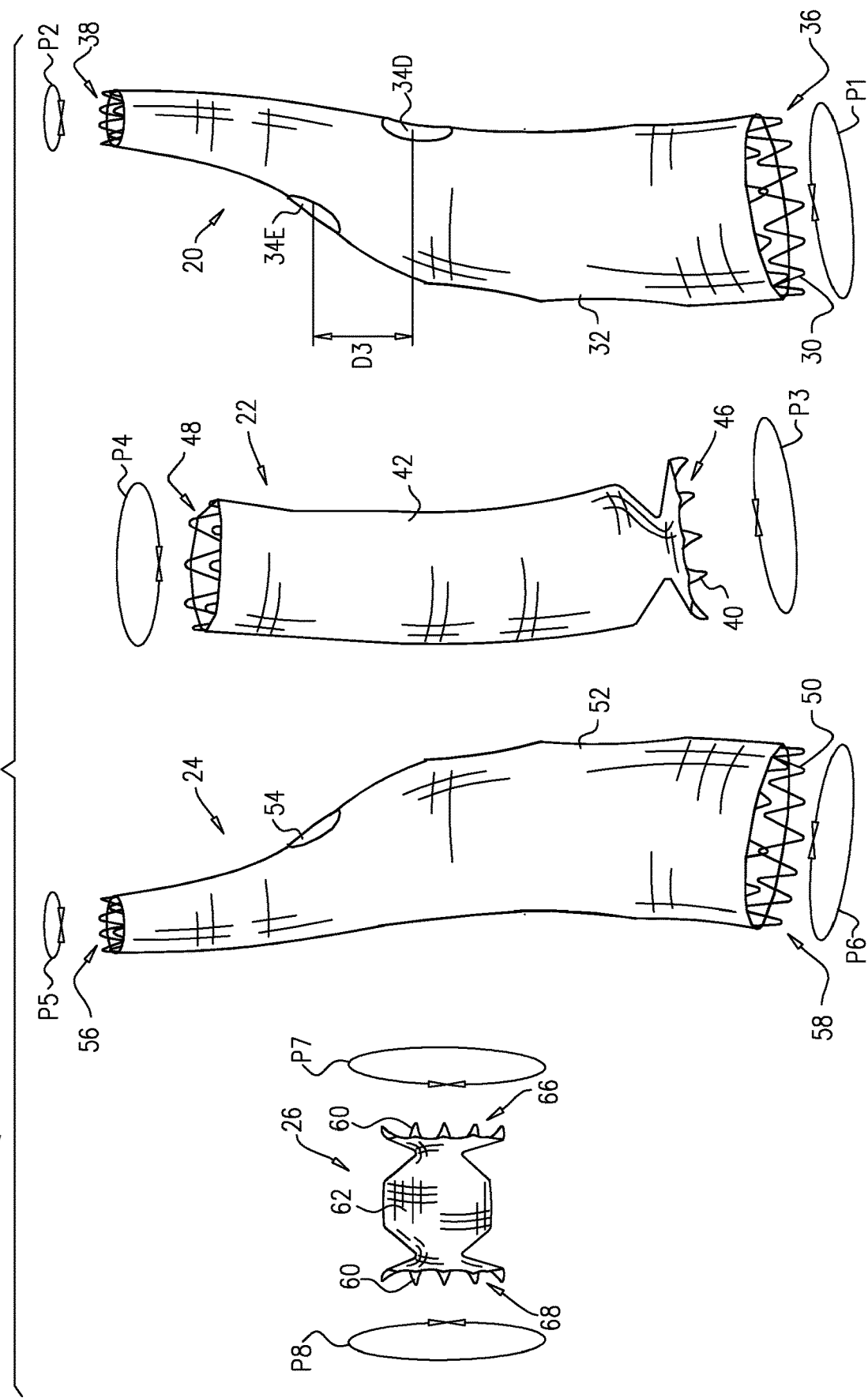
FIG. 7 is a schematic illustration of another configuration of the multi-component stent-graft system of FIGS. 1A-C and 2, in accordance with an application of the present invention.

Reference is now made to FIG. 7, which is a schematic illustration of another configuration of multi-component stent-graft system 10, in accordance with an application of the present invention. In this configuration, multi-component stent-graft system 10 comprises (a) first stent-graft 20, (b) second stent-graft 22, (c) third stent-graft 24, and (d) fourth stent-graft 26, typically configured as described hereinbelow. Except as described below, the stent-grafts are generally similar to the configurations of the stent-grafts described hereinabove with reference to FIGS. 1A-C and 2. The stent-grafts are configured to assume radially-compressed states, such as when initially positioned in one or more outer tubes of one or more delivery tools, as described hereinbelow with reference to FIGS. 9A, 9C, 9D, and 9F, and to assume radially-expanded states upon being deployed from the outer tube(s), as described hereinbelow with reference to FIGS. 9C, 9D, 9E, and 9G. FIG. 7 shows the stent-grafts in their radially-expanded states. For some applications, the stent-grafts are relaxed in their radially-expanded states. For some applications, the stent-grafts are configured to be self-expanding. For example, they may be heat-set to assume their radially-expanded states.

The First Stent-Graft

In the configuration shown in FIG. 7, first covering element 32 and first support element 30 are shaped so as to together define two first lateral openings 34 through first stent-graft 20 when the first stent-graft is in its radially-expanded state:

a superior first lateral opening 34D; and
an inferior first lateral opening 34E.

Typically, when first stent-graft 20 is unconstrained in its radially-expanded state, superior first lateral opening 34D is disposed on a first side of first stent-graft 20, and inferior first lateral opening 34E is disposed on a second side of the first stent-graft generally circumferentially opposite the first side. For example, if the stent-graft is viewed from one end, superior first lateral opening 34D may be disposed at between 11 o'clock and 1 o'clock (e.g., at 12 o'clock), and inferior first lateral opening 34E may disposed at between 5 o'clock and 7 o'clock (e.g., at 6 o'clock).

For some applications, stent-graft 20 narrows in a vicinity of superior first lateral opening 34D, with respect to a portion of stent-graft 20 proximal to the superior first lateral opening 34D (i.e., the perimeter is less at the lateral opening than in the more proximal portion). Such narrowing may increase the maneuverability of second stent-graft 22 when advancing the second stent-graft into left subclavian artery 105, by providing more space between the superior lateral opening and the bifurcation of the artery.

Typically, inferior first lateral opening 34E is not axially aligned with superior first lateral opening 34D. Typically, inferior first lateral opening 34E does not axially overlap with superior first lateral opening 34D.

For some applications, when first stent-graft 20 is unconstrained in its radially-expanded state, first perimeter P1 of first end 36 of the first stent-graft is greater than second perimeter P2 of second end 38 of the first stent-graft, and/or a first cross-sectional area of the first end 36 is greater than a second cross-sectional area of second end 38. For example, first perimeter P1 may equal at least 150% of second perimeter P2, such as at least 250%, or at least 400%, and/or the first cross-sectional area may equal at least 225% of the second cross-sectional area, such as at least 625%, or at least 1600%.

For example, first perimeter P1 may be at least 7.5 cm, no more than 15 cm, and/or between 7.5 and 15 cm, and second perimeter P2 may be at least 2.5 cm, no more than 5.7 cm, and/or between 2.5 and 5.7 cm.

For some applications, when first stent-graft 20 is unconstrained in its radially-expanded state, a perimeter of superior first lateral opening 34D is at least 2.5 cm, no more than 5 cm, and/or between 2.5 and 5 cm, and a perimeter of inferior first lateral opening 34E is at least 4.5 cm, no more than 12 cm, and/or between 4.5 and 12 cm.

For some applications, when first stent-graft 20 is unconstrained in its radially-expanded state, a perimeter of inferior first lateral opening 34E is at least 25%, e.g., at least 40%, or at least 60% of first perimeter P1, and/or at least 50%, e.g., at least 75%, or at least 100% of second perimeter P2. For some applications, first perimeter P1 does not equal second perimeter P2, and the perimeter of inferior first lateral opening 34E is at least 60% of the lesser of first and second perimeters P1 and P2.

For some applications, first stent-graft 20, when unconstrained in its radially-expanded state, has an axial length of at least 10 cm, no more than 40 cm, and/or between 10 and 40 cm. (The axial length is measured along a central longitudinal axis of the stent-graft, including in applications in which the stent-graft is curved.) For some applications, first stent-graft 20, when unconstrained in its radially-expanded state, has a greatest perimeter (at any axial location along the stent-graft) of at least 12 cm, no more than 21 cm, and/or between 12 and 21 cm.

For some applications, an axial distance D3 between the centers of superior first lateral opening 34D and inferior first lateral opening 34E is between 0 and 5 cm.

Figure 9A:
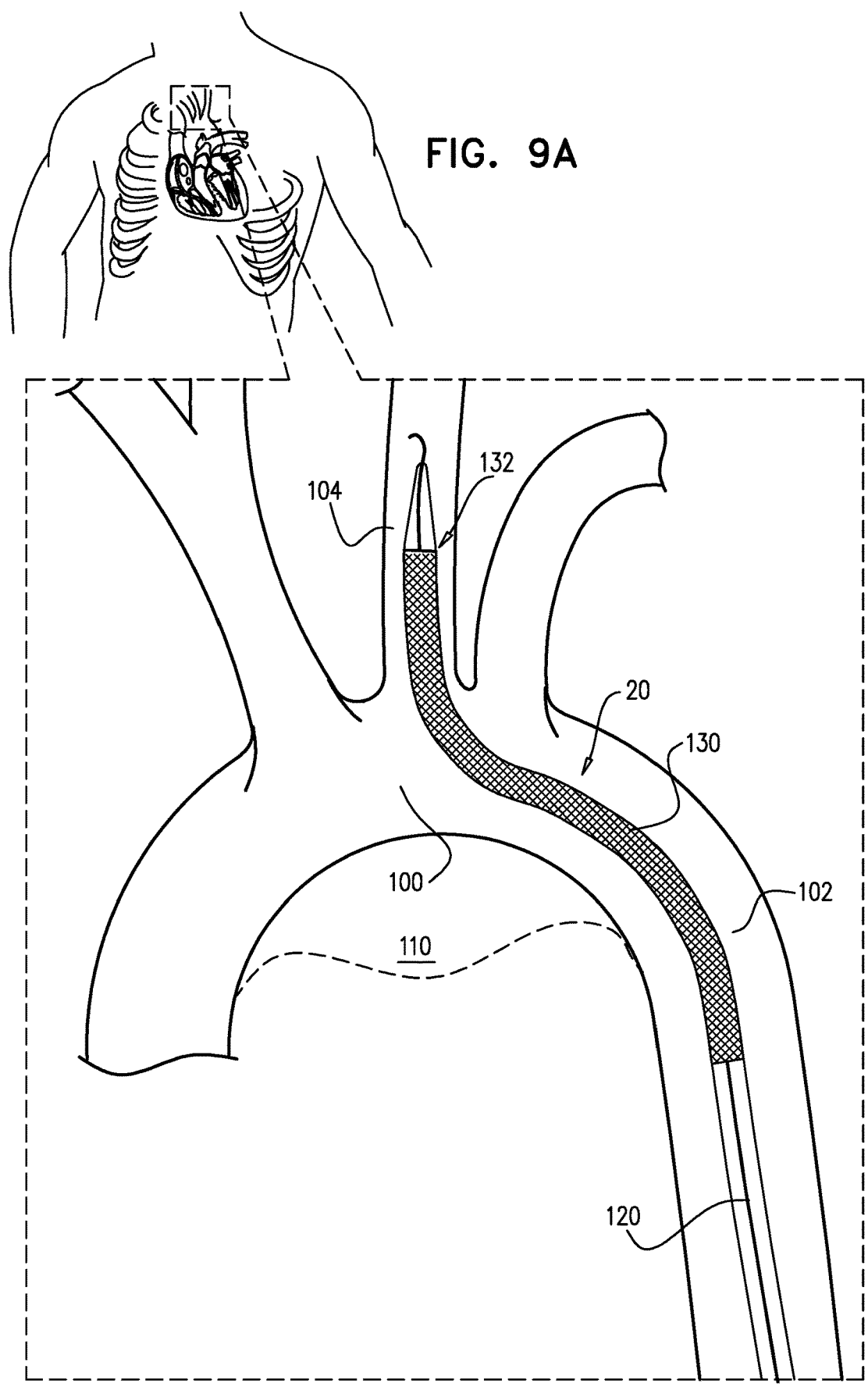
FIGS. 9A-G are schematic illustrations of an exemplary transluminal delivery procedure for implanting the multi-component stent-graft system of FIGS. 7 and 8, in accordance with an application of the present invention.
Figure 9B:
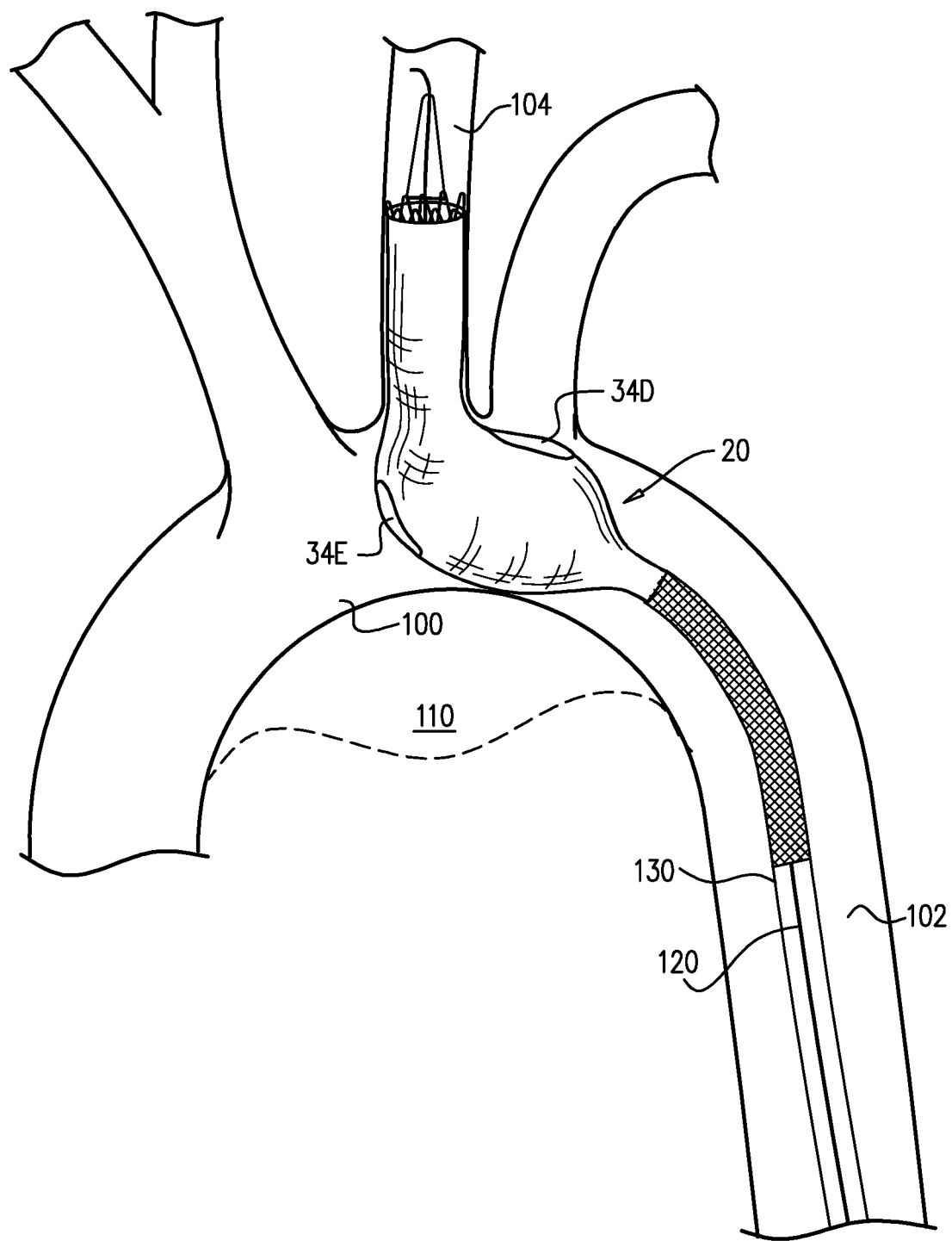
Figure 9C:
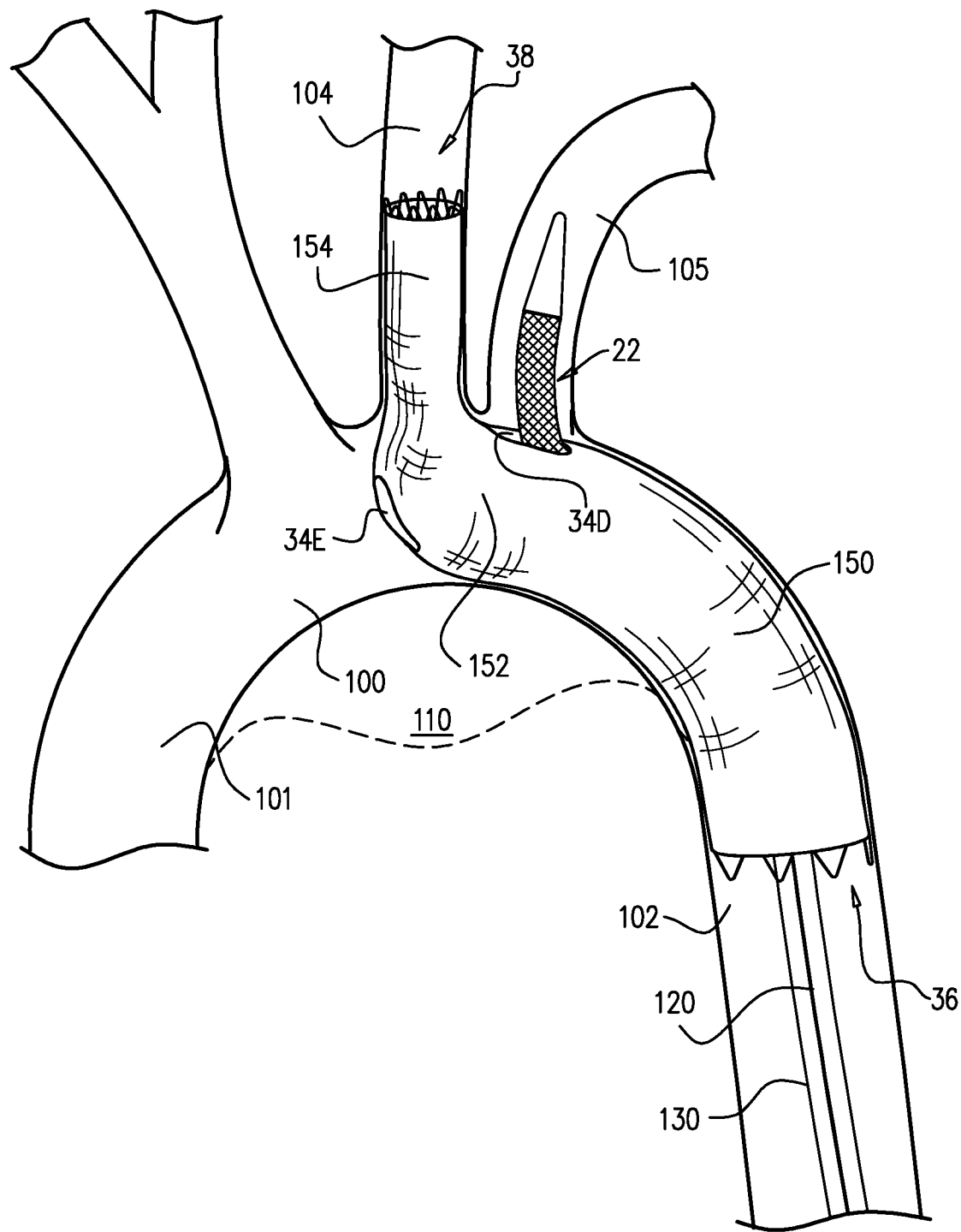

For some applications, such dimensions allow the first stent-graft to be positioned such that (a) a proximal, radially larger, portion of the stent-graft, including the proximal end thereof, is disposed in the aorta downstream from the bifurcation with the left subclavian artery, at least partially in the upper part of the descending aorta, and (b) a distal, radially smaller, portion of the stent-graft, including the distal end thereof, is disposed in the left common carotid artery, such as described hereinbelow with reference to FIG. 9C. For some applications, the proximal portion of the stent-graft has an average perimeter that is greater than (e.g., between 5% and 15% greater than) an average perimeter of the portion of the aorta in which it is disposed (excluding expansion of the aorta due to the aneurysm, i.e., assuming the aorta were healthy). For some applications, the distal portion of the stent-graft has an average perimeter that is greater than (e.g., between 5% and 15% greater than) the average perimeter of the portion of the left common carotid artery in which it is disposed.

The Second Stent-Graft

In the configuration shown in FIG. 7, second covering element 42 and second support element 40 of second stent-graft 22 are shaped so as to together define no lateral openings.

For some applications, as shown in FIG. 7, proximal end 46 of second stent-graft 22 is outwardly flared in a proximal direction when the stent-graft is unconstrained in its radially-expanded state. Optionally, the stent-graft is additionally slightly indented radially inward immediately distal to the outward flare. Typically, covering element 42 covers at least a distal portion of the outward flare. The flare enables secure anchoring of the second stent-graft to the first stent-graft, such as described hereinbelow with reference to FIG. 9D. Alternatively, proximal end 46 is not flared, and second stent-graft instead has the configuration FIG. 1A or FIG. 1B. In this alternate configuration, covering element 42 typically does not fully cover proximal sub-portion 70 (as shown in FIGS. 1A and 1B) of support element 40, thereby allowing blood flow through the stent-graft, as described hereinbelow with reference to FIG. 8. Optionally, proximal sub-portion 70 is flared radially outward in a proximal direction at its proximal end.

For some applications, when second stent-graft 22 is unconstrained in its radially-expanded state, fourth perimeter P4 of second (distal) end 48 of the second stent-graft is substantially greater than third perimeter P3 of first (proximal) end 46 of the second stent-graft, such as at least 150% of P3, e.g., at least 200% or at least 300%. For some applications, third perimeter P3 is at least 5.5 cm, no more than 17 cm, and/or between 5.5 and 17 cm. For some applications, fourth perimeter P4 is at least 2.75 cm, no more than 6.3 cm, and/or between 2.75 and 6.3 cm.

For some applications, second stent-graft 22, when unconstrained in its radially-expanded state, has an axial length of at least 5 cm, no more than 20 cm, and/or between 5 and 20 cm. (The axial length is measured along a central longitudinal axis of the stent-graft, including in applications in which the stent-graft is curved.) For some applications, second stent-graft 22, when unconstrained in its radially-expanded state, has a greatest perimeter (at any axial location along the stent-graft) of at least 3 cm, no more than 6 cm, and/or between 3 and 6 cm.

For some applications, such dimensions allow the second stent-graft to be positioned such that (a) a proximal portion of the stent-graft, including the proximal end thereof, is disposed in the aorta in the first stent-graft, and (b) a distal portion of the stent-graft, including the distal end thereof, is disposed in the left common carotid artery, such as described hereinbelow with reference to FIG. 9D. For some applications, the proximal portion of the stent-graft has an average perimeter that is less than (e.g., between 30% and 70% less than) an average perimeter of the portion of the aortic arch in which it is disposed (excluding expansion of the aortic arch due to the aneurysm, i.e., assuming the aortic arch were healthy). For some applications, the distal portion of the stent-graft has an average perimeter that is greater than (e.g., between 5% and 15% greater than) the average perimeter of the portion of the left common carotid artery in which it is disposed.

The Third Stent-Graft

In the configuration shown in FIG. 7, third covering element 52 and third support element 50 of third stent-graft 24 are shaped so as to together define third lateral opening 54 (typically, exactly one third lateral opening) through third stent-graft 24 when the third stent-graft is in its radially-expanded state.

For some applications, when third stent-graft 24 is unconstrained in its radially-expanded state, sixth perimeter P6 of second (distal) end 58 of the third stent-graft is substantially greater than fifth perimeter P5 of first (proximal) end 56 of the third stent-graft, such as at least 150% of P3, e.g., at least 250% or 400%. For some applications, fifth perimeter P5 is at least 2.5 cm, no more than 6.3 cm, and/or between 2.5 and 6.3 cm. For some applications, sixth perimeter P6 is at least 9.4 cm, no more than 18.8 cm, and/or between 9.4 and 18.8 cm.

For some applications, when third stent-graft 24 is unconstrained in its radially-expanded state, a perimeter of third lateral opening 54 is at least 4.7 cm, no more than 14 cm, and/or between 4.7 and 14 cm, such as at least 6.3 cm, no more than 11 cm, and/or between 6.3 and 11 cm.

For some applications, when third stent-graft 24 is unconstrained in its radially-expanded state, a perimeter of third lateral opening 54 is at least 25%, e.g., at least 40%, or at least 60% of sixth perimeter P6, and/or at least 50%, e.g., at least 100%, or at least 150% of fifth perimeter P5.

For some applications, third stent-graft 24, when unconstrained in its radially-expanded state, has an axial length of at least 8 cm, no more than 30 cm, and/or between 8 and 30 cm. (The axial length is measured along a central longitudinal axis of the stent-graft, including in applications in which the stent-graft is curved.) For some applications, third stent-graft 24, when unconstrained in its radially-expanded state, has a greatest perimeter (at any axial location along the stent-graft) of at least 12.5 cm, no more than 22 cm, and/or between 12.5 and 22 cm.

Figure 9D:
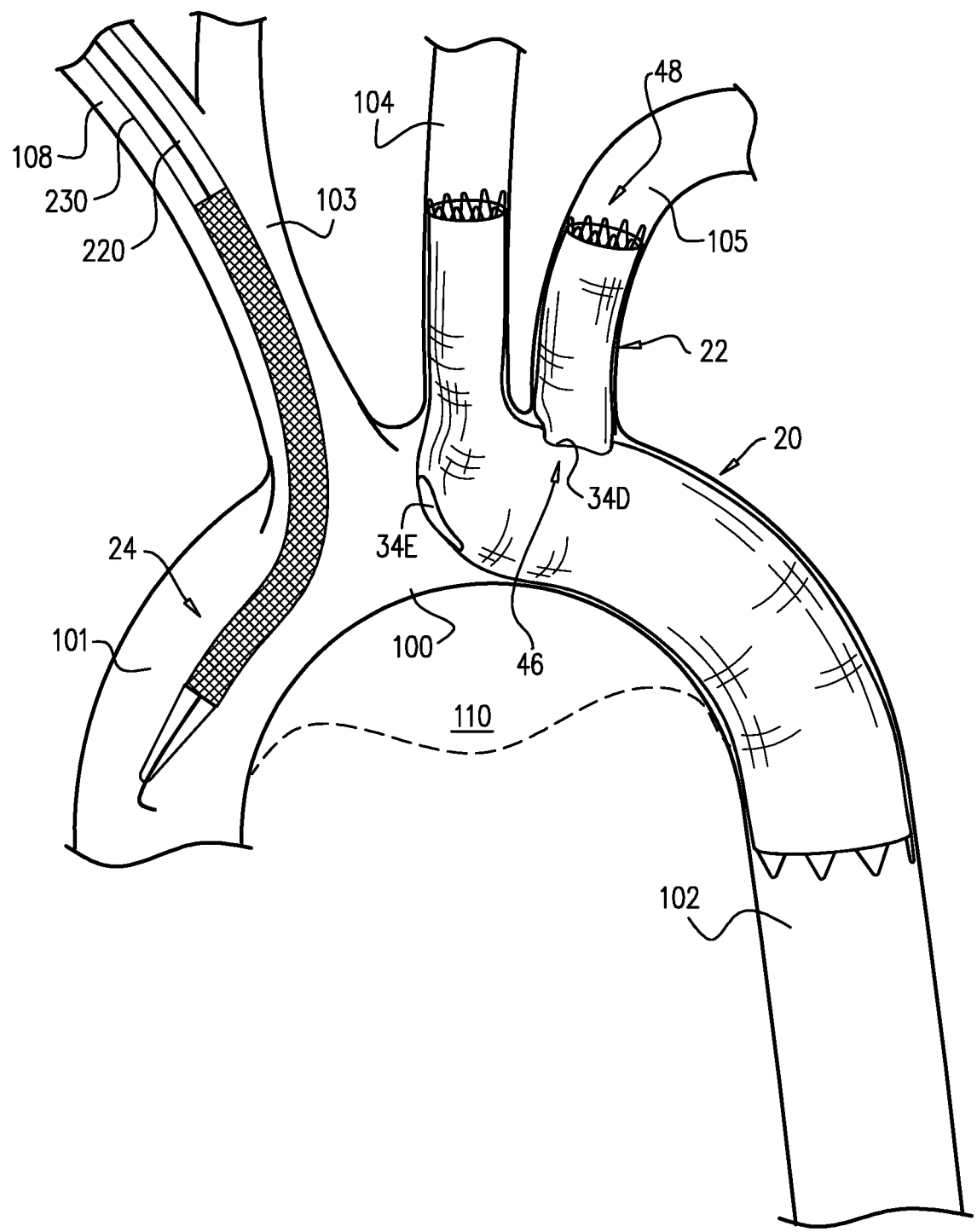
Figure 9E:
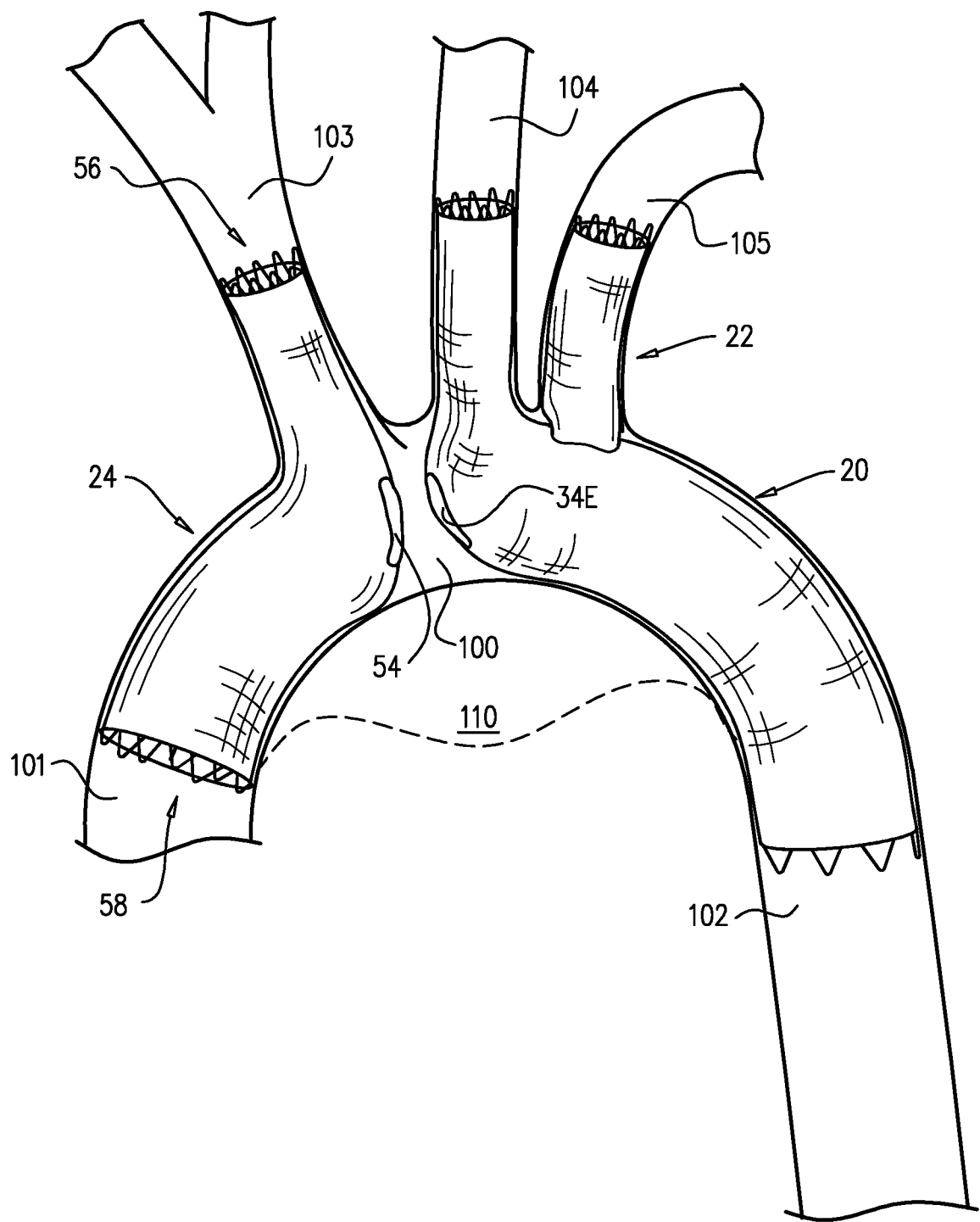

For some applications, such dimensions allow the third stent-graft to be positioned such that (a) a proximal, radially smaller, portion of the stent-graft, including the proximal end thereof, is disposed in the brachiocephalic artery, and (b) a distal, radially larger, portion of the stent-graft, including the distal end thereof, is disposed in the aorta upstream from the bifurcation with the brachiocephalic artery, at least partially in the upper part of the ascending aorta, such as described hereinbelow with reference to FIG. 9E. For some applications, the proximal portion of the stent-graft has an average perimeter that is greater than (e.g., between 5% and 15% greater than) an average perimeter of the portion of the brachiocephalic artery in which it is disposed. For some applications, the distal portion of the stent-graft has an average perimeter that is greater than (e.g., between 5% and 15% greater than) the average perimeter of the portion of the aorta in which it is disposed (excluding expansion of the aorta due to the aneurysm, i.e., assuming the aorta were healthy).

The Fourth Stent-Graft

In the configuration shown in FIG. 7, fourth covering element 62 and fourth support element 60 of fourth stent-graft 26 are shaped so as to together define no lateral openings.

Typically, proximal end 66 of fourth stent-graft 26 is outwardly flared in a proximal direction, and distal end 68 is outwardly flared in a distal direction, when the stent-graft is unconstrained in its radially-expanded state. Optionally, the stent-graft is additionally slightly indented radially inward immediately distal to the proximal outward flare, and immediately proximal to the distal outward flare. Typically, covering element 62 covers at least a distal portion of the proximal outward flare, and at least a proximal portion of the distal outward flare. The flares enable secure anchoring of the fourth stent-graft to the first and third stent-grafts, such as described hereinbelow with reference to FIG. 9G.

For some applications, when fourth stent-graft 26 is unconstrained in its radially-expanded state, seventh perimeter P7 of first (proximal) end 66 of the fourth stent-graft is approximately equal to eighth perimeter P8 of second (distal) end 68 of the fourth stent-graft, such as within 20% of P6. For some applications, each of seventh perimeter P7 and eighth perimeter P8 is at least 6.3 cm, no more than 12.6 cm, and/or between 6.3 and 12.6 cm.

For some applications, when fourth stent-graft 26 is unconstrained in its radially-expanded states, an axial length of fourth stent-graft 26 is at least 3 cm, no more than 10 cm, and/or between 3 and 10 cm. For some applications, when fourth stent-graft 26 is unconstrained in its radially-expanded state, a greatest perimeter of the fourth stent-graft (at any axial location along the stent-graft) is at least 3 cm, no more than 9 cm, and/or between 3 and 9 cm.

For some applications, such dimensions allow the fourth stent-graft to be positioned such that (a) a proximal portion of the stent-graft, including the proximal end thereof, is disposed in the aortic arch in the first stent-graft, and (b) a distal portion of the stent-graft, including the distal end thereof, is disposed in the aortic arch in the third stent-graft, such as described hereinbelow with reference to FIG. 9G. For some applications, each of the proximal and distal portions of the stent-graft has an average perimeter that is less than (e.g., between 30% and 70% less than) an average perimeter of the portion of the aortic in which they are disposed.

Additional Configuration Detail

For some applications, stent-grafts 20, 22, and 24 are configured (e.g., heat-set) to have generally straight longitudinal axes when unconstrained in their radially-expanded states, i.e., no forces are applied to the stent-grafts by a delivery tool, walls of a blood vessel, or otherwise. The stent-grafts typically assumed curved shapes when placed in respective blood vessels because of the force applied to the stent-grafts by the walls of the blood vessels, such as shown in FIGS. 9C-G.

For other applications, stent-grafts 20, 22, and 24 are configured (e.g., heat-set) to have generally curved longitudinal axes when unconstrained in their radially-expanded states, i.e., no forces are applied to the stent-grafts by a delivery tool, walls of a blood vessel, or otherwise. This curvature may help properly position the stent-grafts with respect to one another, such as shown in FIGS. 7 and 9C-G. This configuration is similar to the curved configuration shown in FIG. 1B. For some applications, at least one the stent-grafts is generally straight, while at least another one of the stent-grafts is generally curved.

Typically, first and second stent-grafts 20 and 22 are not fixed to one other when they are in their radially-compressed states. Likewise, first, second, and third stent-grafts 20, 22, and 24 are typically not fixed to one other when they are in their radially-compressed states. Furthermore, first, second, third, and fourth stent-grafts 20, 22, 24, and 26 are typically not fixed to one other when they are in their radially-compressed states. In other words, the stent-grafts are initially provided as separate, non-connected components, as shown in FIG. 4 (although they are typically initially positioned in outer tube(s) of delivery tool(s), as described hereinbelow), which are typically assembled in situ. Typically, first and second covering element 32 and 42 are not fixed to one other when they are in their radially-compressed states. Likewise, first, second, and third covering element 32, 42, and 52 are typically not fixed to one other when first, second, and third stent-grafts 20, 22, and 24 are in their radially-compressed states. Furthermore, first, second, third, and fourth covering elements 32, 42, 52, and 62 are typically not fixed to one other when first, second, third, and fourth stent-grafts 20, 22, 24, and 26 are in their radially-compressed states.

For some applications, one or more (e.g., all) of the lateral openings are circumscribed by respective generally annular structural stent elements of the support elements.

Assembly of the Stent-Grafts

Figure 8:
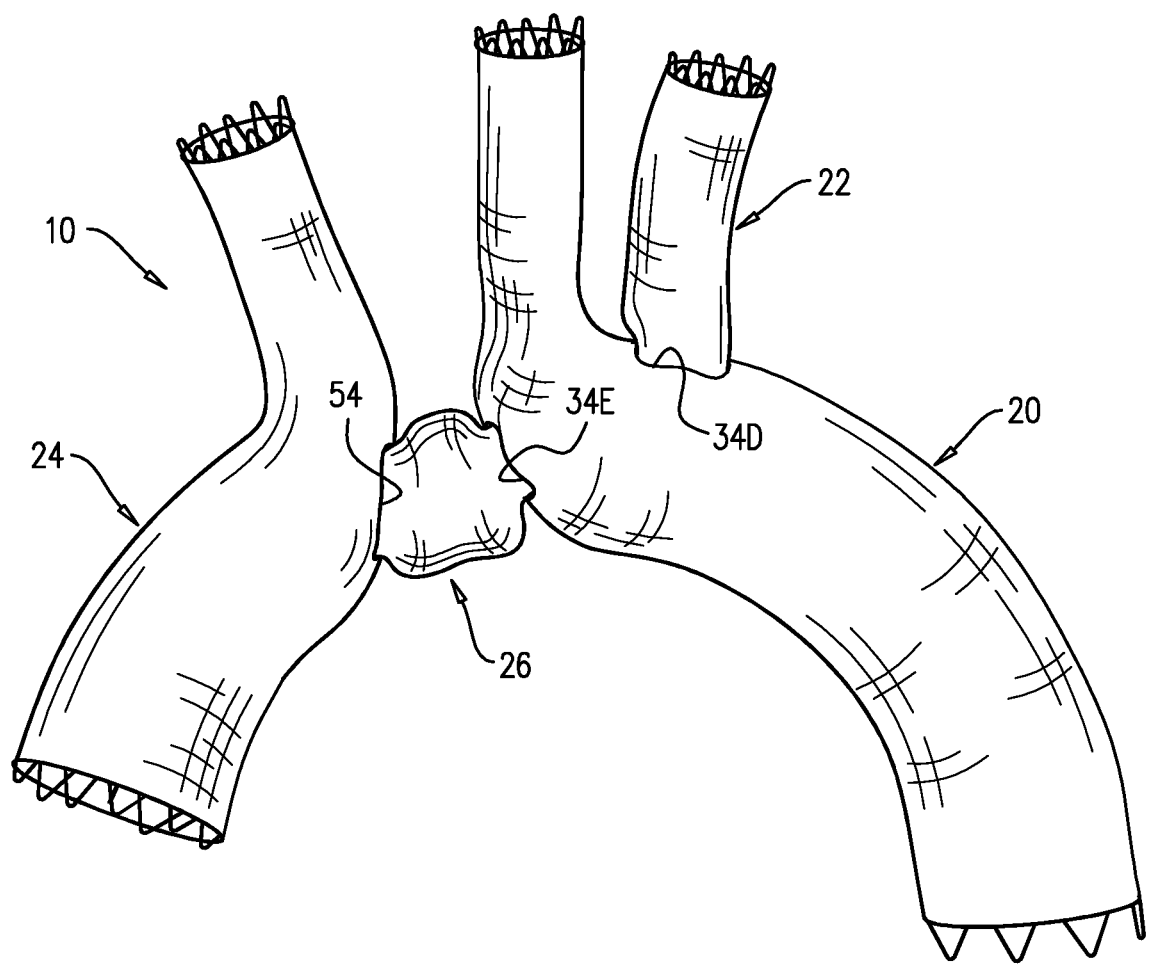
FIG. 8 is a schematic illustration of multi-component stent-graft system of FIG. 7 in an assembled state, in accordance with an application of the present invention.

FIG. 8 is a schematic illustration of multi-component stent-graft system 10, having the configuration described with reference to FIG. 7, in an assembled state, in accordance with an application of the present invention. As mentioned above, such assembly is typically performed in situ during an implantation procedure, but such assembly may also be performed ex vivo. First, second, third, and fourth stent-grafts 20, 22, 24, and 26 are shown in FIG. 8 in their radially-expanded states.

Second stent-graft 22 is configured to be disposed through superior first lateral opening 34D, such that a portion (e.g., the flared portion) of the second stent-graft is disposed within first stent-graft 20, and a portion of the second stent-graft is disposed outside of the first stent-graft. The first and second stent-grafts are configured such that second covering element 42 forms a blood-impervious seal with first covering element 32 around superior first lateral opening 34D, when the second stent-graft is thus disposed through the superior first lateral opening, and first and second stent-grafts 20 and 22 are in their radially-expanded states. The first and second stent-grafts are securely anchored to each other. The blood-impervious seal is typically formed because support element 30 of the first stent-graft is configured to having a resting perimeter that is greater than the perimeter of the superior first lateral opening, such that the distal inferior first lateral opening squeezes the second stent-graft when the second stent-graft expands.

Alternatively, for some applications in which second stent-graft is not flared, when second stent-graft 22 is disposed through first superior first lateral opening 34D and first and second stent-grafts 20 and 22 are in their radially-expanded states, a proximal portion of second support element 40 is disposed within first stent-graft 20, and second covering element 42 does not fully cover this proximal portion, thereby allowing blood flow through the first stent-graft (i.e., the second covering element does not fully cover proximal sub-portion 70), such as shown in FIG. 2. (Optionally, proximal sub-portion 70 is flared radially outward in a proximal direction at its proximal end.) Typically, at least a distal-most portion of this proximal portion is covered by second covering element 42, in order to form the above-mentioned blood-impervious seal with first covering element 32. Thus, second covering element 42 may be configured to cover a distal sub-portion, and not a proximal sub-portion, of this proximal portion. For some of these applications, second support element 40 is configured to extend into first stent-graft 20 a distance sufficient to help anchor the second stent-graft to the first stent-graft, such as at least 3 cm, no more than 10 cm, and/or between 3 and 10 cm. For some applications, the proximal portion has a perimeter that is sufficient to apply a radially-outward force against an inner surface of a wall of first stent-graft 20, in order to help anchor the second stent-graft to the first stent-graft. For example, an axial portion of the proximal portion having a length of at least 5 cm may have a perimeter that is at least 10% greater than a perimeter of a portion of the first stent-graft in which the proximal portion is disposed. Typically, second stent-graft 22 is deployed such that proximal portion 82 extends into the first stent-graft in a proximal direction from first lateral opening 34, such as shown in FIG. 2.

Proximal and distal ends 66 and 68 fourth stent-graft 26 are configured to be disposed through inferior first lateral opening 34E of first stent-graft 20 and third lateral opening 54 of third stent-graft 24, respectively, such that:
  a proximal portion (e.g., the proximal flared portion) of the fourth stent-graft is disposed within first stent-graft 20,
  a distal portion (e.g., the distal flared portion) of the fourth stent-graft is disposed within third stent-graft 24, and
  a middle portion of the fourth stent-graft is disposed outside of the first and third stent-grafts.

The first and fourth stent-grafts are configured such that fourth covering element 62 forms a blood-impervious seal with first covering element 32 around inferior first lateral opening 34E, when the proximal end of fourth stent-graft is thus disposed through the inferior first lateral opening 34E, and first and fourth stent-grafts 20 and 26 are in their radially-expanded states. The first and fourth stent-grafts are securely anchored to each other. Similarly, the third and fourth stent-grafts are configured such that fourth covering element 62 forms a blood-impervious seal with third covering element 52 around third lateral opening 54, when distal end of the fourth stent-graft is thus disposed through the third lateral opening, and third and fourth stent-grafts 24 and 26 are in their radially-expanded states. The third and fourth stent-grafts are securely anchored to each other.

For some applications, a method is provided that comprises assembling first, second, third, and fourth stent-grafts 20, 22, 24, and 26, as described hereinabove with reference to FIG. 8, either in situ or ex vivo.

An Exemplary Deployment Procedure for the Configuration in which the First Stent-Graft has Two Lateral Openings Reference is made to FIGS. 9A-G, which are schematic illustrations of an exemplary transluminal delivery procedure for implanting multi-component stent-graft system 10, as configured in FIGS. 7 and 8, in accordance with an application of the present invention. In this exemplary procedure, first, second, and fourth stent-grafts 20, 22, and 26 of system 10 are transvascularly (typically percutaneously) introduced into aortic arch 100, typically via one of the iliac arteries, while the stent-grafts are positioned in one or more outer tubes of a delivery tool in their radially-compressed states. Third stent-graft 24 is typically deployed via a right subclavian artery.

Deployment of the First Stent-Graft

First stent-graft 20 is initially positioned in its radially-compressed state within outer tube 130 of a delivery tool, typically near distal end 132 of the outer tube (e.g., such that at least one end of stent-graft 20 is within a distance of distal end 132, which distance equals the sum of 2 cm and an axial length of the first stent-graft). The exemplary procedure begins with the advancing of guidewire 120 up descending aorta 102 and into a first one of the branches of the aortic arch, such as left common carotid artery 104. Outer tube 130 is advanced over guidewire 120, until first stent-graft 20 is partially disposed in left common carotid artery 104, partially disposed in aortic arch 100, and partially disposed an upper part of descending aorta 102, as shown in FIG. 9A. The guidewire is withdrawn, leaving outer tube 130 in place.

As shown in FIGS. 9B and 9C, the first stent-graft is held in place as outer tube 130 is withdrawn, thereby delivering the first stent-graft from the outer tube. Optionally, techniques for holding the first stent-graft in place may be used that are described hereinbelow with reference to FIGS. 10 and 11A-E or FIGS. 12A-C. First stent-graft 20 typically self-expands, until it assumes its radially-expanded state, upon reaching its maximum unconstrained size, and/or being constrained from further expansion by the wall of the blood vessels. Alternatively, the first stent-graft (and/or the second, third, and/or fourth stent-grafts, as described hereinbelow) is delivered using an over-the-wire (OTW) approach, in which the guidewire is left in place until the stent-graft is expanded, and thereafter the guidewire is withdrawn. FIG. 9B shows the first stent-graft partially released from outer tube 130 (and thus partially expanded), and FIG. 9C shows the first stent-graft fully released from the outer tube (and thus fully expanded).

A proximal portion 150 of first stent-graft 20, including proximal end 36, is positioned in the upper part of descending aorta 102, a middle portion 152 of first stent-graft 20 is positioned in aortic arch 100, and a distal portion 154 of first stent-graft 20, including distal end 38, is positioned in left common carotid artery 104. Superior first lateral opening 34D faces toward and is aligned with left subclavian artery 105, and inferior first lateral opening 34E is disposed in aortic arch 100 facing upstream, generally toward ascending aorta 101, in a vicinity of the bifurcation of aortic arch 100 and left common carotid artery 104. For some applications, proper rotational alignment and/or axial orientation of the first lateral openings is achieved using fluoroscopy. For example, first stent-graft 20 may comprise one or more radiopaque markers in a vicinity (e.g., on a periphery of) the first lateral openings.

Deployment of the Second Stent-Graft

Also as shown in FIG. 9C, second stent-graft 22 is initially positioned in its radially-compressed state within an outer tube of a delivery tool (either the same outer tube 130 used to deploy the first stent-graft, or a second outer tube), typically near distal end 132 of the outer tube (e.g., such that at least one end of stent-graft 22 is within a distance of distal end 132, which distance equals the sum of 2 cm and an axial length of the first stent-graft). A guidewire (either the same guidewire 120 used to deploy the first stent-graft, or a second guidewire) is advanced up descending aorta 102, through a proximal portion of first stent-graft 20, out of superior first lateral opening 34D, and into left subclavian artery 105. Outer tube 130 is advanced over guidewire 120, until second stent-graft 22 is partially disposed in left subclavian artery 105 and partially disposed within radially-expanded first stent-graft 20 in aortic arch 100. The guidewire is withdrawn, leaving outer tube 130 in place.

As shown in FIG. 9D, the second stent-graft is held in place as outer tube 130 is withdrawn, thereby delivering the second stent-graft from the outer tube. Optionally, techniques for holding the second stent-graft in place may be used that are described hereinbelow with reference to FIGS. 10 and 11A-E or FIGS. 12A-C. Second stent-graft 22 typically self-expands, until it assumes its radially-expanded state, upon reaching its maximum unconstrained size, and/or being constrained from further expansion by the wall of the blood vessels.

A proximal portion of second stent-graft 22, including proximal end 46, is positioned within first stent-graft 20 in aortic arch 100, and a distal portion of second stent-graft 22, including distal end 48, is positioned in left subclavian artery 105.

Second stent-graft 22 is thus adapted for transluminal delivery in its radially-compressed state through a portion of first stent-graft 20 and one of first lateral openings 34 (e.g., superior first lateral opening 34D), while the first stent-graft is in its radially-expanded state.

Deployment of the Third Stent-Graft

As also shown in FIG. 9D, third stent-graft 24 is initially positioned in its radially-compressed state within an outer tube 230 of a delivery tool (typically separate from outer tube 130 used to deploy the first and/or second stent-grafts), typically near a distal end 232 of the outer tube (e.g., such that at least one end of stent-graft 24 is within a distance of distal end 232, which distance equals the sum of 2 cm and an axial length of the third stent-graft). A guidewire 220 (typically separate from guidewire 120 used to deploy the first and/or second stent-grafts) is advanced down a right subclavian artery 108 and brachiocephalic artery 103 into the upper part of ascending aorta 101. Outer tube 230 is advanced over guidewire 220, until third stent-graft 24 is partially disposed in brachiocephalic artery 103 and partially disposed in the upper part of ascending aorta 101. The guidewire is withdrawn, leaving outer tube 130 in place.

As shown in FIG. 9E, the third stent-graft is held in place as outer tube 230 is withdrawn, thereby delivering the third stent-graft from the outer tube. Optionally, techniques for holding the third stent-graft in place may be used that are described hereinbelow with reference to FIGS. 10 and 11A-E or FIGS. 12A-C. Third stent-graft 24 typically self-expands, until it assumes its radially-expanded state, upon reaching its maximum unconstrained size, and/or being constrained from further expansion by the wall of the blood vessels.

A proximal portion of third stent-graft 24, including proximal end 56, is positioned within brachiocephalic artery 103, and a distal portion of third stent-graft 24, including distal end 58, is positioned in the upper part of ascending aorta 101. Third lateral opening 54 is disposed in aortic arch 100 facing downstream, generally toward descending aorta 102, in a vicinity of the bifurcation of aortic arch 100 and brachiocephalic artery 103, such that third lateral opening 54 faces and aligned with inferior first lateral opening 34E of first stent-graft 20.

Alternatively, third stent-graft 24 is deployed prior to deployment of first stent-graft 20 (in which case, typically also prior to deployment of second stent-graft 22).

Deployment of the Fourth Stent-Graft

Figure 9F:
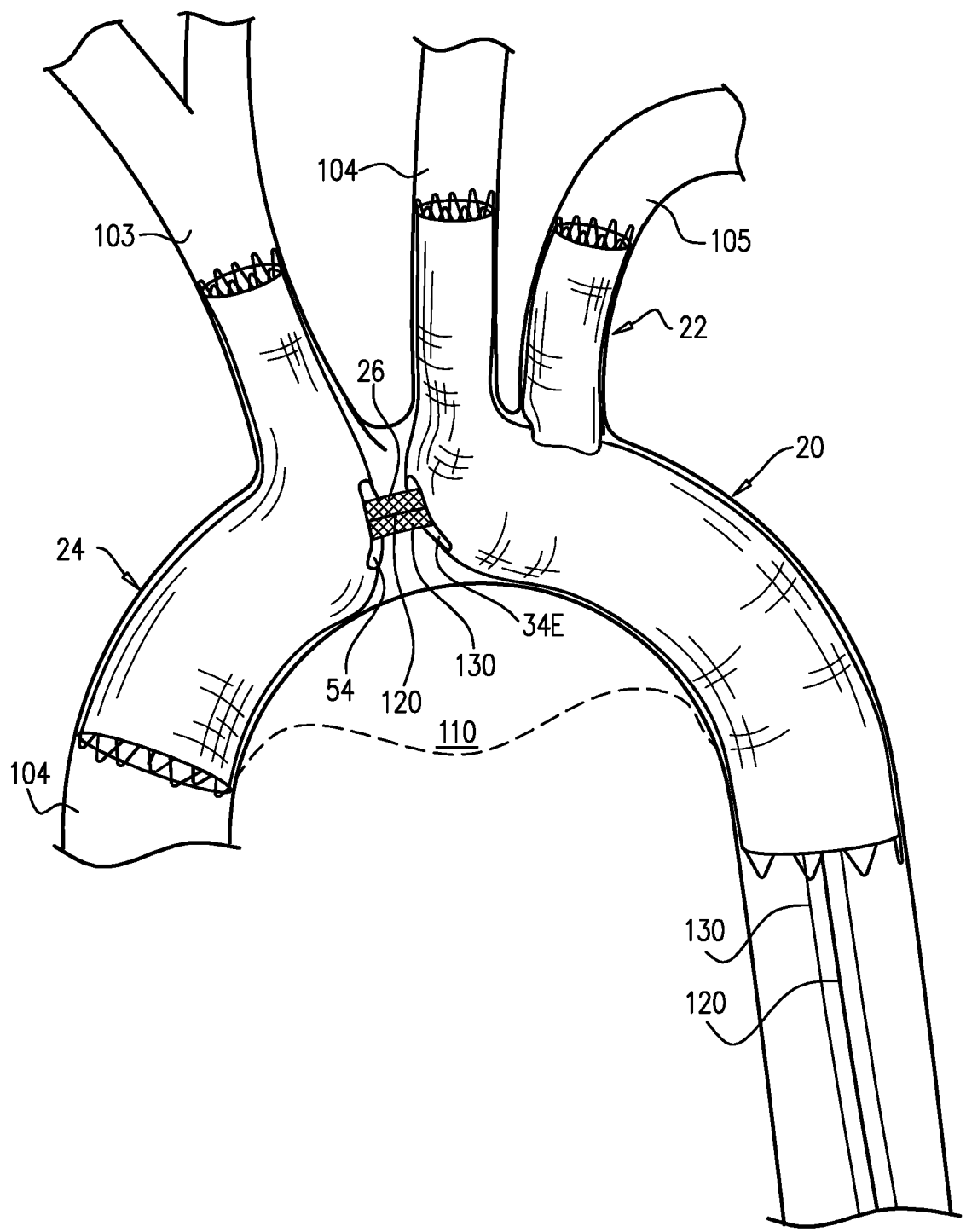

As shown in FIG. 9F, fourth stent-graft 26 is initially positioned in its radially-compressed state within an outer tube of a delivery tool (either the same outer tube 130 used to deploy the first and/or second stent-grafts, or an additional outer tube), typically near distal end 132 of the outer tube (e.g., such that at least one end of stent-graft 26 is within a distance of distal end 132, which distance equals the sum of 2 cm and an axial length of the first stent-graft). A guidewire (either the same guidewire 120 used to deploy the first and/or second stent-grafts or an additional guidewire) is advanced up descending aorta 102, through a proximal portion of first stent-graft 20, and out of inferior first lateral opening 34E. The guidewire is advanced through aortic arch 100 between inferior first lateral opening 34E of first stent-graft 20 and third lateral opening 54 of third stent-graft 24. Outer tube 130 is advanced over guidewire 120, until fourth stent-graft 26 is partially disposed in third stent-graft 24, partially disposed in first stent-graft 20, and partially disposed in aortic arch 100 between the first and third stent-grafts. The guidewire is withdrawn, leaving outer tube 130 in place.

Figure 9G:
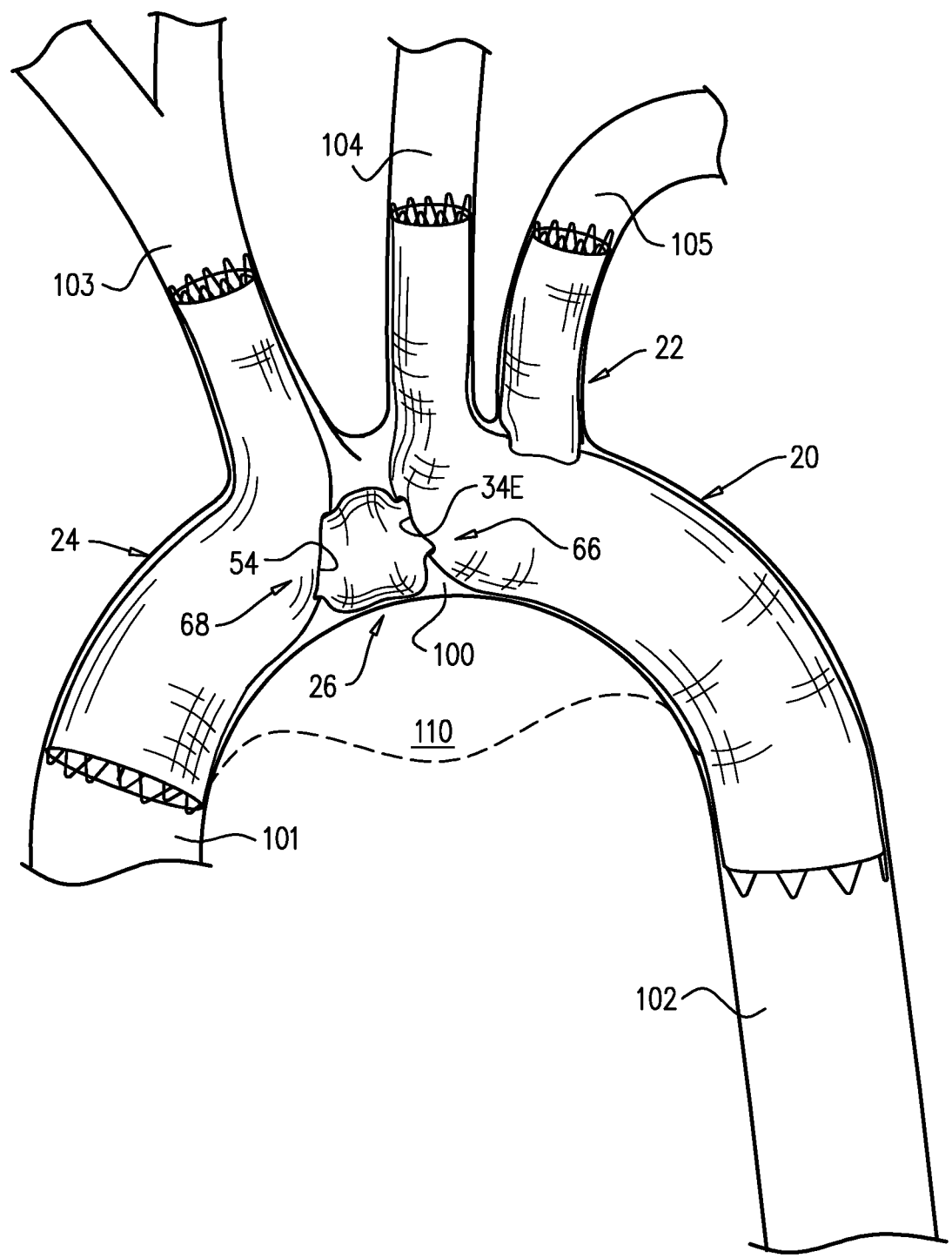

As shown in FIG. 9G, the fourth stent-graft is held in place as outer tube 130 is withdrawn, thereby delivering the fourth stent-graft from the outer tube. Optionally, techniques for holding the fourth stent-graft in place may be used that are described hereinbelow with reference to FIGS. 10 and 11A-E or FIGS. 12A-C. Fourth stent-graft 26 typically self-expands, until it assumes its radially-expanded state, upon reaching its maximum unconstrained size, and/or being constrained from further expansion by inferior first lateral opening 34E, third lateral opening 54, and/or the wall of aortic arch 100.

A proximal portion of fourth stent-graft 26, including proximal end 66, is positioned within first stent-graft 20, a distal portion of fourth stent-graft 26, including distal end 68, is positioned within third stent-graft 24, and a middle portion of fourth stent-graft 26 is positioned in aortic arch 100.

Fourth stent-graft 26 is thus adapted for transluminal delivery in its radially-compressed state through a portion of first stent-graft 20 and one of first lateral openings 34 (e.g., inferior first lateral opening 34E), and through third lateral opening 54 and a portion of third stent-graft 24, while the first and third stent-grafts are in their radially-expanded state. Alternatively, fourth stent-graft 26 is deployed through right subclavian artery 108 and brachiocephalic artery 103, and through fourth stent-graft 26 (configuration not shown).

As can be seen in FIG. 9G, upon deployment of all four stent-grafts, multi-component stent-graft system 10 defines a blood-flow path from ascending aorta 101, over aortic arch 100, and to descending aorta 102. Multi-component stent-graft system 10 additionally provides blood-flow paths to the three branches of the aortic arch: brachiocephalic artery 103, left common carotid artery 104, and left subclavian artery 105.

Figure 9H:
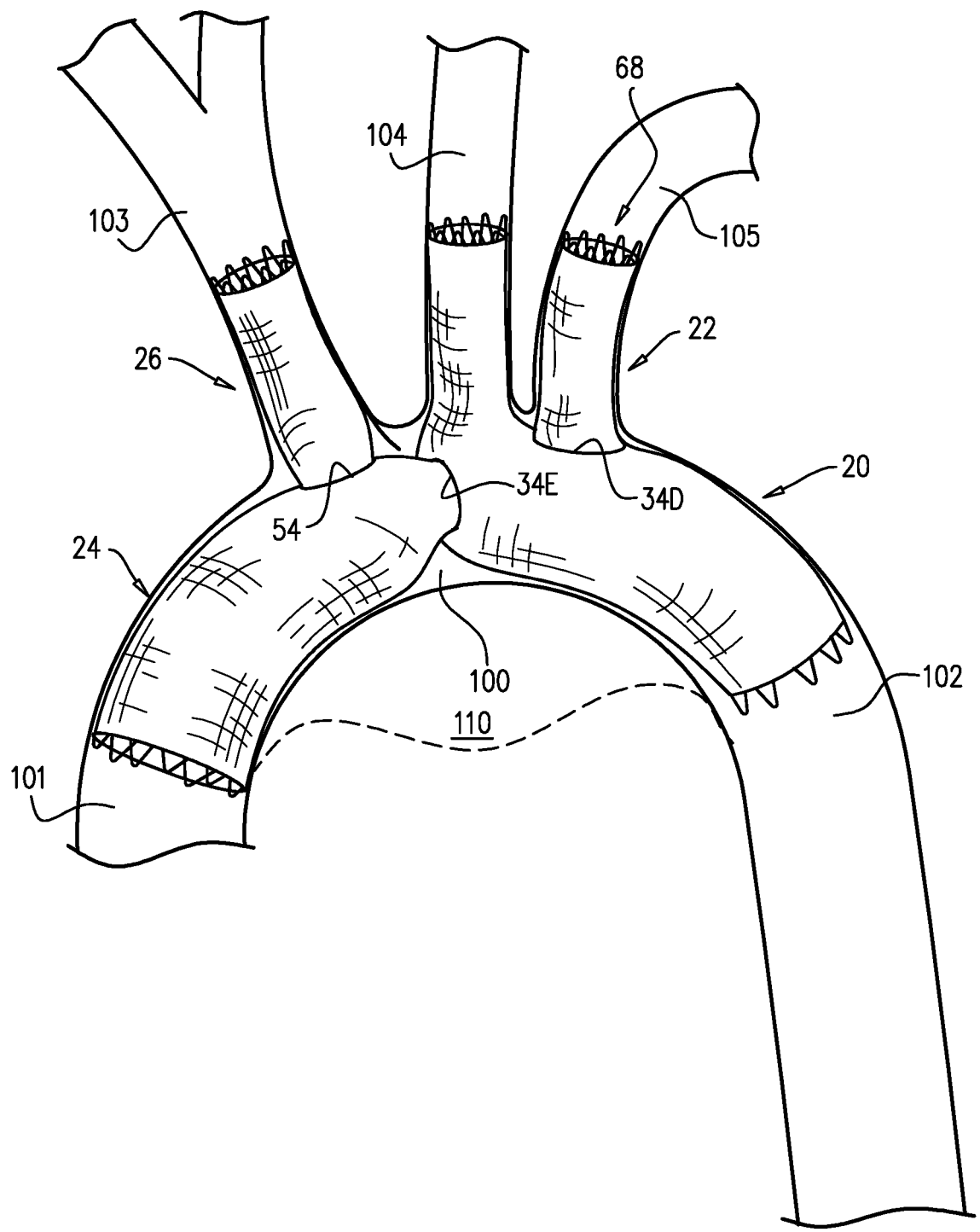
FIG. 9H is a schematic illustration of an alternative configuration and deployment of a multi-component stent-graft system, in accordance with an application of the present invention.

Reference is now made to FIG. 9H, which is a schematic illustration of an alternative configuration and deployment of stent-graft system 10, in accordance with an application of the present invention. In this deployment, first and second stent-grafts 20 and 22 are configured as described hereinabove with reference to FIGS. 7 and 8, and are deployed as described hereinabove with reference to FIGS. 9A-D. Third stent-graft 24 is configured similarly to the configuration thereof described hereinabove with reference to FIGS. 7 and 8, and is deployed through a portion of first stent-graft 20 and inferior first lateral opening 34E, such that third stent-graft 24 is disposed in aortic arch 100 and/or the upper part of ascending aorta 101, and third lateral opening 54 faces toward and is aligned with brachiocephalic artery 103. Fourth stent-graft 26 is configured as described hereinabove with reference to FIGS. 4 and 5, and is deployed through a portion of first stent-graft 20, a portion of third stent-graft 24, and third lateral opening 54 into brachiocephalic artery 103.

In yet another alternative deployment (not shown), first and second stent-grafts 20 and 22 are configured as described hereinabove with reference to FIGS. 7 and 8, and are deployed as described hereinabove with reference to FIGS. 9A-D. Third stent-graft 24 is configured as described hereinabove with reference to FIGS. 1A-2, and is deployed through a portion of first stent-graft 20 and inferior first lateral opening 34E as described hereinabove with reference to FIGS. 3G-I, mutatis mutandis. Optionally, fourth stent-graft 26 is configured as described hereinabove with reference to FIGS. 1A-2, and is deployed through a portion of first stent-graft 20, a portion of third stent-graft 24, and third lateral opening 54 as described hereinabove with reference to FIGS. 3J-L, mutatis mutandis.

Delivery Tools

As mentioned above, for some applications of the present invention, two or more of stent-grafts 20, 22, 24, and 26 are deployed from the same outer tube 130 of a delivery tool 300. For some such applications, the two or more stent-grafts are initially positioned at respective axial sites within outer tube 130, in their radially-compressed states without being fixed to each other.

Figure 10:
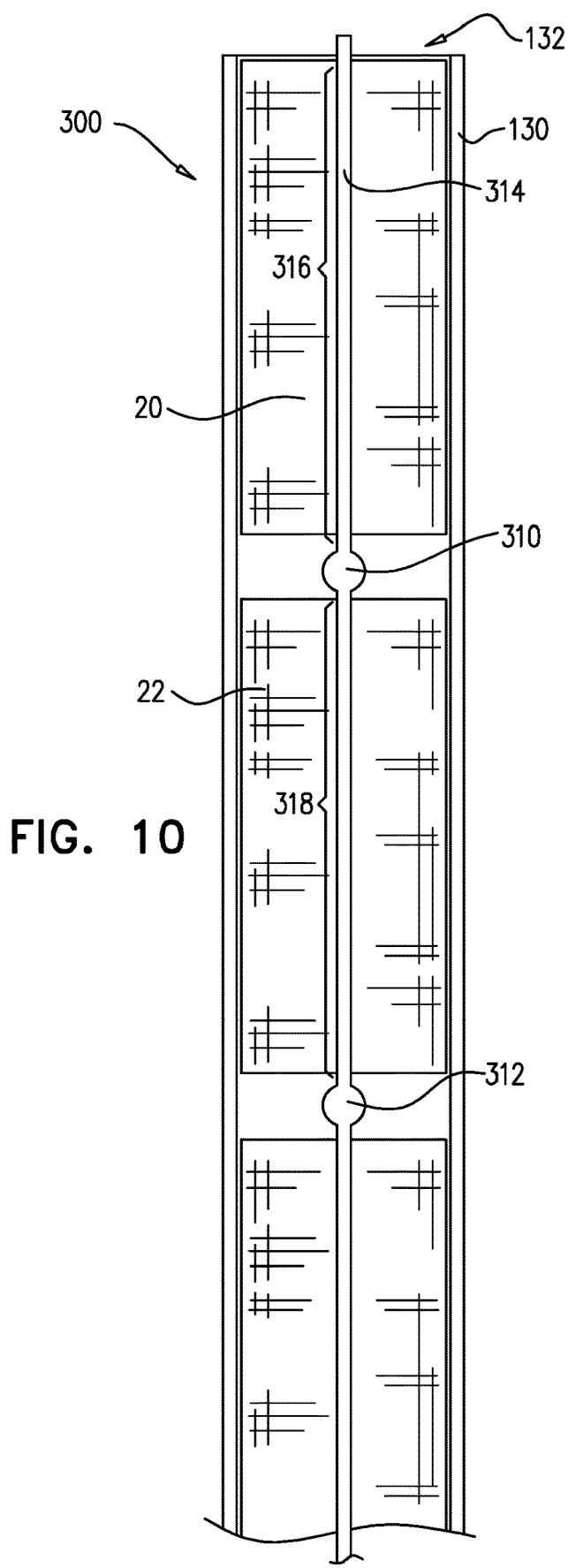
FIG. 10 is a schematic illustration of first and second stent-grafts initially positioned within an outer tube of a delivery tool, in accordance with an application of the present invention.

Reference is made to FIG. 10, which is a schematic illustration of first and second stent-grafts 20 and 24 initially positioned within outer tube 130 of a delivery tool 300, in accordance with an application of the present invention. First and second stent-grafts 20 and 22 are initially positioned at respective axial sites within outer tube 130, in their radially-compressed states without being fixed to each other. Typically, first and second stent-grafts 20 and 22 are initially positioned in the outer tube such that at least one end of one of the stent-grafts (for example, first stent-graft 20, as shown in FIG. 10) is within a distance of distal end 132 of outer tube 130, which distance equals the sum of 2 cm and an axial length of first stent-graft 20. Additional stent-grafts (e.g., third stent-graft 24 and/or fourth stent-graft 26) may also be initially positioned at respective axial sites within outer tube 130.

For some applications, delivery tool 300 is shaped so as to define first and second stopper elements 310 and 312, which are configured and initially positioned to prevent movement of first and second stent-grafts 20 and 22, respectively, in a proximal direction away from distal end 132 of outer tube 130. For some applications, as shown in FIG. 10, delivery tool 300 further comprises an inner longitudinal member 314, which is initially positioned such that first and second portions 316 and 318 thereof are within first and second stent-grafts 20 and 22, respectively, and inner longitudinal member 314 is shaped so as to define first and second stopper elements 310 and 312. The stopper elements are shaped and/or sized to prevent passage thereof through the stent-grafts when in their radially-compressed states. If additional stent-grafts are also positioned in the outer tube, the inner longitudinal member is typically shaped so as to define additional respective stopper elements. Typically, inner longitudinal member 314 is shaped so as to define a lumen therethrough (not shown), through which guidewire 120 may pass, as shown in a number of the figures described hereinabove.

Reference is made to FIGS. 11A-E, which are schematic illustrations showing the deployment of first and second stent-grafts 20 and 22 using deployment tool 300 configured as described hereinabove with reference to FIG. 10, in accordance with an application of the present invention. Although these illustrations show the deployment of first and second stent-grafts 20 and 22 in the configuration described hereinabove with reference to FIGS. 1A-C and 2, this deployment technique may also be used to deploy additional stent-grafts (such as third and/or fourth stent-grafts 24 and 26), and/or stent-grafts with other configurations, including the other configurations described hereinabove with reference to FIGS. 4-5 and FIGS. 7-8, or other stent-grafts known in the art.

Figure 11A:
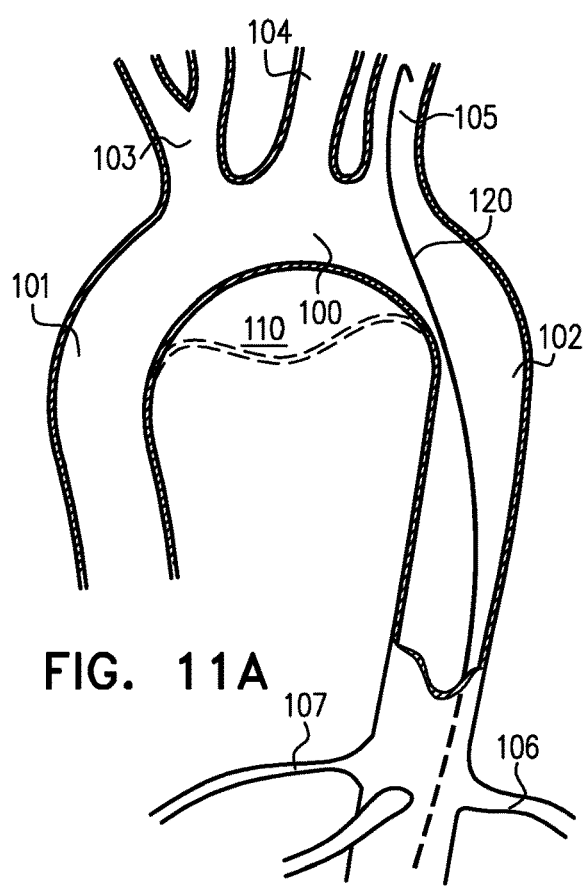
FIGS. 11A-E are schematic illustrations showing the deployment of the first and second stent-grafts using the deployment tool of FIG. 10, in accordance with an application of the present invention.

The exemplary procedure begins with the advancing of guidewire 120 up descending aorta 102 and into a first one of the branches of aortic arch 100, such as left subclavian artery 105, as shown in FIG. 11A.

Figure 11B:
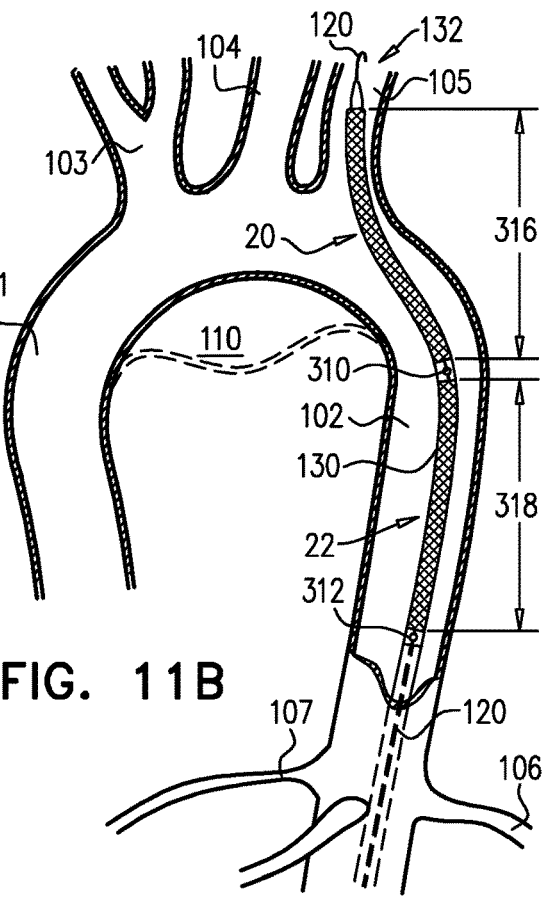

As shown in FIG. 11B, first stent-graft 20 is initially positioned in its radially-compressed state within outer tube 130 of delivery tool 300, typically near distal end 132 of the outer tube, surrounding first portion 316 of inner longitudinal member 314. Second stent-graft 22 is initially positioned in its radially-compressed state within outer tube 130, typically near a proximal end of the first stent-graft, surrounding second portion 318. First stopper elements 310 is positioned proximally adjacent to first stent-graft 20 (and distal to second stent-graft 22), and second stopper element 312 is positioned proximally adjacent to second stent-graft 22. For applications in which additional stent-grafts are also deployed, additional stopper elements are typically provided and positioned in like manner.

Outer tube 130 is advanced over guidewire 120, until first stent-graft 20 is partially disposed in left subclavian artery 105 and partially disposed in the upper part of descending aorta 102. The guidewire is withdrawn, leaving outer tube 130 in place.

Figure 11C:
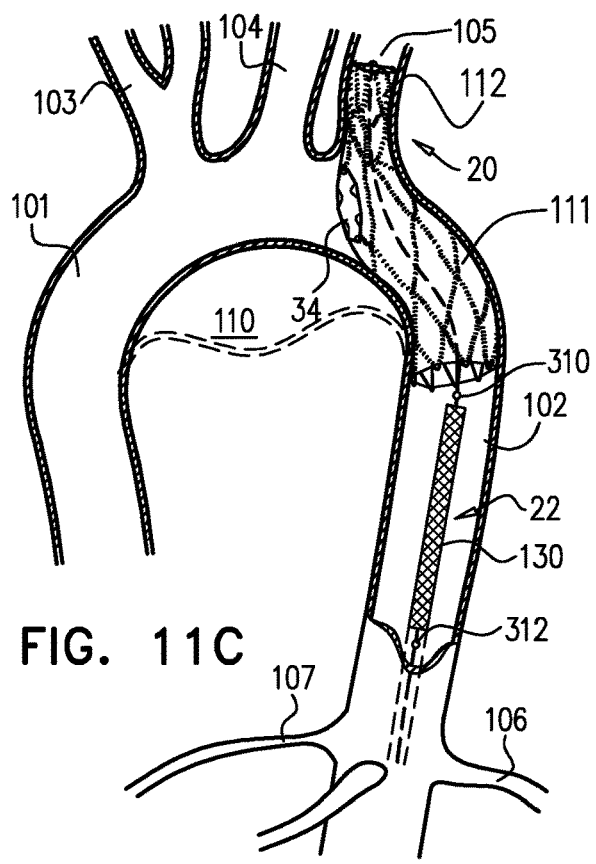

As shown in FIG. 11C, as outer tube 130 is withdrawn, first stent-graft 20 is held in place by first stopper element 310, which prevents movement of the first stent-graft in a proximal direction. First stent-graft 20 typically self-expands, until it assumes its radially-expanded state, upon reaching its maximum unconstrained size, and/or being constrained from further expansion by the wall of the blood vessels.

Figure 11D:
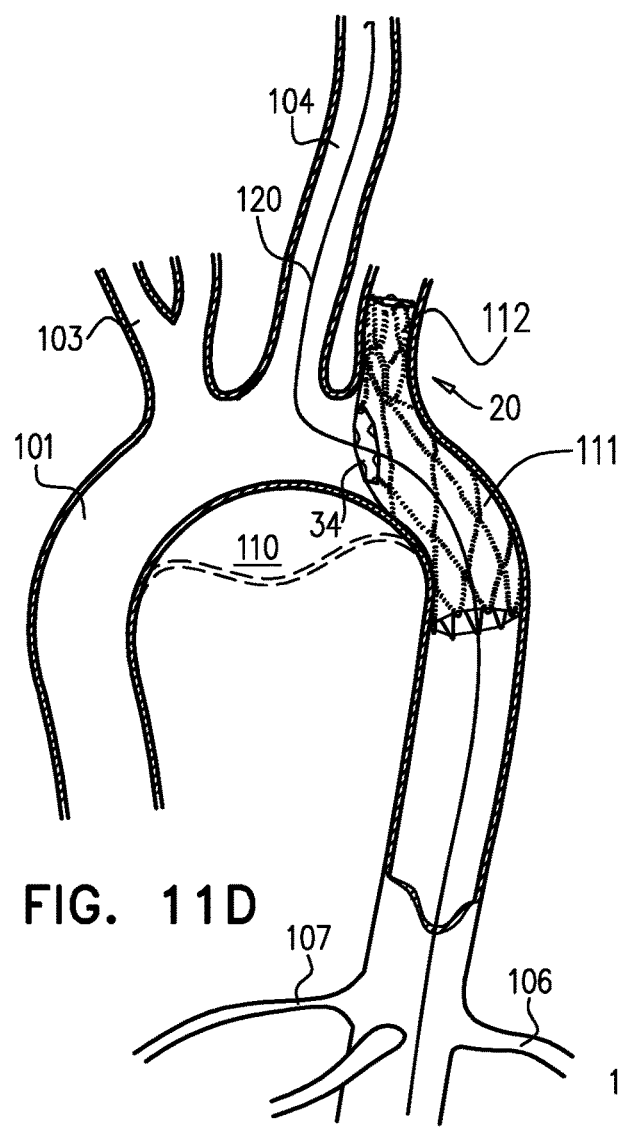

Guidewire 120 is advanced up descending aorta 102, through a proximal portion of first-stent-graft 20, out of first lateral opening 34, and into a second one of the branches of aortic arch 100, such as left common carotid artery 104, as shown in FIG. 11D.

Figure 11E:
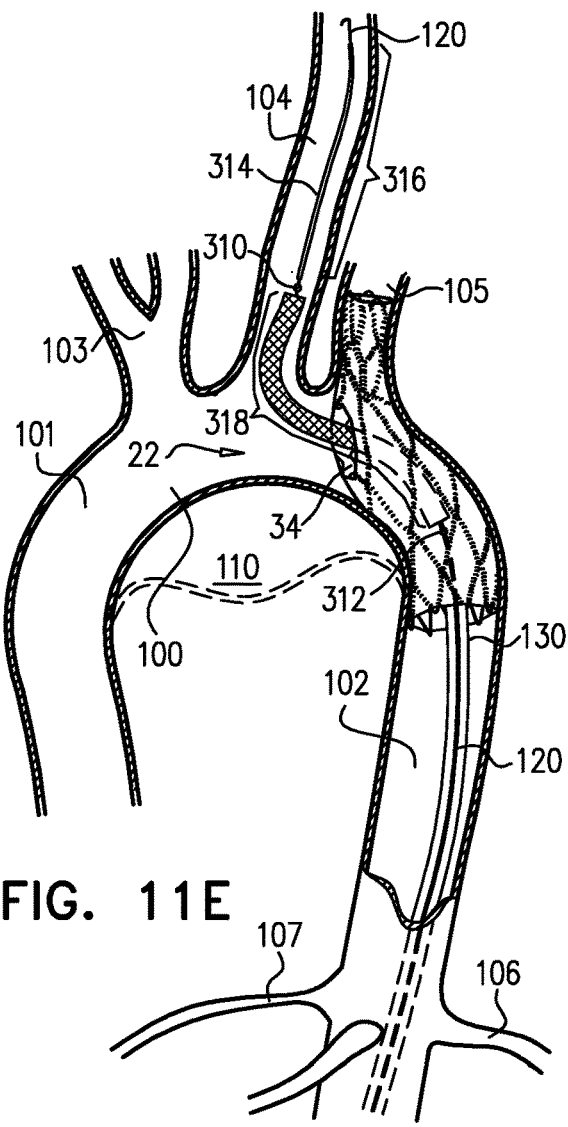

Outer tube 130 is advanced over guidewire 120, until second stent-graft 22 is partially disposed in left common carotid artery 104 and partially disposed within radially-expanded first stent-graft 20 in the upper part of descending aorta 102, as shown in FIG. 11E. First portion 316 of inner longitudinal member 314 is disposed in left common carotid artery 104, further up the artery than the distal end of second stent-graft 22. When outer tube 130 is subsequently withdrawn (not shown), second stent-graft 22 is held in place by second stopper element 312, which prevents movement of the second stent-graft in a proximal direction. Deployment continues as described hereinabove.

Figure 12C:
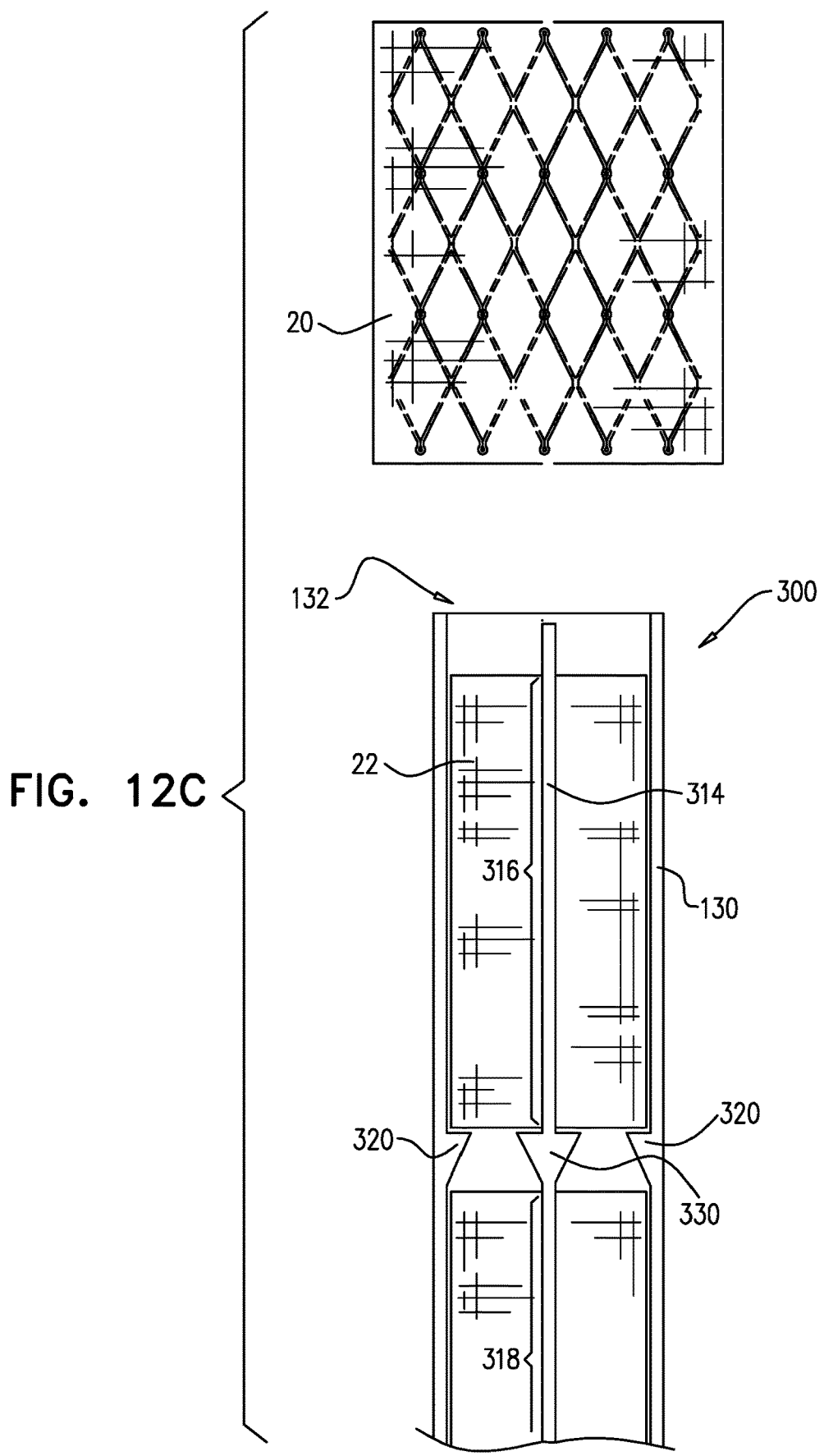

Reference is made to FIGS. 12A-C, which are schematic illustrations of another configuration of delivery tool 300, in accordance with an application of the present invention. Except as described below, this configuration of the delivery tool is generally similar to the configuration described hereinabove with reference to FIG. 10. As in the configuration described hereinabove, first and second stent-grafts 20 and 22 are initially positioned at respective axial sites within outer tube 130, in their radially-compressed states without being fixed to each other, as shown in FIG. 12A. Additional stent-grafts (e.g., third stent-graft 24 and/or fourth stent-graft 26) may also be initially positioned at respective axial sites within out tube 130. Inner longitudinal member 314 is initially positioned such that first and second portions 316 and 318 thereof are within first and second stent-grafts 20 and 22, respectively.

Inner longitudinal member 314 is shaped so as to define a stopper element 330. The stopper element is shaped and/or sized to prevent passage thereof through the stent-grafts when in their radially-compressed states, but to be withdrawable in the proximal direction through the stent-graft(s) positioned proximal to the stopper element, when the stent-grafts are in their radially-compressed states. For example, stopper element 330 is configured to be withdrawable in the proximal direction through second stent-graft 22, and after being thus withdrawn, to prevent movement of second stent-graft 22 in the proximal direction. For some applications, an inner surface of outer tube 130 is shaped so as to define at least one pusher element 320, which is configured to prevent movement of at least one of the first and second stent-grafts in the proximal direction, but to allow advancement of the stent-grafts in the distal direction with respect to the outer tube. If additional stent-grafts are also positioned in the outer tube, the inner longitudinal member is optionally shaped so as to define one or more spacer elements 332, which are configured to maintain adjacent stent-grafts slightly axially spaced apart from each other, and to slide bidirectionally through the additional stent-grafts.

FIG. 12A shows the stent-grafts in their initial positions in outer tube 130. As shown in FIG. 12B, after first stent-graft 20 has been positioned at a desired anatomical location, outer tube 130 is withdrawn in a proximal direction (downward in the figure), while holding inner longitudinal member 314 stationary. Stopper element 330 prevents proximal movement of the first stent-graft, causing the first stent-graft to be deployed from outer tube 130, and to self-expand around first portion 316 of inner longitudinal member 314. The second set of one or more pusher elements 320 prevents proximal movement of second stent-graft 22, so that the second stent-graft is now positioned near distal end 132 of outer tube 130, still surrounding second portion 318 of inner longitudinal member 314.

As shown in FIG. 12C, inner longitudinal member 314 is withdrawn in a proximal direction. Pusher element(s) 320 prevent proximal motion of second stent-graft 22, while stopper element 330 of inner longitudinal member 314 slides proximally through second stent-graft 22. As a result, the second stent-graft remains positioned near distal end 132, and now surrounds first portion 316, rather than second portion 318, of inner longitudinal member 314. The second stent-graft is now ready for deployment. This technique obviates the need for first portion 316 of inner longitudinal member 314 to be extended up a target blood vessel, such as shown in FIG. 11E.

In some applications of the present invention, a kit is provided that comprises two or more of stent-grafts 20, 22, 24, and/or 26.

For some applications, one or more of stent-grafts 20, 22, 24, and/or 26 comprise one or more anchoring elements, such as barbs, that extend radially outwardly when the stent-grafts assume their radially-expanded states. The anchoring elements anchor the prosthesis to a vascular wall, helping prevent dislodgement.

Although stent-grafts 20, 22, 24, and 26 have sometimes been described hereinabove as being deployed in an area of the thoracic aorta, the stent-grafts may, for some applications, also be deployed in another main body lumen and one or more of its branching body lumens, such as another main blood vessel and one or more of its branching blood vessels. For example:

the first stent-graft may extend from the external carotid artery into the internal carotid artery, such that the first lateral opening faces the common carotid artery, and the second stent-graft may extend from the external carotid artery, through the first lateral opening, and into the common carotid artery; or the first stent-graft may extend from the external iliac artery into the internal iliac artery, such that the first lateral opening faces the common iliac artery, and the second stent-graft may extend from the external iliac artery, through the first lateral opening, and into the common iliac artery.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

PCT Application PCT/IL2008/000287, filed Mar. 5, 2008, which published as PCT Publication WO 2008/107885 to Shalev et al.

U.S. application Ser. No. 12/529,936, which published as US Patent Application Publication 2010/0063575 to Shalev et al.

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

PCT Application PCT/IB2010/052861, filed Jun. 23, 2010, which published as PCT Publication WO 2010/150208

PCT Application PCT/IL2010/000564, filed Jul. 14, 2010, entitled, "Sideport engagement and sealing mechanism for endoluminal stent-grafts," which published as PCT Publication WO 2011/007354

PCT Application PCT/IL2010/000917, filed Nov. 4, 2010, which published as PCT Publication WO 2011/055364

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a multi-component stent-graft system, which comprises:
   a first stent-graft, which is configured to assume radially-expanded and radially-compressed states;
   a second stent-graft, which is configured to assume radially-expanded and radially-compressed states; and
   a delivery tool, which comprises:
      an outer tube, in which the first and the second stent-grafts are initially positioned in their radially-compressed states without being fixed to each other, at respective axial sites within the outer tube such that at least one end of the first stent-graft is within a distance of a distal end of the outer tube, which distance equals the sum of 2 cm and an axial length of the first stent-graft; and
      an inner longitudinal member, which (a) is initially positioned such that first and second portions thereof are within the first and the second stent-grafts, respectively, and (b) is shaped so as to define a stopper element, which is:
         configured and initially positioned to prevent movement of the first stent-graft in a proximal direction away from the distal end of the outer tube, and
         configured to be withdrawable in the proximal direction through the second stent-graft, and after being thus withdrawn, to prevent movement of the second stent-graft in the proximal direction.

2. Apparatus comprising a multi-component stent-graft system, which comprises:
   a first stent-graft, which is configured to assume radially-expanded and radially-compressed states;
   a second stent-graft, which is configured to assume radially-expanded and radially-compressed states; and
   a delivery tool, which comprises an outer tube, in which the first and the second stent-grafts are initially positioned at respective axial sites within the outer tube, in their radially-compressed states without being fixed to each other,
   wherein the first and second stent-grafts are initially positioned in the outer tube such that at least one end of the first stent-graft is within a distance of a distal end of the outer tube, which distance equals the sum of 2 cm and an axial length of the first stent-graft, and
   wherein an inner surface of the outer tube of the delivery tool is shaped so as to define first and second stopper elements, which are configured and initially positioned to prevent movement of the first and the second stent-grafts, respectively, in a proximal direction away from the distal end of the outer tube.

3. The apparatus according to claim 1, wherein an inner surface of the outer tube is shaped so as to define at least one pusher element, which is configured to prevent movement of at least one of the first and the second stent-grafts in the proximal direction.

4. The apparatus according to claim 1, wherein the delivery tool further comprises at least one pusher element, which is configured to prevent movement of at least one of the first and the second stent-grafts in the proximal direction.

5. The apparatus according to claim 1, wherein the inner longitudinal member is shaped so as to define a lumen therethrough.

6. The apparatus according to claim 2, wherein the second stent-graft is initially positioned in the outer tube such that the first stent-graft is longitudinally between the distal end of the outer tube and the second stent-graft.

7. The apparatus according to claim 1, wherein the first stent-graft is shaped so as to define a first lateral opening.

8. The apparatus according to claim 7,
   wherein the first stent-graft comprises a first generally tubular support element and a first covering element, which is attached to the first support element so as to at least partially cover the first support element, and the first covering element and the first support element are shaped so as to together define the first lateral opening,
   wherein the second stent-graft comprises a second generally tubular support element and a second covering element, which is attached to the second support element so as to at least partially cover the second support element, and
   wherein the first and the second stent-grafts are configured such that the second covering element forms a blood-impervious seal with the first covering element around the first lateral opening when the second stent-graft is disposed therethrough, and the first and the second stent-grafts are in their radially-expanded states.

9. The apparatus according to claim 1, wherein the first and the second stent-grafts are configured for transluminal delivery for transport to respective sites within a body lumen when in their radially-compressed states.

10. The apparatus according to claim 1, wherein a greatest perimeter of the first stent-graft is between 4.5 and 19 cm, when the first stent-graft is unconstrained in its radially-expanded state.

11. The apparatus according to claim 1, wherein a greatest perimeter of the second stent-graft is between 9 and 22 cm, when the second stent-graft is unconstrained in its radially-expanded state.

12. A method comprising:
   transvascularly introducing, into vasculature of a patient, a delivery tool, which includes (a) an outer tube, in which first and second stents are initially positioned in radially-compressed states without being fixed to each other, at respective axial sites within the outer tube such that at least one end of the first stent-graft is within a distance of a distal end of the outer tube, which distance equals the sum of 2 cm and an axial length of the first stent-graft, and (b) an inner longitudinal member, which (i) is initially positioned such that first and second portions thereof are within the first and second stents, respectively, and (ii) is shaped so as to define a stopper element, which is (1) configured and initially positioned to prevent movement of the first stent in a proximal direction away from the distal end of the outer tube, and (2) configured to be withdrawable in the proximal direction through the second stent, and after being thus withdrawn, to prevent movement of the second stent in the proximal direction;

deploying the first stent from a distal end of the outer tube, such that the first stent transitions to a radially-expanded state, by withdrawing the outer tube in the proximal direction, such that the stopper element prevents the movement of the first stent in the proximal direction; and after the first stent transitions to the radially-expanded state, deploying the second stent from the distal end of the outer tube, such that the second stent transitions to a radially-expanded state, by:
- withdrawing the inner longitudinal member in the proximal direction, such that the stopper element passes through the second stent, and
- withdrawing the outer tube in the proximal direction, such that the stopper element prevents the movement of the second stent in the proximal direction.

* * * * *